US007015229B2

(12) United States Patent
Fu et al.

(10) Patent No.: US 7,015,229 B2
(45) Date of Patent: Mar. 21, 2006

(54) SUBSTITUTED PYRIMIDINONES AND PYRIMIDINTHIONES

(75) Inventors: Jian-Min Fu, Kalamazoo, MI (US); Jeffrey W. Corbett, Portage, MI (US); Michael Dalton Ennis, Mattawan, MI (US); Kristine E. Frank, Portage, MI (US); Robert Louis Hoffman, Kalamazoo, MI (US); Patrick R. Verhoest, Augusta, MI (US)

(73) Assignee: Pfizer Inc, New York, NY (US)

( * ) Notice: Subject to any disclaimer, the term of this patent is extended or adjusted under 35 U.S.C. 154(b) by 268 days.

(21) Appl. No.: 10/370,259

(22) Filed: Feb. 20, 2003

(65) Prior Publication Data

US 2003/0195222 A1    Oct. 16, 2003

Related U.S. Application Data

(60) Provisional application No. 60/359,164, filed on Feb. 22, 2002.

(51) Int. Cl.
*C07D 239/46* (2006.01)
*C07D 401/04* (2006.01)
*C07D 403/12* (2006.01)
*A61K 31/506* (2006.01)

(52) U.S. Cl. .................. 514/269; 544/319
(58) Field of Classification Search ............... 544/319; 514/269
See application file for complete search history.

(56) References Cited

U.S. PATENT DOCUMENTS 6,043,260 A    3/2000    Chen et al. .................. 514/348

FOREIGN PATENT DOCUMENTS

| EP | 0826673 A1 | 4/1996 |
|---|---|---|
| EP | 1097709 A2 | 5/2001 |
| WO | WO 00/69832 | 11/2000 |
| WO | WO 01/68614 | 9/2001 |
| WO | WO 02/06242 | 1/2002 |

OTHER PUBLICATIONS

Kehne et al., PubMed Abstract (Curr Drug Targets CNS Neurol Disord. 1(5):467-93) Oct. 2002.*
Mitchell, PubMed Abstract (Neurosci Biobehav Rev. 22(5): 635-51) Sep. 1998.*
Suarez et al., PubMed Abstract (Medicina (B Aires) 59(4): 385-92) 1999.*
van Heeswijk et al., PubMed Abstract (Antivir Ther 6(4): 201-29) Dec. 2001.*
Damazio, Alzheimer's Disease and Related Dementias, Cecil Textbook of Medicine, vol. 2, pp. 1992-1996, 1996.*
Layzer, Degenerative Diseases of the Nervous System, Cecil Textbook of Medicine, vol. 2, pp. 2050-2057, 1996.*
Simone, Oncology: Introduction, Cecil Textbook of Medicine, vol. 1, pp. 1004-1010, 1996.*
Arato M. et al., Biol. Psychiatry, 1989, 25:355.
Banki C.M. et al., Am. J. Psychiatry, 1987, 144:873.
Berridge, C. W. and A.J. Dunn, Regul. Peptides, 1986, 16:83.
Berridge, C. W. and A. J. Dunn, Horm. Behav., 1987, 21:393.
Berridge, C. W. and A. J. Dunn, Brain Research Reviews, 1990, 15:71.
Blalock, Physiological Reviews, 1989, 69:1.
Britton, K. T. , et al., Psychopharmacology, 1985, 86:170.
Britton, K. T. , Psychopharmacology, 1988, 94:306.
De Souze, E.B., Hosp. Practice, 1988, 23:59.
De Souza, E. B. et al., J. Neurosci., 1985, 5:3189.
France et al., Biol. Psychiatry, 1988, 28:86.
Gold, P. W. et al., Am. J. Psychiatry, 1984, 141:619.
Gold, P. W. et al., New Engl. J. Med., 1986, 314:1129.
Grigoriadis, et al., Neuropsychopharmacology, 1989, 2:53.
Holaboer F. et al., Psychoneuroendocrinology, 1984, 9:147.
Koob G. F., Persp. Behav. Med., 1985, 2:39.
Morley, J.E. et al., Life Sci., 1987, 41:527.
Nemeroff, et al., Science, 1984, 226:1342.
Nemeroff C.B., et al., Arch. Gen Psychiatry, 1988, 45:577.
Rivier J. et al., Proc. Natl. Acad. Sci (USA), 1983, 80:4851.
Sapolsky, R. M. , Arch. Gen. Psychiatry, 1989, 46:1047 (Abstract only).
Vale W. et al, Science, 1981, 213:1394.
Vale W. et al, Rec. Prog. Horm. Res., 1983, 39:245.
D. R. Britton, Intraventricular Corticotropin-Releasing Factor Enhances Behavioral Effects of Novelty, Life Sciences, Vo. 31, 1982, pp. 363-367, Pergamon Press, U. S. A.

* cited by examiner

*Primary Examiner*—Deepak Rao
(74) *Attorney, Agent, or Firm*—Steve T. Zelson; Jolene W. Appleman

(57) ABSTRACT

This invention relates to substituted pyrimidinone and pyrimidithione derivatives that bind with high affifnity to CRF1 receptors, including human CRF1 receptors. This invention also relates to methods of using the compounds of the invention to treat a disorder or condition, the treatment of which can be effected or facilitated by antagonizing a CRF receptor, such as CNS disorders or diseases, particularly anxiety disorders, and depression and stress related disorders.

21 Claims, No Drawings

SUBSTITUTED PYRIMIDINONES AND PYRIMIDINTHIONES

CROSS REFERENCE TO RELATED APPLICATIONS

This application claims the benefit of U.S. Provisional Application Ser. No. 60/359,164 filed on Feb. 22, 2002.

FIELD OF THE INVENTION

The present invention relates generally to compounds that bind to CRF receptors and particularly to substituted pyrimidinone and pyrimidithione derivatives that are CRF1 receptor antagonists, and to the use thereof as treatment for disorders that are associated with CRF or CRF1 receptors.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response in the immune system to physiological, psychological, and immunological stressors [J. E. Blalock, *Physiological Reviews* 69:1 (1989); J. E. Morley, *Life Sci.* 41:527 (1987)].

There is evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for a review, see: E. B. De Souze, *Hosp. Practice* 23:59 (1988)].

Anxiety disorders are a group of diseases, recognized in the art, that includes phobic disorders, anxiety states, post-traumatic stress disorder and atypical anxiety disorders [The Merck Manual of Diagnosis and Therapy, 16$^{th}$ edition (1992)]. Emotional stress is often a precipitating factor in anxiety disorders, and such disorders generally respond to medications that lower response to stress.

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders, and is known to produce anxiogenic effects in animals. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn, *Regul. Peptides* 16:83 (1986)]. Preliminary studies using the putative CRF receptor antagonist α-helical ovine CRF (9–41) in a variety of behavioral paradigms demonstrates that the antagonist produces "anxiolytic-like" effects that are qualitatively similar to the benzodiazepines [C. W. Berridge and A. J. Dunn, *Horm. Behav.* 21:393 (1987), *Brain Research Reviews* 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharnacology* 88:147 (1986)] in rats. The benzodiazepine receptor antagonist Ro 15–1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)]. The mechanisms and sites of action through which conventional anxiolytics and antidepressants produce their therapeutic effects remain to be elucidated. Preliminary studies, examining the effects of a $CRF_1$, receptor antagonist peptide (α-helical $CRF_{9-41}$) in a variety of behavioral paradigms, have demonstrated that the $CRF_1$, antagonist produces "anxiolytic-like" effects qualitatively similar to the benzodiazepines [for a review, see: G. F. Koob and K. T. Britton, In: *Corticotropin-Releasing Factor: Basic and Clinical Studies of a Neuropeptide*, E. B. De Souza and C. B. Nemeroff eds., CRC Press p.221 (1990)].

The use of $CRF_1$, antagonists for the treatment of Syndrome X has also been described in U.S. patent application Ser. No. 09/696,822, filed Oct. 26, 2000, and European Patent Application No. 003094414, filed Oct. 26, 2000, which are also incorporated in their entireties herein by reference. Methods for using $CRF_1$ antagonists to treat congestive heart failure are described in U.S. Ser. No. 09/248,073, filed Feb. 10, 1999, now U.S. Pat. No. 6,043, 260 (Mar. 28, 2000) which is also incorporated herein in its entirety by reference.

CRF is known to have a broad extrahypothalmic distribution in the CNS, contributing therein to a wide spectrum of autonomic behavioral and physiological effects [see, e.g., Vale et al., 1983; Koob, 1985; and E. B. De Souze et al., 1985]. For example, CRF concentrations are significantly increased in the cerebral spinal fluid of patients afflicted with affective disorder or major depression [see, e.g., Nemeroff et al., 1984; Banki et al., 1987; France et al., 1988; Arato et al., 1989]. Moreover, excessive levels of CRF are known to produce anxiogenic effects in animal models [see, e.g., Britton et al., 1982; Berridge and Dunn, 1986 and 1987], and $CRF_1$ antagonists are known to produce anxiolytic effects; accordingly, therapeutically effective amounts of compounds provided herein are, for example, determined by assessing the anxiolytic effects of varying amounts of the compounds in such animal models.

WO 02/06242 and WO 01/68614 disclose various compounds that can bind with high affinity and high selectivity to $CRF_1$ receptors. The compounds are useful for treating CNS-related disorders particularly affective disorders and diseases, and acute and chronic neurological disorders and diseases.

Disclosed herein are novel substituted pyrimidinone and pyrimidithione derivatives, which are CRF1 receptor antagonists and are useful in the treatment of certain disorders or conditions, such as anxiety disorders, depression, and stress related disorders.

SUMMARY OF THE INVENTION

The present invention provides a compound of Formula I,

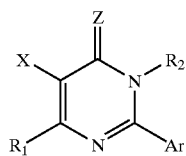

Formula I a stereoisomer thereof, a pharmaceutically acceptable salt thereof, or a prodrug thereof, or a pharmaceutically acceptable salt of a prodrug thereof, wherein:

X is selected from $NR_3R_4$, $OR_3$, $CR_3R_5R_5$, $C(O)R_3$, $S(O)_mR_3$, $NR_3C(O)R_4$, $NR_3S(O)_mR_4$;

Z is selected from —O, —S, and —$NR_2$;

m is 0, 1, or 2;

Ar is selected from aryl, substituted aryl, heteroaryl, substituted heteroaryl; and G;

G is selected from

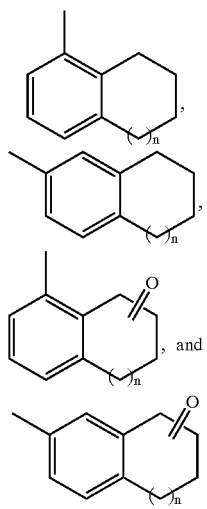

wherein each G group may have from 0–4 substituents independently selected from halogen, alkyl, substituted alkyl, cycloalkyl, substituted cycloalkyl, —$OR_5$, $SR_5$, —$NR_5R_5$, —$C(O)R_5$, —$C(S)R_5$, —CN, —$C(O)NR_5R_5$, —$C(S)NR_5R_5$, —$NR_5C(O)R_5$, —$NR_5C(S)R_5$, —$S(O)_2NR_5R_5$, —$NR_5S(O)_2R_5$, —$NO_2$, aryl, substituted aryl, heteroaryl, substituted heteroaryl;

n is 0, 1, 2, or 3;

$R_1$ and $R_5$ are independently selected from halogen, —$NO_2$, —CN, —$R_a$, —$OR_a$, —$S(O)_mR_a$, —$NR_aR_a$, —$C(O)NR_aR_a$, —$C(S)NR_aR_a$ —$S(O)_mNR_aR_a$, —$NR_aS(O)_mR_a$, —$NR_aC(O)OR_a$, —$NR_aC(S)OR_a$, —$OC(O)NR_aR_a$, —$OC(S)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_2$ is selected from —$R_a$, —$S(O)_mR_a$, —$C(O)NR_aR_a$, —$C(S)NR_aR_a$ —$S(O)_mNR_aR_a$, —$C(O)OR_a$, —$C(S)OR_a$, or —$OC(O)OR_a$;

$R_3$ and $R_4$ are independently selected from $R_a$, heterocycloalkyl, substituted heterocycloalkyl, substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided that when Ar is not G at least one of $R_3$ or $R_4$ are heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, heterocycloalkyl or substituted heterocycloalkyl;

$R_a$ each is selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

In another aspect, the present invention provides a pharmaceutical composition comprising a compound of claim 1, a stereoisomer thereof, a pharmaceutically acceptable salt thereof, or a prodrug thereof, or a pharmaceutically acceptable salt of the prodrug thereof. The compositions can be prepared in any suitable forms such as tablets, pills, powders, lozenges, sachets, cachets, elixirs, suspensions, emulsions, solutions, syrups, aerosols, and ointments.

The compounds of the inventions are CRF1 receptor antagonists and are useful for treating disorders or conditions associated with CRF or CRF1 receptors, including human CRF1 receptors.

Thus, in another aspect, the present invention provides a method of antagonizing $CRF_1$, receptors in a warm-blooded animal, comprising administering to the animal a compound of the invention at amount effective to antagonize $CRF_1$, receptors.

In still another aspect, the present invention provides a method of treating a disorder in a warm-blooded animal, which disorder manifests hypersecretion of CRF, or the treatment of which disorder can be effected or facilitated by antagonizing $CRF_1$ receptors, comprising administering to the animal a therapeutically effective amount of a compound of the invention. It is preferred that the warm-blooded animal is a mammal, and more preferred that the animal is a human.

In still another aspect, the present invention provides a method for screening for ligands for $CRF_1$ receptors, which method comprises: a) carrying out a competitive binding assay with $CRF_1$ receptors, a compound of formula I which is labelled with a detectable label, and a candidate ligand; and b) determining the ability of said candidate ligand to displace said labelled compound.

In still another aspect, the present invention provides a method for detecting CRF receptors in a tissue comprising: a) contacting a compound of formula I, which is labelled with a detectable label, with a tissue, under conditions that permit binding of the compound to the tissue; and b) detecting the labelled compound bound to the tissue.

In yet another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the CRF-1 receptor.

In yet a further aspect the present invention provides a method of treating a disorder in a mammal, particularly a human, the treatment of which disorder can be effected or faciliated by antagonizing CRF1 receptors, such as generalized anxiety disorder; social anxiety disorder; anxiety; obsessive-compulsive disorder; anxiety with co-morbid depressive illness; panic disorder; and mood disorders such as depression, including major depression, single episode depression, recurrent depression, child abuse induced depression, and postpartum depression.

DETAILED DESCRIPTION OF THE INVENTION

The present invention provides a compound of Formula I described above.

Preferred compound of formula I include compounds of formula II, III, V, and X, and below.

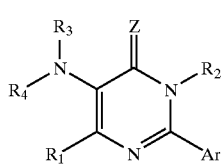

Formula II

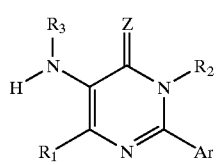

Formula III

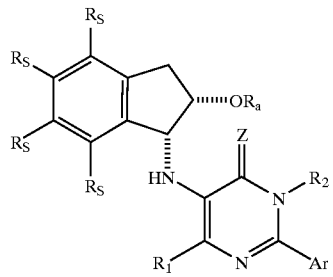

Formula V

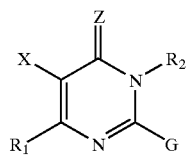

Formula X

Other preferred compounds of formula I include compounds of formula IV,

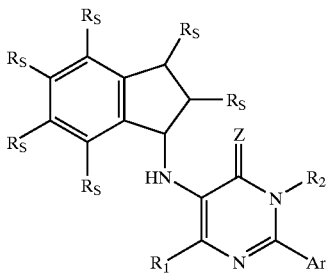

Formula IV wherein in formula IV, $R_s$ each is independently selected from halogen, —$NO_2$, —CN, —$R_a$, —$OR_a$, —$S(O)_mR_a$, —$NR_aR_a$, —C(O)$NR_aR_a$, —C(S)$NR_aR_a$ —$S(O)_mNR_aR_a$, —$NR_aS(O)_mR_a$, —$NR_aC(O)OR_a$, —$NR_aC(S)OR_a$, —OC(O)$NR_aR_a$, —OC(S)$NR_aR_a$,—$NR_aC(O)NR_aR_a$, —$NR_aC(S)NR_aR_a$, —C(O)$OR_a$, —C(S)$OR_a$, —OC(O)$R_a$, —OC(S)$R_a$, or —OC(O)$OR_a$;

Still other preferred compounds of formula I include compounds of formula VI,

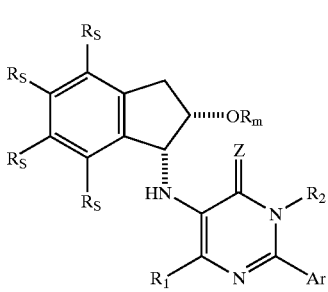

Formula VI wherein in formula VI, $R_s$ each is independently selected from halogen, —$NO_2$, —CN, —$R_a$, —$OR_a$, —$S(O)_mR_a$, —$NR_aR_a$, —$C(O)NR_aR_a$, —$C(S)NR_aR_a$ —$S(O)_mNR_aR_a$, —$NR_aS(O)_mR_a$, —$NR_aC(O)OR_a$, —$NR_aC(S)OR_a$, —$OC(O)NR_aR_a$, —$OC(S)NR_aR_a$,—$NR_aC(O)NR_aR_a$, —$NR_aC(S)NR_aR_a$, —$C(O)OR_a$, —$C(S)OR_a$, —$OC(O)R_a$, —$OC(S)R_a$, or —$OC(O)OR_a$, and $R_m$ is $C_1$–$C_6$ alkyl substituted with from 1–2 of halogen, —$NO_2$, —$NH_2$, —OH, —SH, —CN, —$C(O)NH_2$, —$C(S)NH_2$, —$C(O)$—NHalkyl, —$C(S)$—NHalkyl, —C(O)Nalkylalkyl, —C(S)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, oxo (=O), thione (=S), heterocycloalkyl, or substituted heterocycloalkyl.

Still other preferred compounds of formula I include compounds of formula VII,

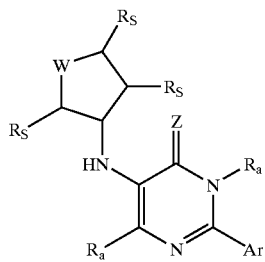

Formula VII wherein in formula VII,

W is O, $NR_p$, or $S(O)_m$; and $R_p$ each is independently selected from —$R_a$, —$S(O)_mR_a$, —$C(O)NR_aR_a$, —$C(S)NR_aR_a$ —$S(O)_mNR_aR_a$, —$C(O)OR_a$, or —$C(S)OR_a$.

Still other preferred compounds of formula I include compounds of formula VIII,

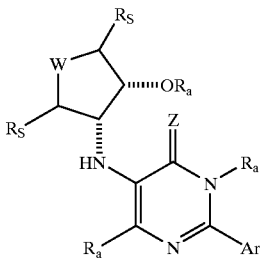

Formula VIII wherein in formula VIII,

W is O, $NR_p$, or $S(O)_m$; and $R_p$ each is independently selected from —$R_a$, —$S(O)_mR_a$, —$C(O)NR_aR_a$, —$C(S)NR_aR_a$ —$S(O)_mNR_aR_a$, —$C(O)OR_a$, or —$C(S)OR_a$.

Still other preferred compounds of formula I include compounds of formula IX

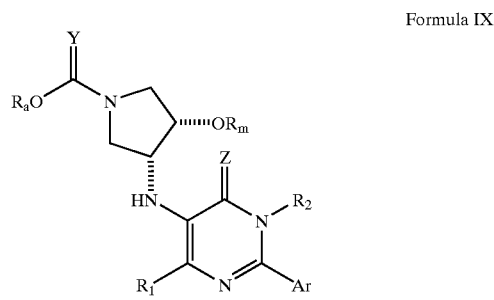

Formula IX wherein in formula IX,

Y is O or S, and $R_m$ is $C_1$–$C_6$ alkyl substituted with from 1–2 of halogen, —$NO_2$, —$NH_2$, —OH, —SH, —CN, —$C(O)NH_2$, —$C(S)NH_2$, —$C(O)$—NHalkyl, —$C(S)$—NHalkyl, —C(O)Nalkylalkyl, —C(S)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, oxo (=O), thione (=S), heterocycloalkyl, or substituted heterocycloalkyl.

Still other preferred compounds of the invention include:

compounds of Formula I where X is $NR_3R_4$;

compounds of Formula I where X is $NR_3R_4$ and one of $R_3$ or $R_4$ is aryl cycloalkyl or heteroaryl cycloalkyl;

compounds of Formula I where X is $NR_3R_4$ and one of $R_3$ or $R_4$ is aryl cycloalkyl or heteroaryl cycloalkyl and the point of attachment is the cycloalkyl ring;

compounds of Formula I where X is $NR_3R_4$ and one of $R_3$ or $R_4$ is aryl cycloalkyl or heteroaryl cycloalkyl and the point of attachment is the cycloalkyl ring and one of $R_3$ or $R_4$ is hydrogen;

compounds of Formula I where X is $NR_3R_4$ and one of $R_3$ or $R_4$ is heterocycloalkyl and one of $R_3$ or $R_4$ is hydrogen;

compounds of Formula I where X is $NR_3R_4$ and one of $R_3$ or $R_4$ is substituted aryl cycloalkyl or substituted heteroaryl cycloalkyl and the point of attachment is the cycloalkyl ring and one of $R_3$ or $R_4$ is hydrogen;

compounds of Formula I where X is $NR_3R_4$ and one of $R_3$ or $R_4$ is substituted aryl cycloalkyl or substituted heteroaryl cycloalkyl where the substituent is either alkyl or alkoxy and is on the cycloalkyl ring and the point of attachment is the cycloalkyl ring and one of $R_3$ or $R_4$ is hydrogen;

compounds of Formula I where X is $NR_3R_4$ and one of $R_3$ or $R_4$ is substituted heterocycloalkyl where the substituent is either alkyl or alkoxy and one of $R_3$ or $R_4$ is hydrogen;

compounds of Formula I where X is $NR_3R_4$ and one of $R_3$ or $R_4$ is substituted heterocycloalkyl where the substituent is either alkyl or alkoxy and the absolute stereochemistry of these ring substituents are either (R,R), (R,S), (S,R), or (S,S) and one of $R_3$ or $R_4$ is hydrogen;

compounds of Formula I where X is $NR_3R_4$ and one of $R_3$ or $R_4$ is substituted aryl cycloalkyl or substituted heteroaryl cycloalkyl where the substituent is either alkyl or alkoxy and is on the cycloalkyl ring and the absolute stereochemistry of these ring substituents are either (R,R), (R,S), (S,R), or (S,S) and the point of attachment is the cycloalkyl ring and one of $R_3$ or $R_4$ is hydrogen;

compounds of Formula I where X is $NR_3R_4$ and $R_3$ is 2-substituted-1-indanyl and $R_4$ is hydrogen;

compounds of Formula I where X is $NR_3R_4$ and $R_3$ is 2-alkoxy-1-indanyl and $R_4$ is hydrogen;

compounds of Formula I where X is $NR_3R_4$ and $R_3$ is 2(S)-alkoxy-1(R)-indanyl and $R_4$ is hydrogen;

compounds of Formula I where X is NR₃R₄ and R₃ is 4-substituted-3-pyrrolidinyl and R₄ is hydrogen;

compounds of Formula I where X is NR₃R₄ and R₃ is 4-alkoxy-3-pyrrolidinyl and R₄ is hydrogen; and compounds of Formula I where X is NR₃R₄ and R₃ is 4(S)-alkoxy-3(R)-pyrrolidinyl-1-carboxylate and R₄ is hydrogen.

Following are examples of particular compounds of the invention, with each compound being identified both by a chemical name and a structural formula immediately below the chemical name:

(1R,2S)-1-{[2-(2,4-Dichlorophenyl)-1,4-dimethyl-6-oxo-1,6-dihydropyrimidin-5-yl]amino}-2,3-dihydro-1H-inden-2-yl acetate

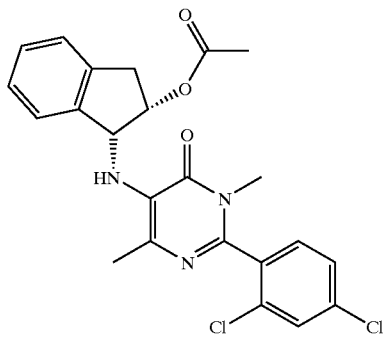

(1R,2S)-1-{[2-(2-Chloro-4-methoxphenyl)-1,4-dimethyl-6-oxo-1,6-dihydropyrimidin-5-yl]amino}-2,3-dihydro-1H-inden-2-yl acetate

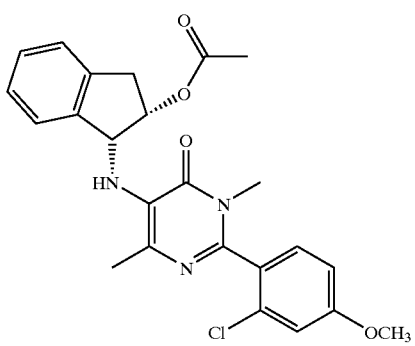

(1R,2S)-1-{[2-(2-Methyl-4-methoxyphenyl)-1,4-dimethyl-6-oxo-1,6-dihydropyrimidin-5-yl]amino}-2,3-dihydro-1H-inden-2-yl acetate

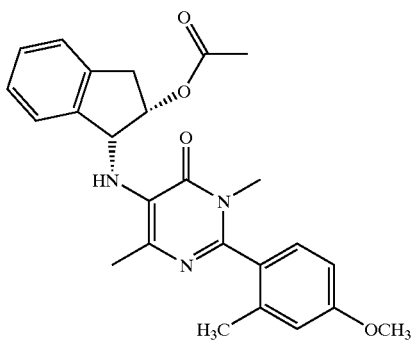

(1R,2S)-1-{[2-(2-Chloro-4-dimethylaminophenyl)-1,4-dimethyl-6-oxo-1,6-dihydropyrimidin-5-yl]amino}-2,3-dihydro-1H-inden-2-yl acetate

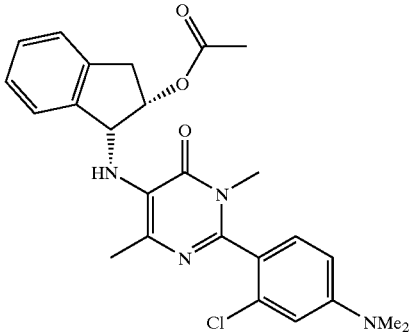

(1R,2S)-1-({2-[6-(Dimethylamino)-4-methylpyridin-3-yl]-1,4-dimethyl-6-oxo-1,6-dihydropyrimidin-5-yl}amino)-2,3-dihydro-1H-inden-2-yl acetate

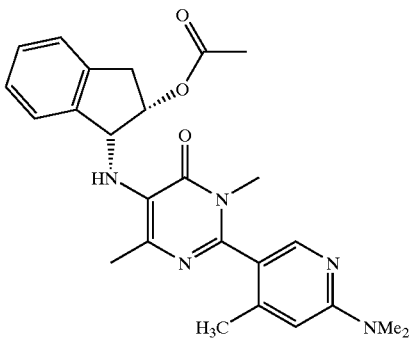

(1R,2S)-1-{[2-(6-Methoxy-2-methylpyridin-3-yl)-1,4-dimethyl-6-oxo-1,6-dihydropyrimidin-5-yl]amino}-2,3-dihydro-1H-inden-2-yl acetate

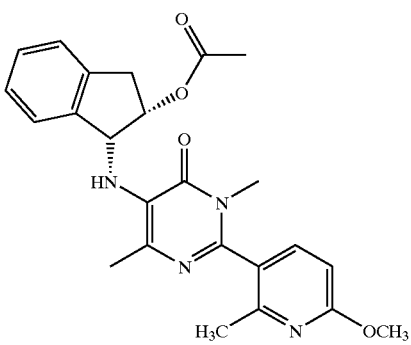

(1R,2S)-1-{[2-(2-Chloro-4-trifluoromethylphenyl)-1,4-dimethyl-6-oxo-1,6-dihydropyrimidin-5-yl]amino}-2,3-dihydro-1H-inden-2-yl acetate

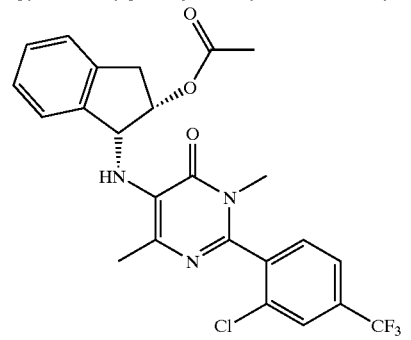

-continued (1R,2S)-1-{[2-(2-Trifluoromethyl-4-dimethylaminophenyl)-1,4-dimethyl-6-oxo-1,6-dihydropyrimidin-5-yl]amino}-2,3-dihydro-1H-inden-2-yl acetate

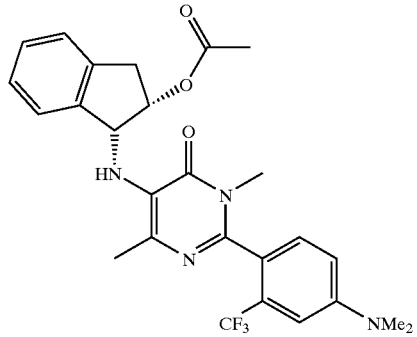

(1R,2S)-1-{[4-Ethyl-2-(2,4-dichlorophenyl)-1-methyl-6-oxo-1,6-dihydropyrimidin-5-yl]amino}-2,3-dihydro-1H-inden-2-yl acetate

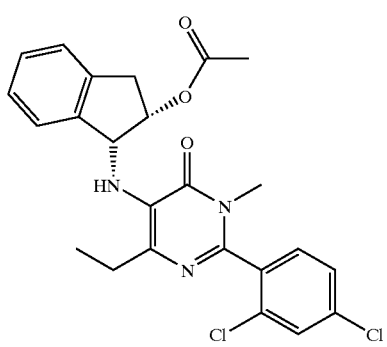

(1R,2S)-1-{[4-Ethyl-2-(2-chloro-4-methoxyphenyl)-1-methyl-6-oxo-1,6-dihydropyrimidin-5-yl]amino}-2,3-dihydro-1H-inden-2-yl acetate

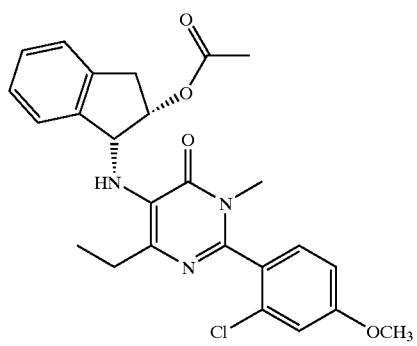

(1R,2S)-1-{[4-Ethyl-2-(2-methyl-4-methoxyphenyl)-1-methyl-6-oxo-1,6-dihydropyrimidin-5-yl]amino}-2,3-dihydro-1H-inden-2-yl acetate

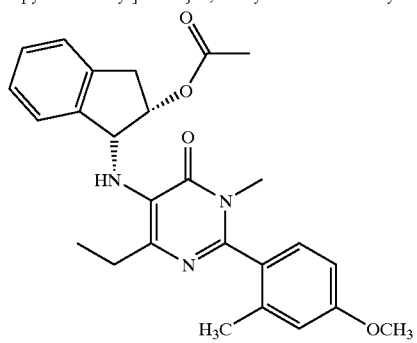

-continued (1R,2S)-1-{[4-Ethyl-2-(2-chloro-4-dimethylaminophenyl)-1-methyl-6-oxo-1,6-dihydropyrimidin-5-yl]amino}-2,3-dihydro-1H-inden-2-yl acetate

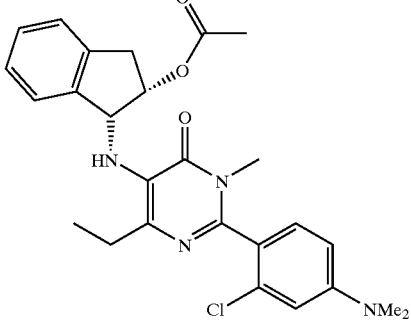

(1R,2S)-1-({2-[6-(Dimethylamino)-4-methylpyridin-3-yl]-4-ethyl-1-methyl-6-oxo-1,6-dihydropyrimidin-5-yl}amino)-2,3-dihydro-1H-inden-2-yl acetate

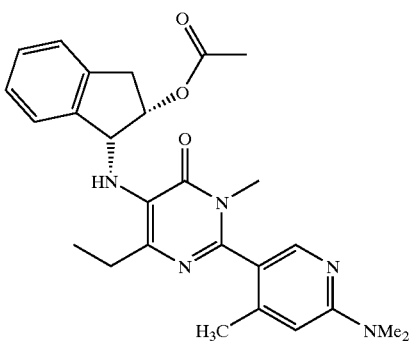

(1R,2S)-1-{[4-Ethyl-2-(6-methoxy-2-methylpyridin-3-yl)-1-methyl-6-oxo-1,6-dihydropyrimidin-5-yl]amino}-2,3-dihydro-1H-inden-2-yl acetate

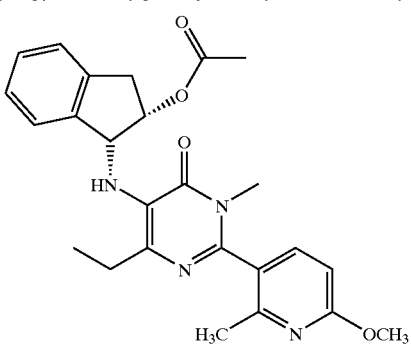

(1R,2S)-1-{[4-Ethyl-2-(2-chloro-4-trifluoromethylphenyl)-1-methyl-6-oxo-1,6-dihydropyrimidin-5-yl]amino}-2,3-dihydro-1H-inden-2-yl acetate

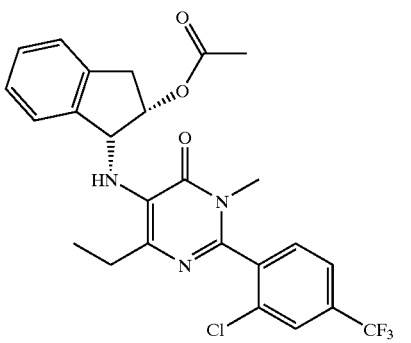

-continued (1R,2S)-1-{[4-Ethyl-2-(2-tifluoromethyl-4-dimethylaminophenyl)-1-methyl-6-oxo-1,6-dihydropyrimidin-5-yl]amino}-2,3-dihydro-1H-inden-2-yl acetate

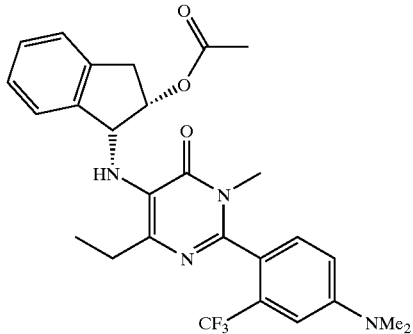

(1R,2S)-1-{[4-Methyl-2-(2,4-dichlorophenyl)-1-ethyl-6-oxo-1,6-dihydropyrimidin-5-yl]amino}-2,3-dihydro-1H-inden-2-yl acetate

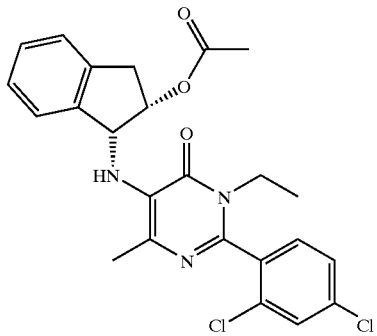

(1R,2S)-1-{[4-Methyl-2-(2-chloro-4-methoxyphenyl)-1-ethyl-6-oxo-1,6-dihydropyrimidin-5-yl]amino}-2,3-dihydro-1H-inden-2-yl acetate

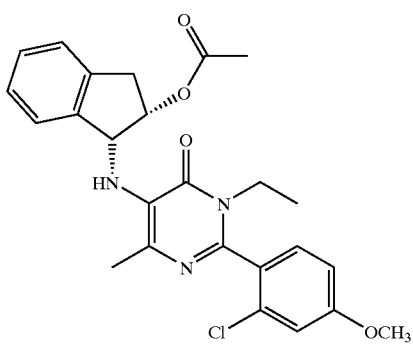

(1R,2S)-1-{[4-Methyl-2-(2-methyl-4-methoxyphenyl)-1-ethyl-6-oxo-1,6-dihydropyrimidin-5-yl]amino}-2,3-dihydro-1H-inden-2-yl acetate

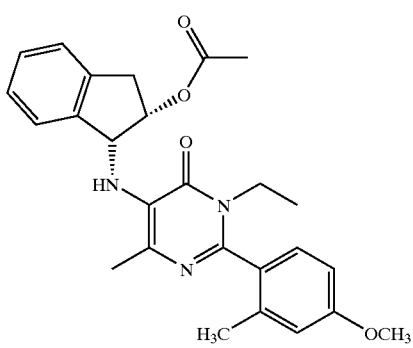

-continued (1R,2S)-1-{[4-Methyl-2-(2-chloro-4-dimethylaminophenyl)-1-ethyl-6-oxo-1,6-dihydropyrimidin-5-yl]amino}-2,3-dihydro-1H-inden-2-yl acetate

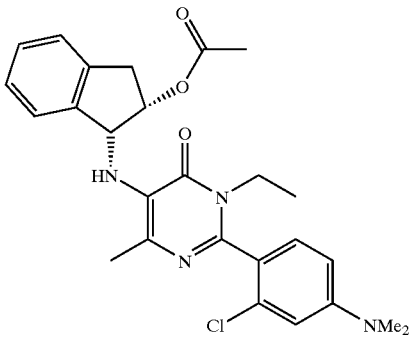

(1R,2S)-1-({2-[6-Dimethylamino)-4-methylpridin-3-yl]-4-methyl-1-ethyl-6-oxo-1,6-dihydropyrimidin-5-yl}amino)-2,3-dihydro-1H-inden-2-yl acetate

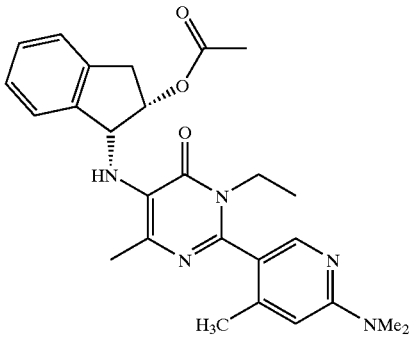

(1R,2S)-1-{[4-Methyl-2-(6-methoxy-2-methylpyridin-3-yl)-1-ethyl-6-oxo-1,6-dihydropyrimidin-5-yl]amino}-2,3-dihydro-1H-inden-2-yl acetate

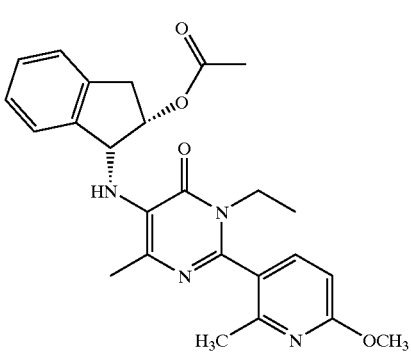

(1R,2S)-1-{[4-Methyl-2-(2-chloro-4-trifluoromethylphenyl)-1-ethyl-6-oxo-1,6-dihydropyrimidin-5-yl]amino}-2,3-dihydro-1H-inden-2-yl acetate

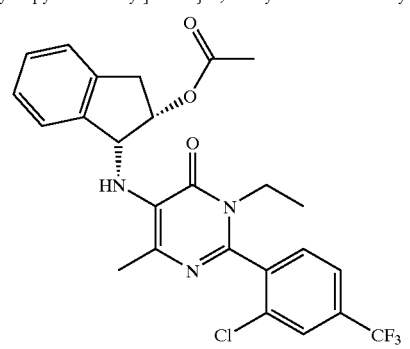

-continued (1R,2S)-1-{[4-Methyl-2(2-trifluoromethyl-4-dimethylaminophenyl)-1-ethyl-6-oxo-1,6-dihydropyrimidin-5-yl]amino}-2,3-dihydro-1H-inden-2-yl acetate

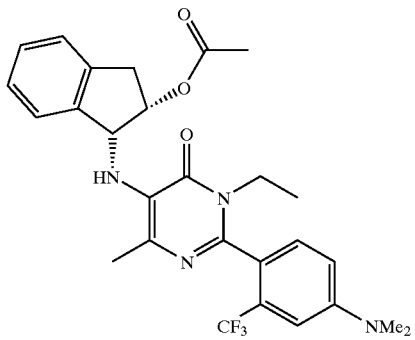

(1R,2S)-1-{[2-(2,4-Dichlorophenyl)-1-diethyl-6-oxo-1,6-dihydropyrimidin-5-yl]amino}-2,3-dihydro-1H-inden-2-yl acetate

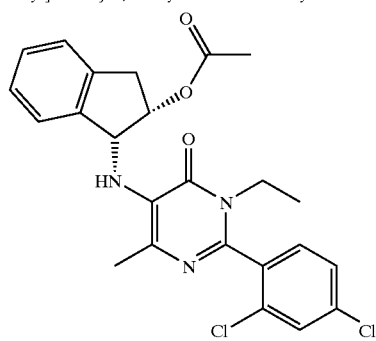

(1R,2S)-1-{[2-(2-Chloro-4-methoxyphenyl)-1,4-diethyl-6-oxo-1,6-dihydropyrimidin-5-yl]amino}-2,3-dihydro-1H-inden-2-yl acetate

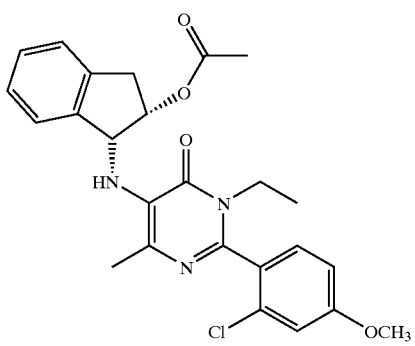

(1R,2S)-1-{[2-(2-Methyl-4-methoxyphenyl)-1,4-diethyl-6-oxo-1,6-dihydropyrimidin-5-yl]amino}-2,3-dihydro-1H-inden-2-yl acetate

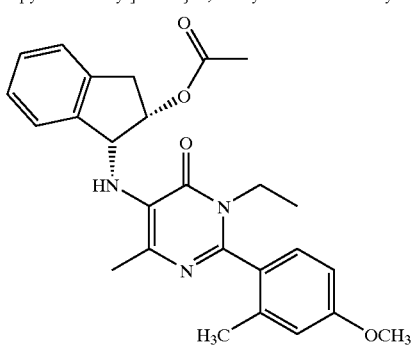

-continued (1R,2S)-1-{[2-(2-Chloro-4-dimethoxyaminophenyl)-1,4-diethyl-6-oxo-1,6-dihydropyrimidin-5-yl]amino}-2,3-dihydro-1H-inden-2-yl acetate

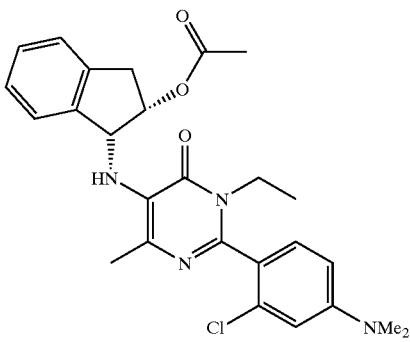

(1R,2S)-1-({2-[6-Dimethylamino)-4-methylpyridin-3-yl]-1,4-diethyl-6-oxo-1,6-dihydropyrimidin-5-yl}amino)-2,3-dihydro-1H-inden-2-yl acetate

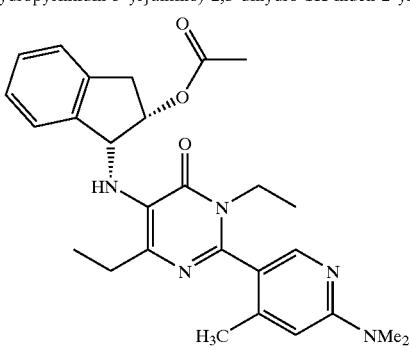

(1R,2S)-1-{[2-(6-Methoxy-2-methylpyridin-3-yl)-1,4-diethyl-6-oxo-1,6-dihydropyrimidin-5-yl]amino}-2,3-dihydro-1H-inden-2-yl acetate

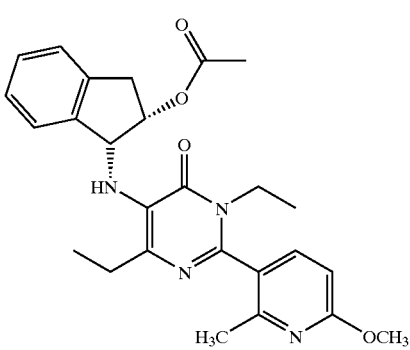

(1R,2S)-1-{[2-(2-Chloro-4-trifluoromethylphenyl)-1,4-diethyl-6-oxo-1,6-dihydropyrimidin-5-yl]amino}-2,3-dihydro-1H-inden-2-yl acetate

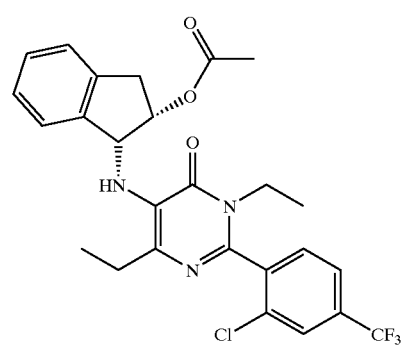

-continued (1R,2S)-1-{[2-(2-Trifluoromethyl-4-dimeythylaminophenyl)-1,4-diethyl-6-oxo-1,6-dihydropyrimidin-5-yl]amino}-2,3-dihydro-1H-inden-2-yl acetate

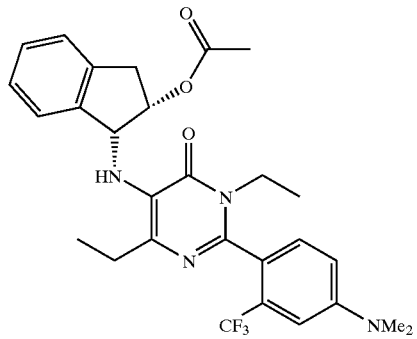

2-(2,4-Dichlorophenyl)-5-{[(1R,2S)-2-ethoxy-2,3-dihydro-1H-inden-1-yl]amino}-3,6-dimethylpyrimidin-4(3H)-one

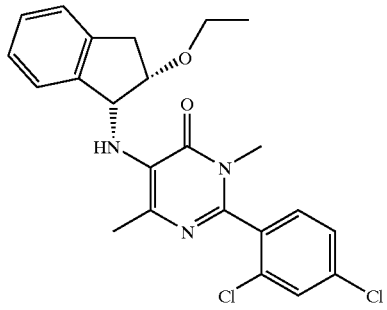

2-(2-Chloro-4-methoxyphenyl)-5-{[(1R, 2S)-2-ethoxy-2,3-dihydro-1H-inden-1-yl]amino}-3,6-dimethylpyrimidin-4(3H)-one

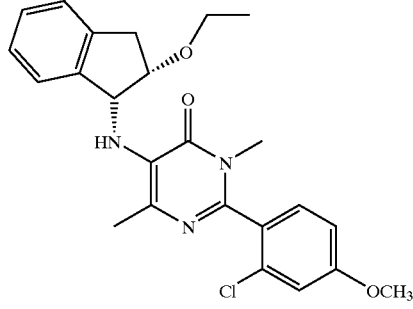

2-(2-Methyl-4-methoxyphenyl)-5-{[(1R,2S)-2-ethoxy-2,3-dihydro-1H-inden-1-yl]amino}-3,6-dimethylpyrimidin-4(3H)-one

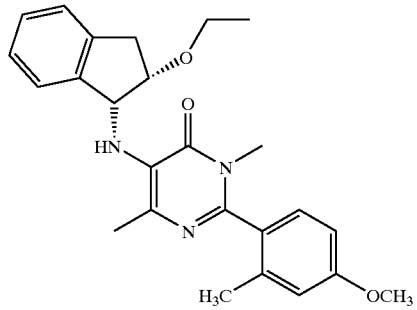

-continued 2-(2-Chloro-4-dimethylaminophenyl)-5-{[(1R,2S)-2-ethoxy-2,3-dihydro-1H-inden-1-yl]amino}-3,6-dimethylpyrimidin-4(3H)-one

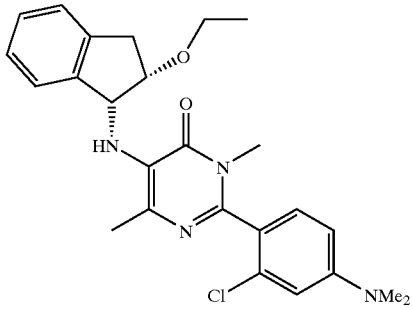

2-[6-(Dimethylamino)-4-methylpyridin-3-yl]-5-{[(1R,2S)-2-ethoxy-2,3-dihydro-1H-inden-1-yl]amino}-3,6-dimethylpyrimidin-4(3H)-one

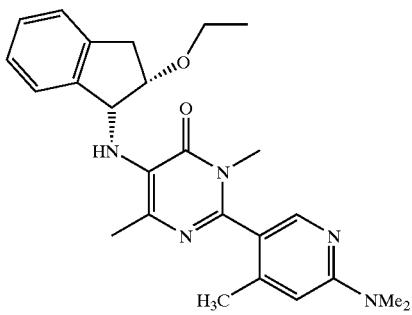

5-{[(1R,2S)-2-Ethoxy-2,3-dihydro-1H-inden-1-yl]amino}-2-(6-methoxy-2-methylpyridin-3-yl)-3,6-dimethypyrimidin-4(3H)-one

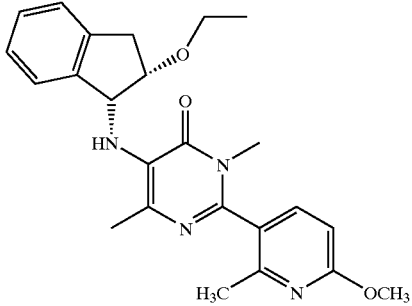

2-(2-Chloro-4-trifluoromethylphenyl)-5-{[1R,2S)-2-ethoxy-2,3-dihydro-1H-inden-1-yl]}-3,6-dimethylpyrimidin-4(3H)-one

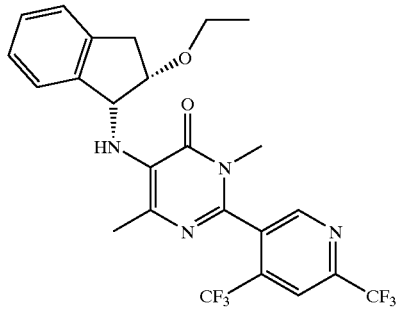

-continued 2-(2-Triflouromethyl-4-dimethylaminophenyl)-5-{[(1R,2S)-2-ethoxy-2,3-dihydro-1H-inden-1-yl]amino}-3,6-dimethylpyrimidin-4(3H)-one

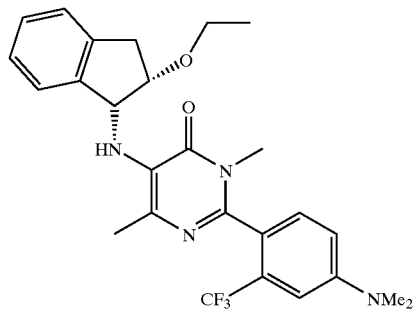

2-(2,4-Dichlorophenyl)-5-{[(1R,2S)-2-ethoxy-2,3-dihydro-1H-inden-1-yl]amino}-6-ethyl-3-methylpyrimidin-4(3H)-one

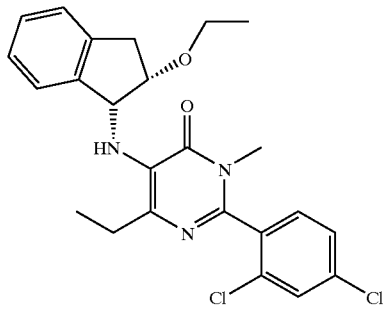

2-(2-Chloro-4-methoxyphenyl)-5-{[(1R,2S)-2-ethoxy-2,3-dihydro-1H-inden-1-yl]amino}-6-ethyl-3-methylpyrimidin-4(3H)-one

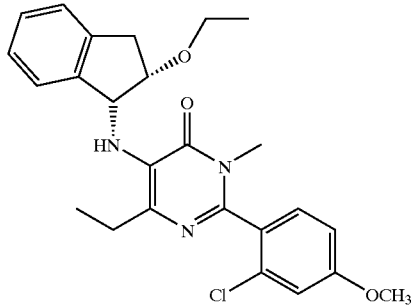

2-(2-Methyl-4-methoxyphenyl)-5-{[(1R,2S)-2-ethoxy-2,3-dihydro-1H-inden-1-yl]amino}-6-ethyl-3-methylpyrimidin-4(3H)-one

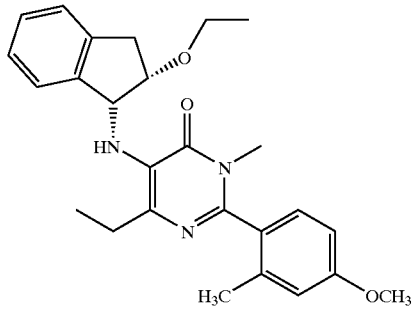

-continued 2-(2-Chloro-4-dimethylaminophenyl)-5-{[(1R,2S)-2-ethoxy-2,3-dihydro-1H-inden-1-yl]amino}-6-ethyl-3-methylpyrimidin-4(3H)-one

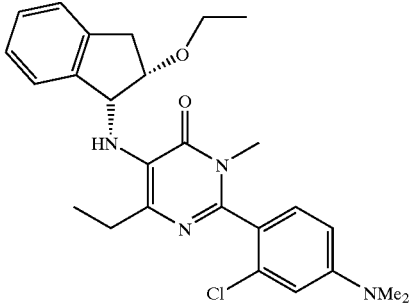

2[6-(Dimethylamino)-4-methylpyridin-3-yl]-5-{[(1R,2S)-2-ethoxy-2,3-dihydro-1H-inden-1-yl]amino}-6-ethyl-3-methylpyrimidin-4(3H)-one

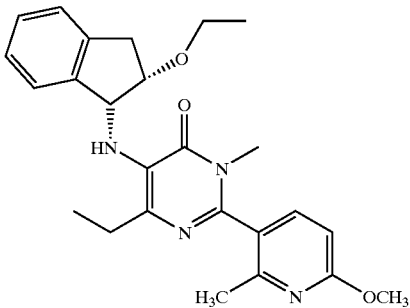

5-{[(1R,2S)-2-Ethoxy-2,3-dihydro-1H-inden-1-yl]amino}-6-ethyl-2-(6-methoxy-2-methylpyridin-3-yl)-3-methylpyrimidin-4(3H)-one

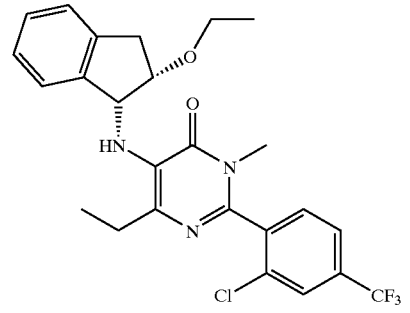

2-(2-Chloro-4-trifluoromethylphenyl)-5-{[(1R,2S)-2-ethoxy-2,3-dihydro-1H-inden-1-yl]amino}-6-ethyl-3-methylpyrimidin-4(3H)-one -continued 2-(2-Trifluoromethyl-4-dimethylaminophenyl)-5-{[(1R,2S)-2-ethoxy-2,3-dihydro-1H-inden-1-yl]amino}-6-ethyl-3-methylpyrimidin-4(3H)-one

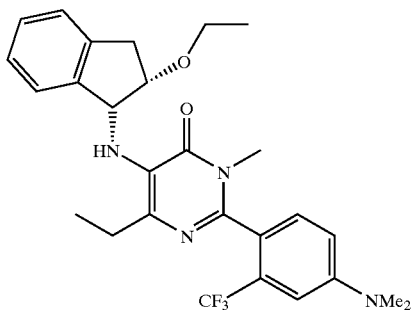

2-(2,4-Dichlorophenyl)-5-{[(1R,2S)-2-ethoxy-2,3-dihydro-1H-inden-1-yl]amino}-6-methyl-3-ethylpyrimidin-4(3H)-one

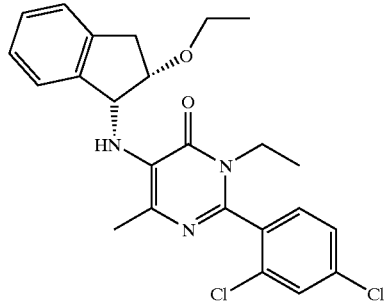

2-(2-Chloro-4-methoxyphenyl)-5-{[(1R,2S)-2-ethoxy-2,3-dihydro-1H-inden-1-yl]amino}-6-methyl-3-ethylpyrimidin-4(3H)-one

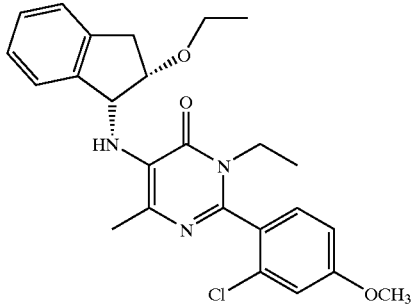

2-(2-Methyl-4-methoxyphenyl)-5-{[(1R,2S)-2-ethoxy-2,3-dihydro-1H-inden-1-yl]amino}-6-methyl-3-ethylpyrimidin-4(3H)-one

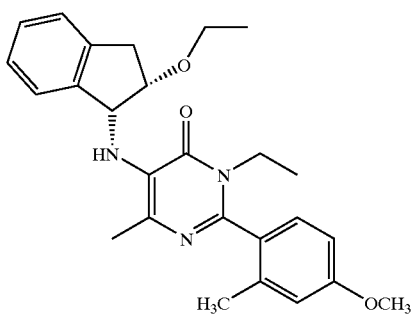

2-(2-Chloro-4-dimethylaminophenyl)-5-{[(1R,2S)-2-ethoxy-2,3-dihydro-1H-inden-1-yl]amino}-6-methyl-3-ethylpyrimidin-4(3H)-one

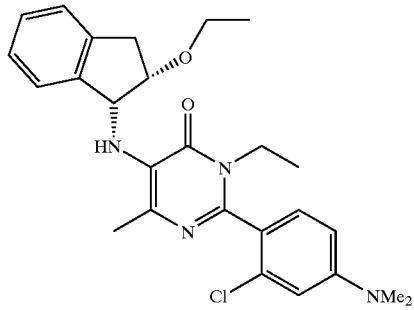

2-[6-(Dimethylamino)-4-methylpyridin-3-yl]-5-{[(1R,2S)-2-ethoxy-2,3-dihydro-1H-inden-1-yl]amino}-6-methyl-3-ethylpyrimidin-4(3H)-one

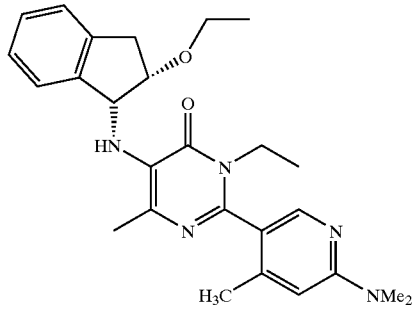

5-{[(1R,2S)-2-Ethoxy-2,3-dihydro-1H-inden-1-yl]amino}-6-methyl-2-(6-methoxy-2-methylpyridin-3-yl)-3-ethylpyrimidin-4(3H)-one

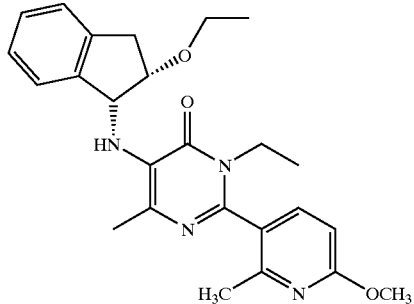

2-(2-Chloro-4-trifluoromethylphenyl)-5-{[(1R,2S)-2-ethoxy-2,3-dihydro-1H-inden-1-yl]amino}-6-methyl-3-ethylpyrimidin-4(3H)-one

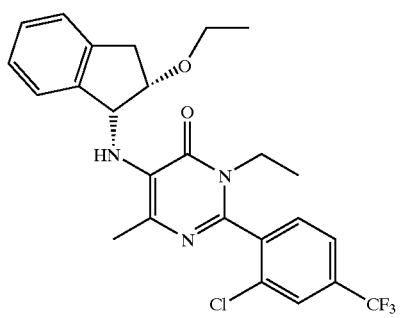

-continued 2-(2-Trifluoromethyl-4-dimethylaminophenyl)-5-{[(1R, 2S)-2-ethoxy-2, 3-dihydro-1H-inden-1-yl]amino}-6-methyl-3-ethylpyrimidin-4(3H)-one

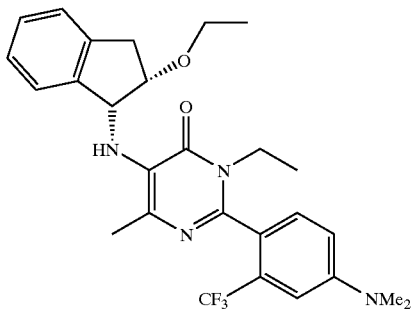

2-(2, 4-Dichlorophenyl)-5-{[(1R, 2S)-2-ethoxy-2, 3-dihydro-1H-inden-1-yl]amino}-3, 6-diethylpyrimidin-4(3H)-one

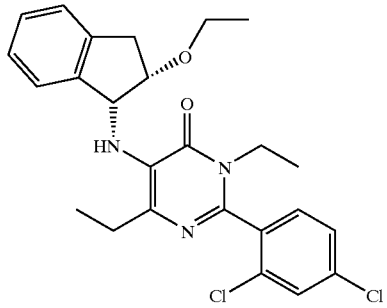

2-(2-Chloro-4-methoxyphenyl)-5-{[(1R,2S)-2-ethoxy-2,3-dihydro-1H-inden-1-yl]amino}-3,6-diethylpyrimidin-4(3H)-one

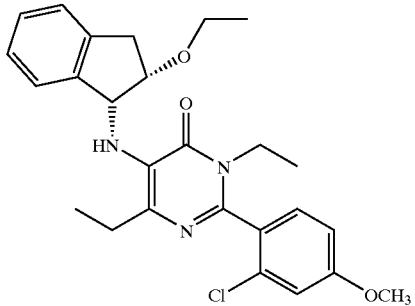

2-(2-Methyl-4-methoxyphenyl)-5-{[(1R,2S)-2-ethoxy-2,3-dihydro-1H-inden-1-yl]amino}-3,6-diethylpyrimidin-4(3H)-one

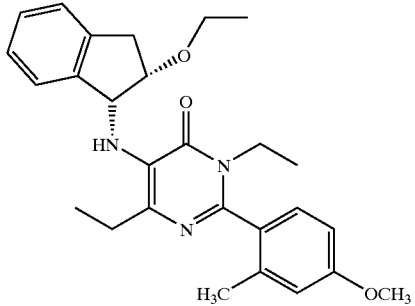

-continued 2-(2-Chloro-4-dimethylaminophenyl)-5-{[(1R,2S)-2-ethoxy-2,3-dihydro-1H-inden-1-yl]amino}-3,6-diethylpyrimidin-4(3H)-one

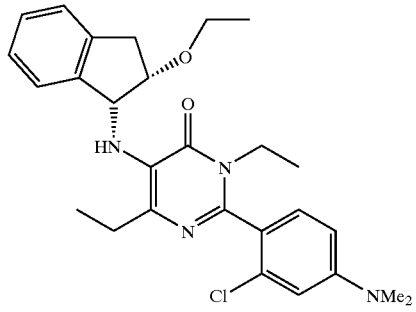

2-[6-(Dimethylamino)-4-methylpyridin-3-yl]-5-{[(1R,2S)-2-ethoxy-2,3-dihydro-1H-inden-1-yl]amino}-3,6-diethylpyrimidin-4(3H)-one

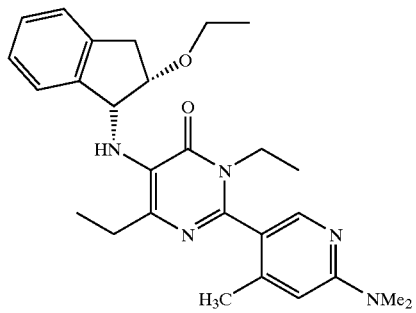

5-{[(1R,2S)-2-Ethoxy-2,3-dihydro-1H-inden-1-yl]amino}-2-(6-methoxy-2-methylpyridin-3-yl)-3,6-diethylpyrimidin-4(3H)-one

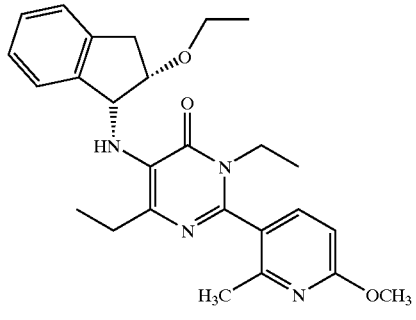

2-(2-Chloro-4-trifluoromethylphenyl)-5-{[(1R,2S)-2-ethoxy-2,3-dihydro-1H-inden-1-yl]amino}-3,6-diethylpyrimidin-4(3H)-one

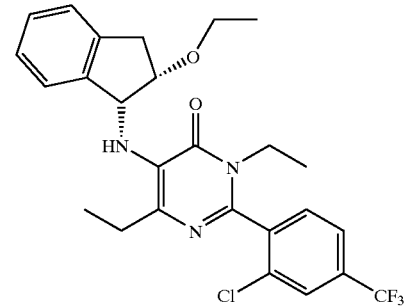

-continued 2-(2-Trifluoromethyl-4-dimethylaminophenyl)-5-{[(1R,2S)-2-ethoxy-2,3-dihydro-1H-inden-1-yl]amino}-3,6-diethylpyrimidin-4(3H)-one

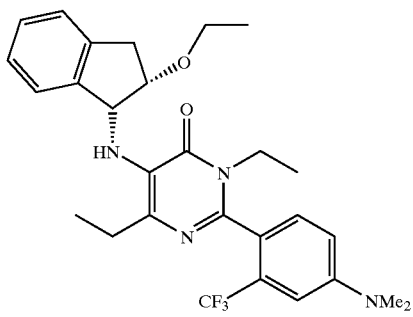

Methyl (3R,4S)-3-{[2-(2,4-dichlorophenyl)-1,4-dimethyl-6-oxo-1,6-dihydropyrimidin-5-yl]amino}-4-ethoxypyrrolidine-1-carboxylate

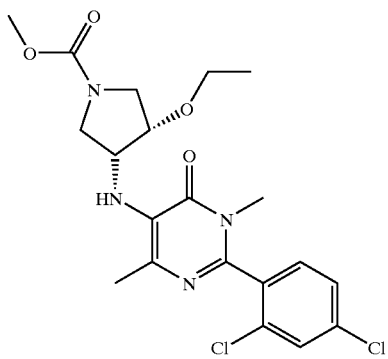

Methyl (3R,4S)-3-{[2-(2-chloro-4-methoxyphenyl)-1,4-dimethyl-6-oxo-1,6-dihydropyrimidin-5-yl]amino}-4-exthoxypyrrolidine-1-carboxylate

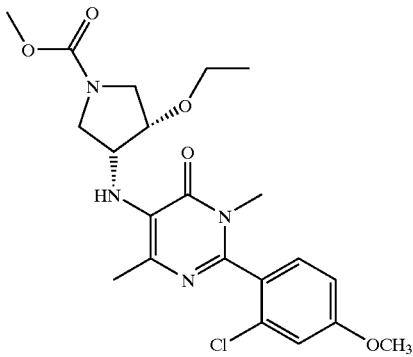

Methyl (3R,4S)-3-{[2-(2-methyl-4-methoxyphenyl)-1,4-dimethyl-6-oxo-1,6-dihydropyrimidin-5-yl]amino}-4-exthoxypyrrolidine-1-carboxylate

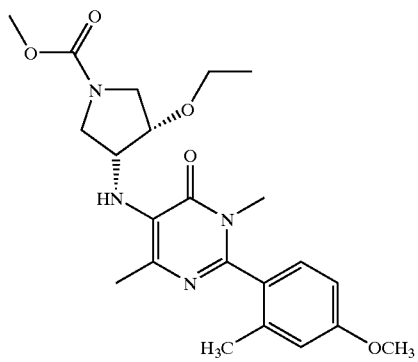

-continued

Methyl (3R,4S)-3-{[2-(2-chloro-4-dimethylaminophenyl)-1,4-dimethyl-6-oxo-1,6-dihydropyrimidin-5-yl]amino}-4-exthoxypyrrolidine-1-carboxylate

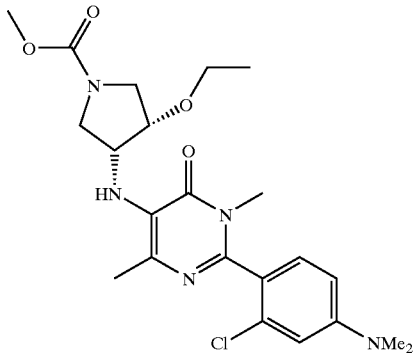

Methyl (3R,4S)-3-({[2-[6-(dimethylamino)-4-methylpyridin-3-yl]-1,4-dimethyl-6-oxo-1,6-dihydropyrimidin-5-yl}amino)-4-exthoxypyrrolidine-1-carboxylate

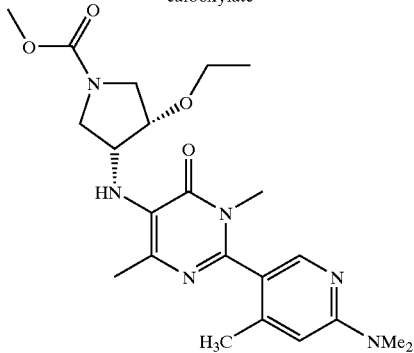

Methyl (3R,4S)-3-ethoxy-4-{[2-(6-methoxy-2-methylpyridin-3-yl)-1,4-dimethyl-6-oxo-1,6-dihydropyrimidin-5-yl]amino}-4-exthoxypyrrolidine-1-carboxylate

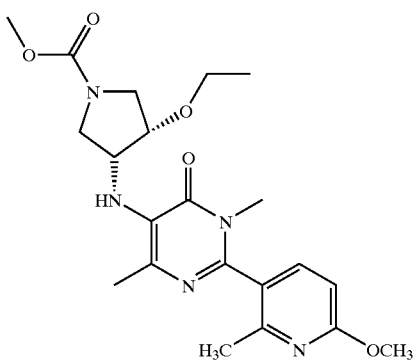

Methyl (3R,4S)-3-{[2-(2-chloro-4-trifluoromethylphenyl)-1,4-dimethyl-6-oxo-1,6-dihydropyrimidin-5-yl]amino}-4-exthoxypyrrolidine-1-carboxylate

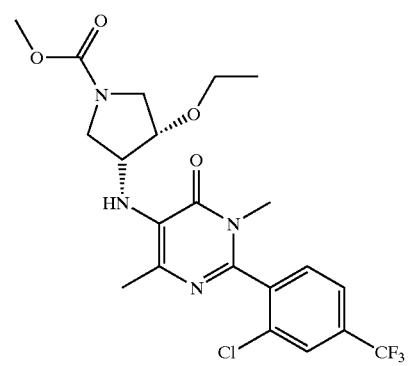

-continued

Methyl (3R,4S)-3-{[2-(2-trifluoromethyl-4-dimethylaminophenyl)-1,4-dimethyl-6-oxo-1,6-dihydropyrimidin-5-yl]amino}-4-exthoxypyrrolidine-1-carboxylate

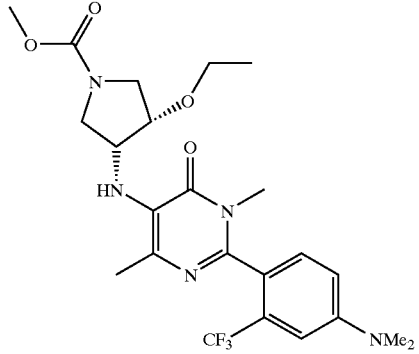

Methyl (3R,4S)-3-{[2-(2,4-dichlorophenyl)-1,4-ethyl-1-methyl-6-oxo-1,6-dihydropyrimidin-5-yl]amino}-4-exthoxypyrrolidine-1-carboxylate

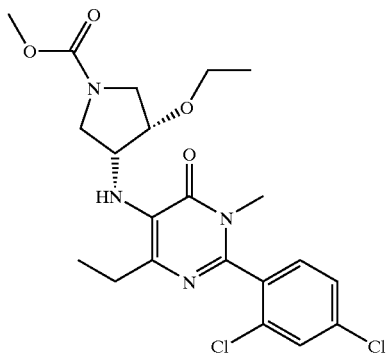

Methyl (3R,4S)-3-{[2-(2-chloro-4-methoxyphenyl)-4-ethyl-1-methyl-6-oxo-1,6-dihydropyrimidin-5-yl]amino}-4-exthoxypyrrolidine-1-carboxylate

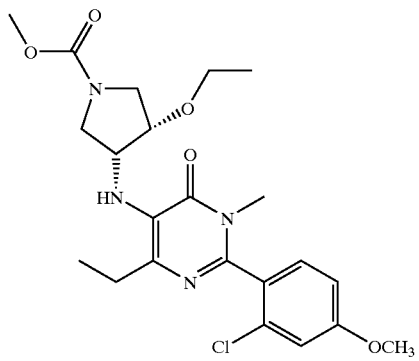

Methyl (3R,4S)-3-{[2-(2-methyl-4-methoxyphenyl)-4-ethyl-1-methyl-6-oxo-1,6-dihydropyrimidin-5-yl]amino}-4-exthoxypyrrolidine-1-carboxylate

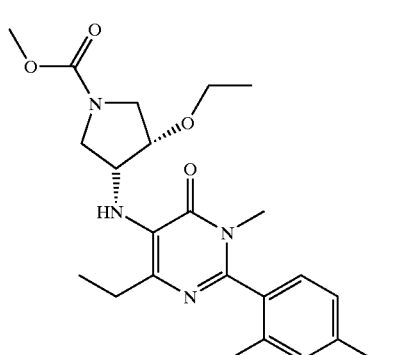

-continued

Methyl (3R,4S)-3-{[2-(2-chloro-4-dimethylaminophenyl)-4-ethyl-1-methyl-6-oxo-1,6-dihydropyrimidin-5-yl]amino}-4-exthoxypyrrolidine-1-carboxylate

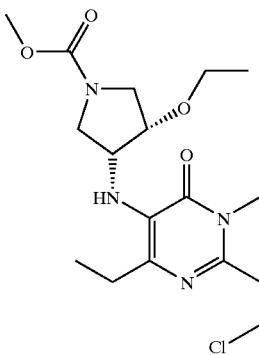

Methyl (3R,4S)-3-({2-[6-(dimethylamino)-4-methylpyridin-3-yl]-4-ethyl-1-methyl-6-oxo-1,6-dihydropyrimidin-5-yl}amino)-4-exthoxypyrrolidine-1-carboxylate

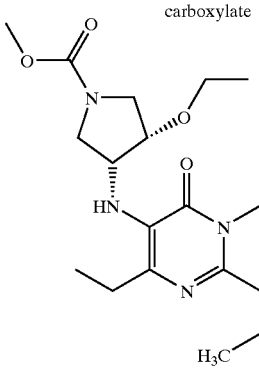

Methyl (3S,4R)-3-ethoxy-4-{[4-ethyl-2-(6-methoxy-2-methylpyridin-3-yl)-1-methyl-6-oxo-1,6-dihydropyrimidin-5-yl]amino}pyrrolidine-1-carboxylate

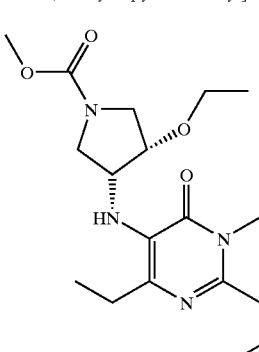

Methyl (3R,4S)-3-{[2-(2-chloro-4-trifluoromethylphenyl)-4-ethyl-1-methyl-6-oxo-1,6-dihydropyrimidin-5-yl]amino}-4-ethoxypyrrolidine-1-carboxylate

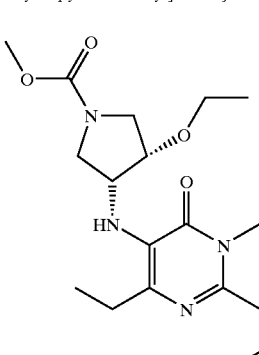

-continued

Methyl (3R,4S)-3-{[2-(2-trifluoromethyl-4-dimethylaminophenyl)-4-ethyl-1-methyl-6-oxo-1,6-dihydropyrimidin-5-yl]amino}-4-ethoxypyrrolidine-1-carboxylate

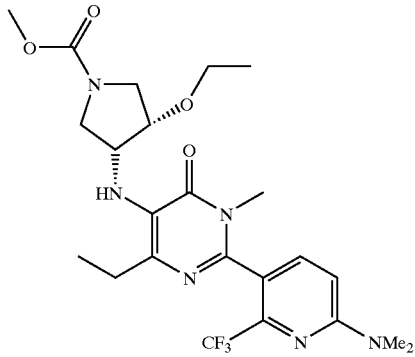

Methyl (3R,4S)-3-{[2-(2, 4-dichlorophenyl)-1-ethyl-4-methyl-6-oxo-1,6-dihydropyrimidin-5-yl]amino}-4-ethoxypyrrolidine-1-carboxylate

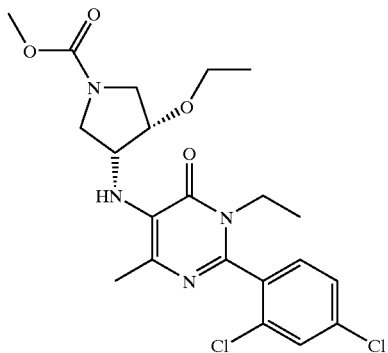

Methyl (3R,4S)-3-{[2-(2-chloro-4-methoxyphenyl)-1-ethyl-4-methyl-6-oxo-1,6-dihydropyrimidin-5-yl]amino}-4-exthoxypyrrolidine-1-carboxylate

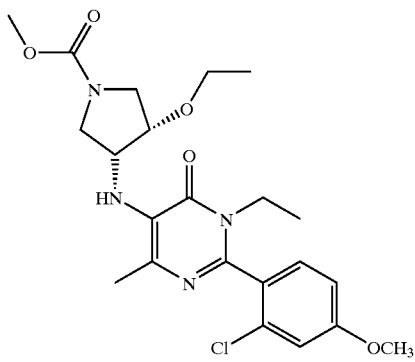

Methyl (3R,4S)-3-{[2-(2-methyl-4-methoxyphenyl)-1-ethyl-4-methyl-6-oxo-1,6-dihydropyrimidin-5-yl]amino}-4-exthoxypyrrolidine-1-carboxylate

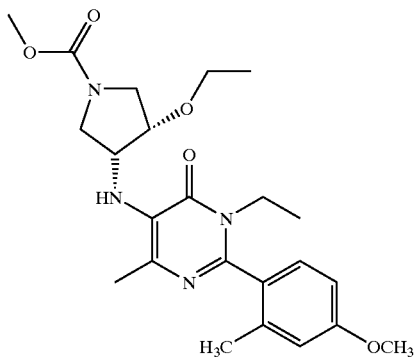

-continued

Methyl (3R,4S)-3-{[2-(2-chloro-4-dimethylaminophenyl)-1-ethyl-4-methyl-6-oxo-1,6-dihydropyrimidin-5-yl]amino}-4-exthoxypyrrolidine-1-carboxylate

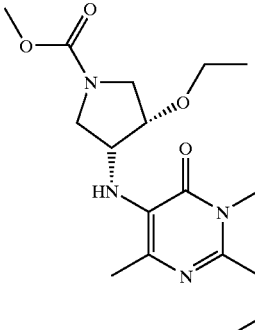

Methyl (3R,4S)-3-({[2-[6-(dimethylamino)-4-methylpyridin-3-yl]-1-ethyl-4-methyl-6-oxo-1,6-dihydropyrimidin-5-yl]amino)-4-exthoxypyrrolidine-1-carboxylate

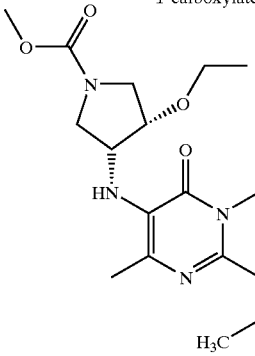

Methyl (3S,4R)-3-ethoxy-4-{[1-ethyl-2-(6-methoxy-2-methylpyridin-3-yl)-4-methyl-6-oxo-1,6-dihydropyrimidin-5-yl]amino}pyrrolidine-1-carboxylate

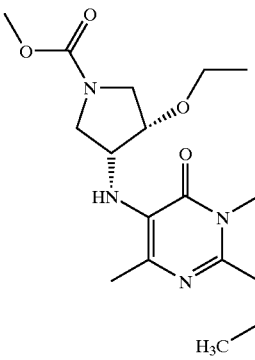

Methyl (3R,4S)-3-({[2-[2-chloro-4-trifluoromethylphenyl)-1-ethyl-4-methyl-6-oxo-1,6-dihydropyrimidin-5-yl]amino}-4-exthoxypyrrolidine-1-carboxylate

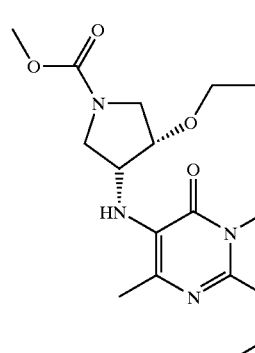

-continued

Methyl (3R,4S)-3-{[2-(2-trifluoromethyl-4-dimethylaminophenyl)-1-ethyl-4-methyl-6-oxo-1,6-dihydropyrimidin-5-yl]amino}-4-exthoxypyrrolidine-1-carboxylate

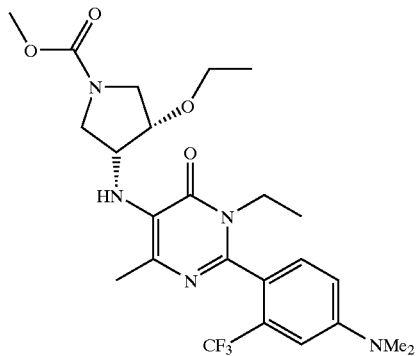

Methyl (3R,4S)-3-{[2-(2, 4-dichlorophenyl)-1,4-diethyl-6-oxo-1,6-dihydropyrimidin-5-yl]amino}-4-exthoxypyrrolidine-1-carboxylate

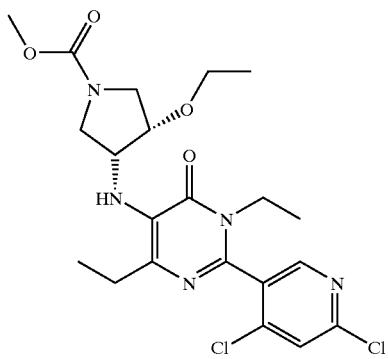

Methyl (3R,4S)-3-{[2-(2-chloro-4-methoxyphenyl)-1,4-diethyl-6-oxo-1,6-dihydropyrimidin-5-yl]amino}-4-ethoxypyrrolidine-1-carboxylate

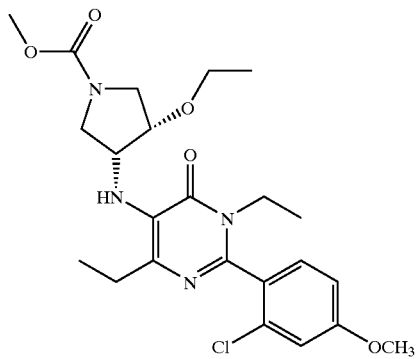

Methyl (3R,4S)-3-{[2-(2-methyl-4-methoxyphenyl)-1,4-diethyl-6-oxo-1,6-dihydropyrimidin-5-yl]amino}-4-exthoxypyrrolidine-1-carboxylate

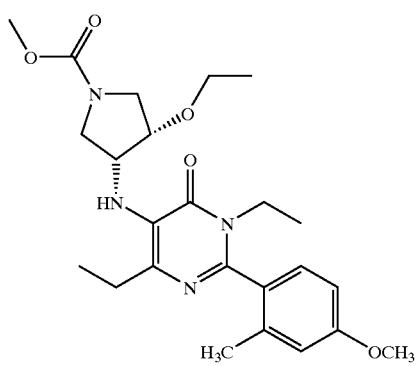

-continued

Methyl (3R,4S)-3-{[2-(2-chloro-4-dimethylaminophenyl)-1,4-diethylmethyl-6-oxo-1,6-dihydropyrimidin-5-yl]amino}-4-ethoxypyrrolidine-1-carboxylate

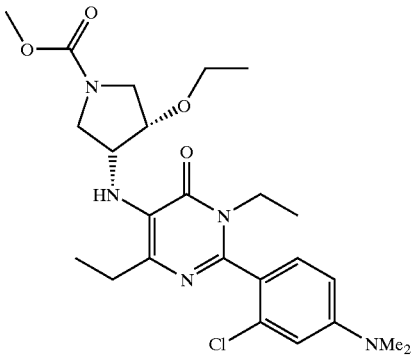

Methyl (3R,4S)-3-({2-[6-dimethylamino)-4-methylpyridin-3-yl]-1,4-diethyl-6-oxo-1,6-dihydropyrimidin-5-yl}amino)-4-exthoxypyrrolidine-1-carboxylate

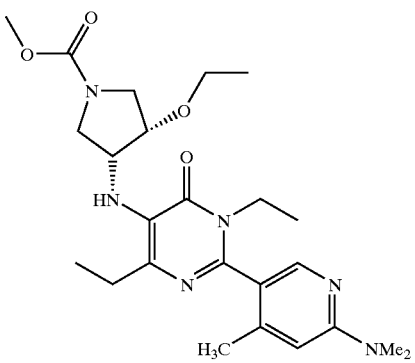

Methyl (3S,4R)-3-ethoxy-4-{[2-(6-methoxy-2-methoxypyridin-3-yl)-1,4-diethyl-6-oxo-1,6-dihydropyrimidin-5-yl]amino}pyrrolidine-1-carboxylate

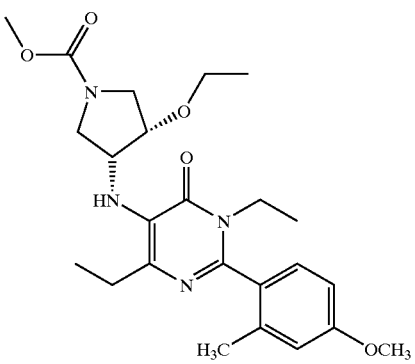

Methyl (3R,4S)-3-{[2-(2-chloro-4-trifluoromethylphenyl)-1,4-diethyl-6-oxo-1,6-dihydropyrimidin-5-yl]amino}-4-exthoxypyrrolidine-1-carboxylate

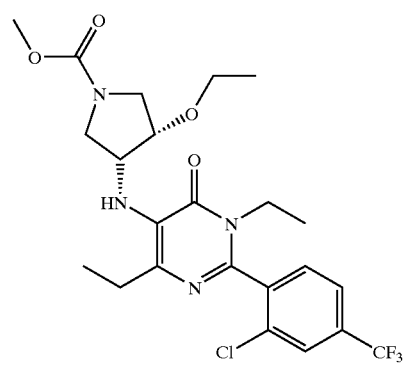

-continued

Methyl (3R,4S)-3-{[2-(2-trifluoromethyl-4-dimethylaminophenyl)-1,4-diethylmethyl-6-oxo-1,6-dihydropyrimidin-5-yl]amino}-4-ethoxypyrrolidine-1-carboxylate

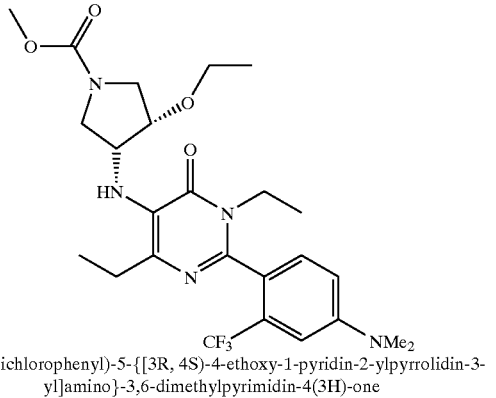

2-(2,4-Dichlorophenyl)-5-{[(3R, 4S)-4-ethoxy-1-pyridin-2-ylpyrrolidin-3-yl]amino}-3,6-dimethylpyrimidin-4(3H)-one

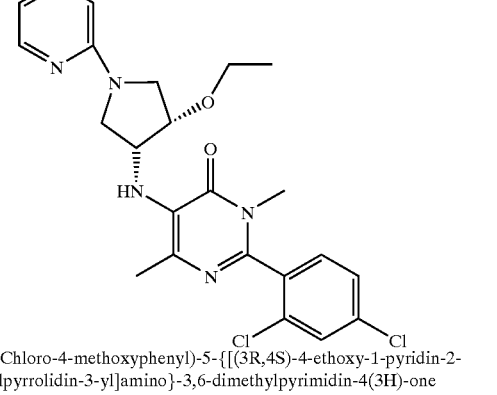

2-(2-Chloro-4-methoxyphenyl)-5-{[(3R,4S)-4-ethoxy-1-pyridin-2-ylpyrrolidin-3-yl]amino}-3,6-dimethylpyrimidin-4(3H)-one

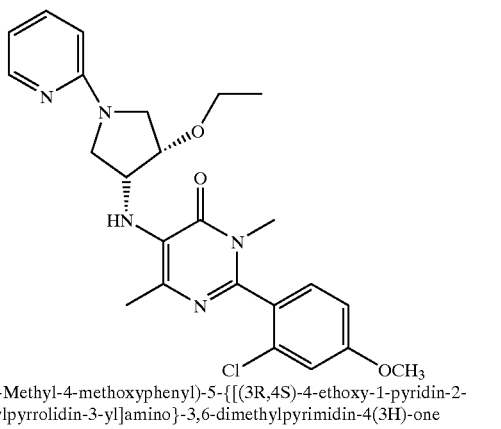

2-(2-Methyl-4-methoxyphenyl)-5-{[(3R,4S)-4-ethoxy-1-pyridin-2-ylpyrrolidin-3-yl]amino}-3,6-dimethylpyrimidin-4(3H)-one

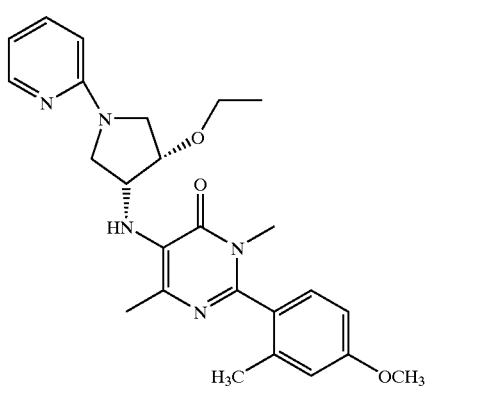

-continued 2-(2-Chloro-4-dimethylaminophenyl)-5-{[(3R,4S)-4-ethoxy-1-pyridin-2-ylpyrrolidin-3-yl]amino}-3,6-dimethylpyrimidin-4(3H)-one

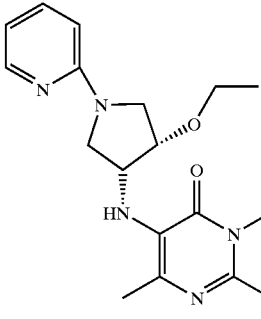

2-[6-(Dimethylamino)-4-methylpyridin-3-yl]-5-{[(3R,4S)-4-ethoxy-1-pyridin-2-ylpyrrolidin-3-yl]amino}-3,6-dimethylpyrimidin-4(3H)-one

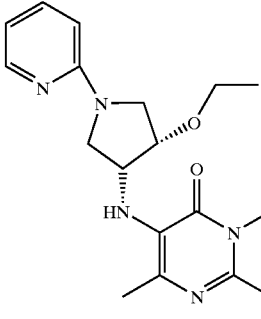

5-{[(3R,4S)-4-Ethoxy-1-pyridin-2-ylpyrrolidin-3-yl]amino}-2-(6-methoxy-2-methylpyridin-3-yl)-3,6-dimethylpyrimidin-4(3H)-one

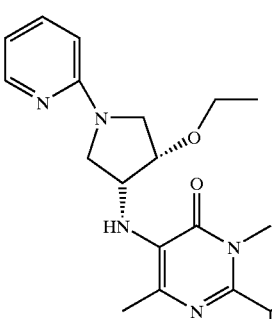

2-(2-Chloro-4-trifluoromethylphenyl)-5-{[(3R,4S)-4-ethoxy-1-pyridin-2-ylpyrrolidin-3-yl]amino}-3,6-dimethylpyrimidin-4(3H)-one

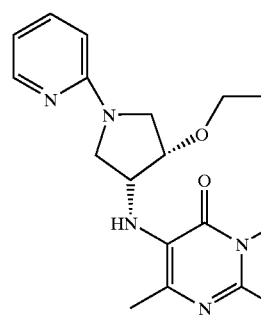

-continued 2-(2-Trifluoromethyl-4-dimethylaminophenyl)-5-{[(3R,4S)-4-ethoxy-1-pyridin-2-ylpyrrolidin-3-yl]amino}-3,6-dimethylpyrimidin-4(3H)-one

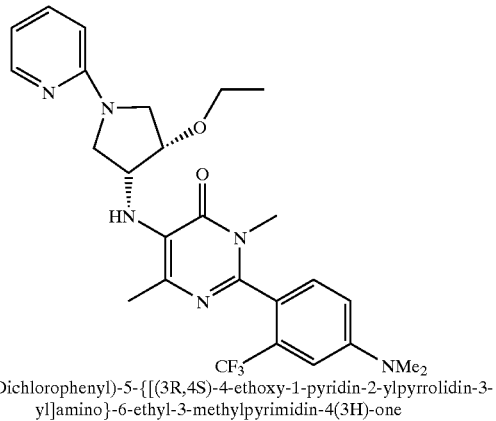

2-(2,4-Dichlorophenyl)-5-{[(3R,4S)-4-ethoxy-1-pyridin-2-ylpyrrolidin-3-yl]amino}-6-ethyl-3-methylpyrimidin-4(3H)-one

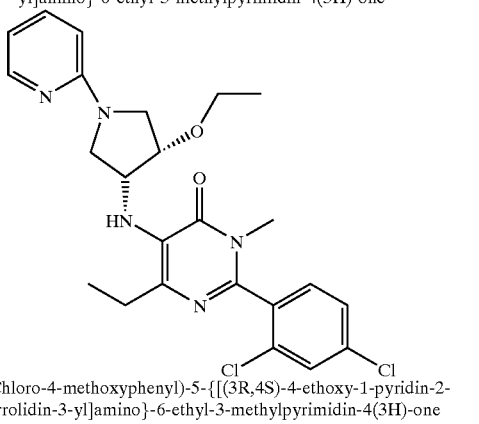

2-(2-Chloro-4-methoxyphenyl)-5-{[(3R,4S)-4-ethoxy-1-pyridin-2-ylpyrrolidin-3-yl]amino}-6-ethyl-3-methylpyrimidin-4(3H)-one

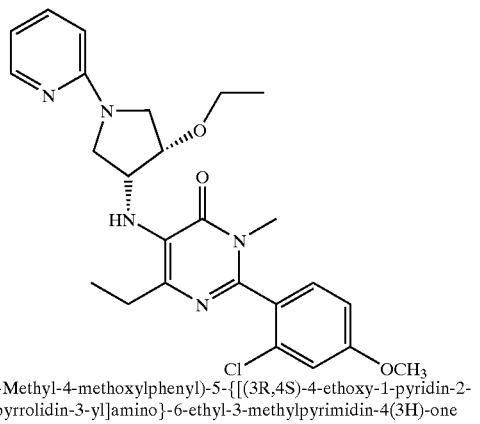

2-(2-Methyl-4-methoxylphenyl)-5-{[(3R,4S)-4-ethoxy-1-pyridin-2-ylpyrrolidin-3-yl]amino}-6-ethyl-3-methylpyrimidin-4(3H)-one

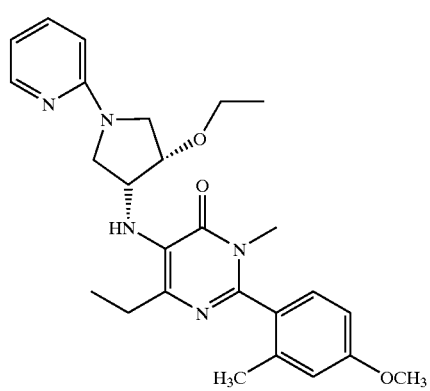

-continued 2-(2-Chloro-4-dimethylaminophenyl)-5-{[(3R,4S)-4-ethoxy-1-pyridin-2-ylpyrrolidin-3-yl]amino}6-ethyl-3-methylpyrimidin-4(3H)-one

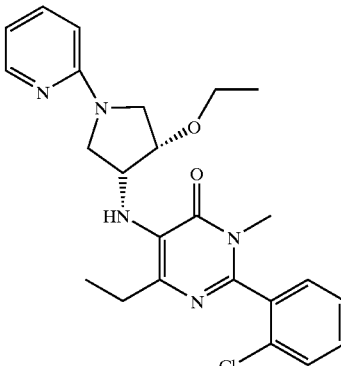

2-[6-Dimethylamino)-4-methylpyridin-3-yl]-5-{[(3R,4S)-4-ethoxy-1-pyridin-2-ylpyrrolidin-3-yl]amino}-6-ethyl-3-methylpyrimidin-4(3H)-one

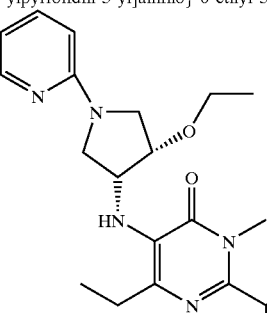

5-{[(3R,4S)-4-Ethoxy-1-pyridin-2-ylpyrrolidin-3-yl]amino}-6-ethyl-2-(6-methoxy-2-methylpyridin-3-yl)-3-methylpyrimidin-4(3H)-one

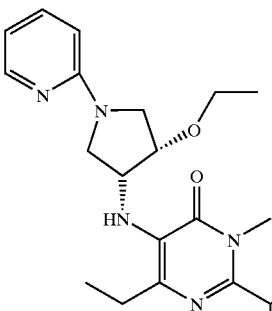

2-(2-Chloro-4-trifluoromethylphenyl)-5-{[(3R,4S)-4-ethoxy-1-pyridin-2-ylpyrrolidin-3-yl]amino}-6-ethyl-3-methylpyrimidin-4(3H)-one

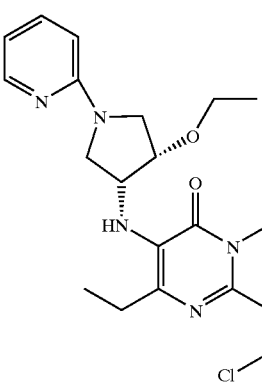

-continued 2-(2-Trifluoromethyl-4-dimethylaminophenyl)-5-{[(3R,4S)-4-ethoxy-1-pyridin-2-ylpyrrolidin-3-yl]amino}6-ethyl-3-methylpyrimidin-4(3H)-one 2-(2,4-Dichlorophenyl)-5-{[(3R, 4S)-4-ethoxy-1-pyridin-2-ylpyrrolidin-3-yl]amino}-3-ethyl-6-methylpyrimidin-4(3H)-one 2-(2-Chloro-4-methoxyphenyl)-5-{[(3R,4S)-4-ethoxy-1-pyridin-2-ylpyrrolidin-3-yl]amino}-3-ethyl-6-methylpyrimidin-4(3H)-one 2-(2-Methyl-4-methoxyphenyl)-5-{[(3R,4S)-4-ethoxy-1-pyridin-2-ylpyrrolidin-3-yl]amino}-3-ethyl-6-methylpyrimidin-4(3H)-one

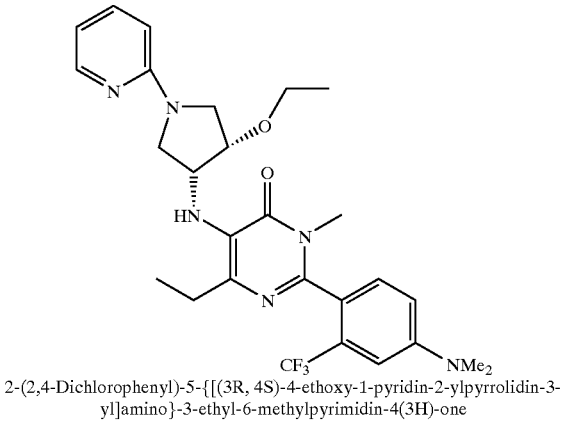

-continued 2-(2-Chloro-4-dimethylaminophenyl)-5-{[(3R,4S)-4-ethoxy-1-pyridin-2-ylpyrrolidin-3-yl]amino}-3-ethyl-6-methylpyrimidin-4(3H)-one 2-[6-(Dimethylamino)-4-methylpyridin-3-yl]-5-{[(3R,4S)-4-ethoxy-1-pyridin-2-ylpyrrolidin-3-yl]amino}-3-ethyl-6-methylpyrimidin-4(3H)-one 5-{[(3R,4S)-4-Ethoxy-1-pyridin-2-ylpyrrolidin-3-yl]amino}-3-ethyl-2-(6-methylpyridin-3-yl)-6-methylpyrimidin-4(3H)-one 2-(2-Chloro-4-trifluoromethylphenyl)-5-{[(3R,4S)-4-ethoxy-1-pyridin-2-ylpyrrolidin-3-yl]amino}-3-ethyl-6-methylpyrimidin-4(3H)-one

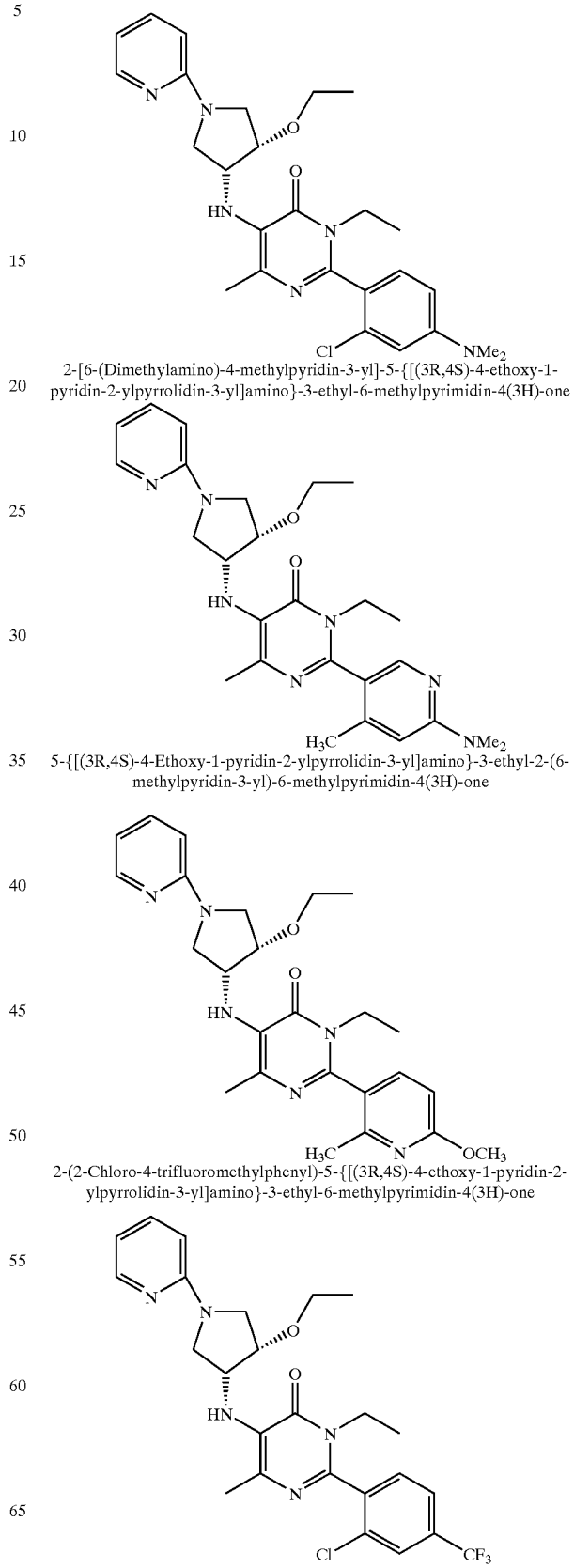

-continued 2-(2-trifluoromethyl-4-dimethylaminophenyl)-5-{[(3R,4S)-4-ethoxy-1-pyridin-2-ylpyrrolidin-3-yl]amino}-3-ethyl-6-methylpyrimidin-4(3H)-one

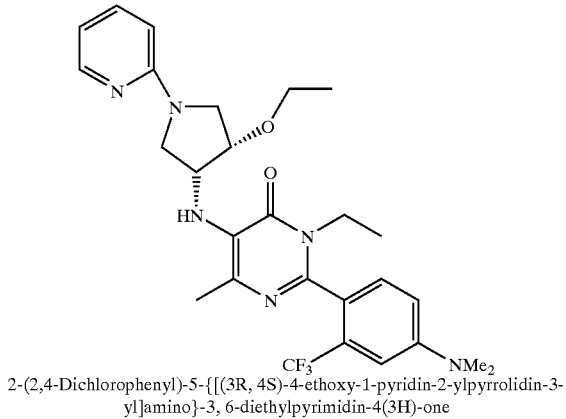

2-(2,4-Dichlorophenyl)-5-{[(3R, 4S)-4-ethoxy-1-pyridin-2-ylpyrrolidin-3-yl]amino}-3, 6-diethylpyrimidin-4(3H)-one

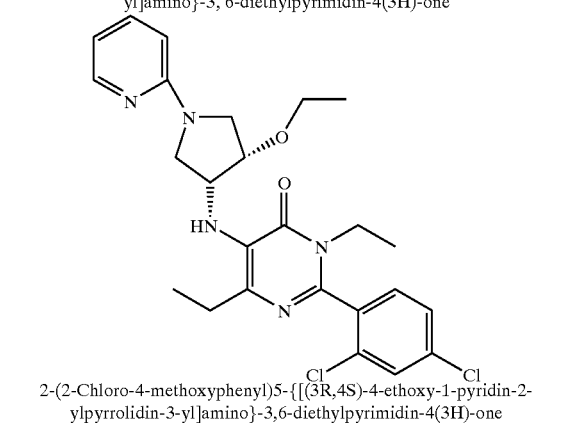

2-(2-Chloro-4-methoxyphenyl)5-{[(3R,4S)-4-ethoxy-1-pyridin-2-ylpyrrolidin-3-yl]amino}-3,6-diethylpyrimidin-4(3H)-one

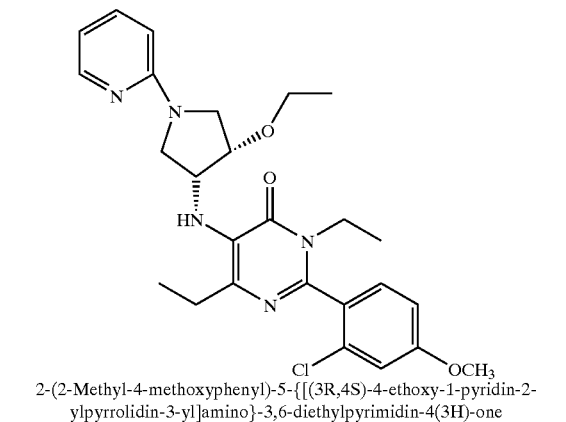

2-(2-Methyl-4-methoxyphenyl)-5-{[(3R,4S)-4-ethoxy-1-pyridin-2-ylpyrrolidin-3-yl]amino}-3,6-diethylpyrimidin-4(3H)-one

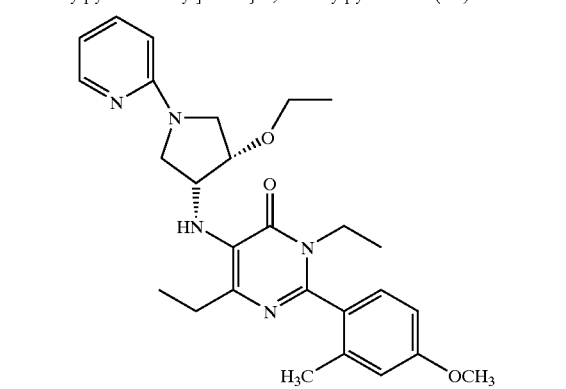

-continued 2-(2-Chloro-4-dimethylaminophenyl)-5-{[(3R,4S)-4-ethoxy-1-pyridin-2-ylpyrrolidin-3-yl]amino}-3,6-diethylpyrimidin-4(3H)-one

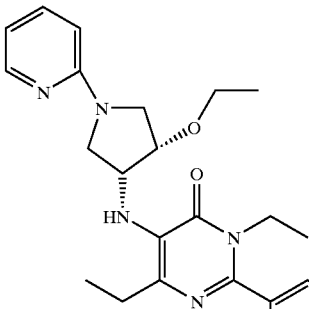

2-[6-(Dimethylamino)-4-methylpyridin-3-yl]-5-{[(3R,4S)-4-ethoxy-1-pyridin-2-ylpyrrolidin-3-yl]amino}-3,6-diethylpyrimidin-4(3H)-one

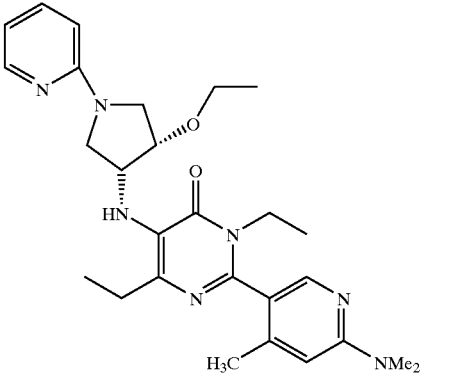

5-{[(3R,4S)-4-Ethoxy-1-pyridin-2-ylpyrrolidin-3-yl]amino}-2-(6-methoxy-2-methylpyridin-3-yl)-3,6-diethylpyrimidin-4(3H)-one

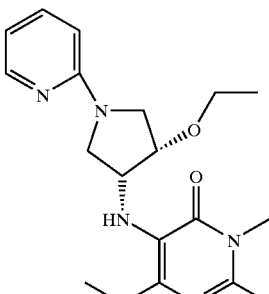

2-(2-Chloro-4-trifluoromethylphenyl)-5-{[(3R,4S)-4-ethoxy-1-pyridin-2-ylpyrrolidin-3-yl]amino}-3,6-diethylpyrimidin-4(3H)-one

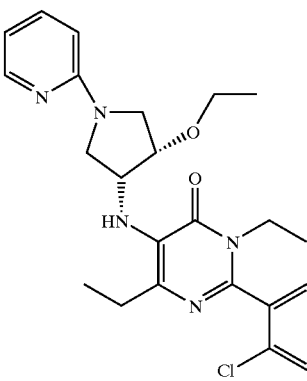

-continued 2-(2-Trifluoromethyl-4-dimethylaminophenyl)-5-{[(3R,4S)-4-ethoxy-1-pyridin-2-ylpyrrolidin-3-yl]amino}-3,6-diethylpyrimidin-4(3H)-one

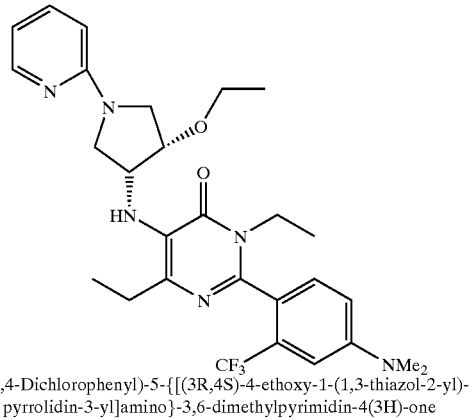

2-(2,4-Dichlorophenyl)-5-{[(3R,4S)-4-ethoxy-1-(1,3-thiazol-2-yl)-pyrrolidin-3-yl]amino}-3,6-dimethylpyrimidin-4(3H)-one

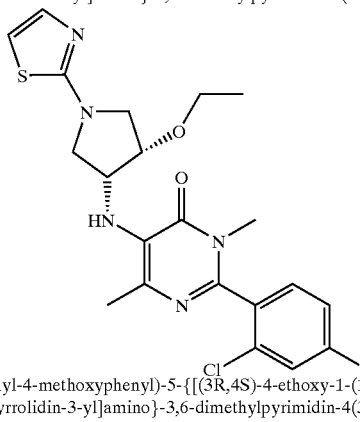

2-(2-Methyl-4-methoxyphenyl)-5-{[(3R,4S)-4-ethoxy-1-(1,3-thiazol-2-yl)pyrrolidin-3-yl]amino}-3,6-dimethylpyrimidin-4(3H)-one

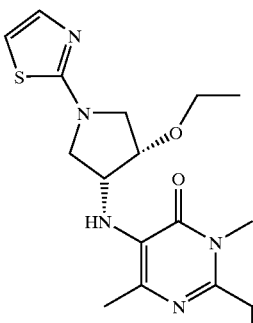

2-(2-Methyl-4-methoxyphenyl)-5-{[(3R,4S)-4-ethoxy-1-(1,3-thiazol-2-yl)pyrrolidin-3-yl]amino}-3,6-dimethylpyrimidin-4(3H)-one

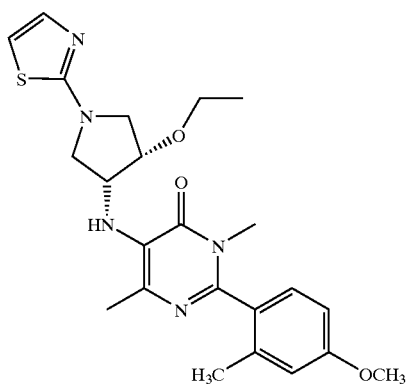

-continued 2-(2-Chloro-4-dimethylaminophenyl)-5-{[(3R,4S)-4-ethoxy-1-(1,3-thiazol-2-yl)pyrrolidin-3-yl]amino}-3,6-dimethylpyrimidin-4(3H)-one

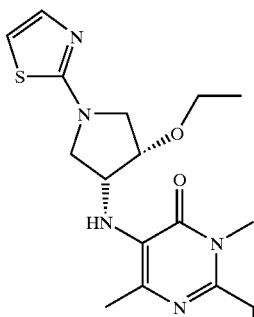

2-[6-Dimethylamino)-4-methypyridin-3-yl]-5-{[(3R,4S)-4-ethoxy-1-(1,3-thiazol-2-yl)pyrrolidin-3-yl]amino}-3,6-dimethylpyrimidin-4(3H)-one

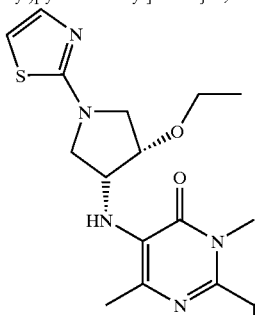

5-{[(3R,4S)-4-Ethoxy-1-(1,3-thiazol-2-yl)pyrrolidin-3-yl]amino}-2-(6-methoxy-2-methylpyridin-3-yl)-3,6-dimethylpyrimidin-4(3H)-one

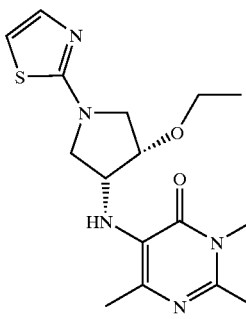

2-(2-Chloro-4-trifluoromethylphenyl)-5-{[(3R,4S)-4-ethoxy-1-(1,3-thiazol-2-yl)pyrrolidin-3-yl]amino}-3,6-dimethylpyrimidin-4(3H)-one

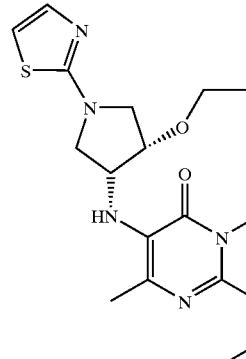

-continued 2-(2-Trifluoromethyl-4-dimethylaminophenyl)-5-{[(3R,4S)-4-ethoxy-1-(1,3-thiazol-2-yl)pyrrolidin-3-yl]amino}-3,6-dimethylpyrimidin-4(3H)-one

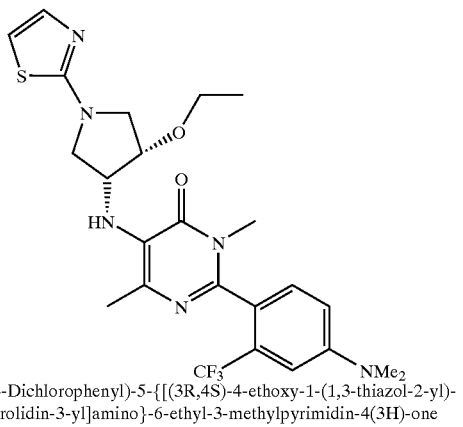

2-(2,4-Dichlorophenyl)-5-{[(3R,4S)-4-ethoxy-1-(1,3-thiazol-2-yl)-pyrrolidin-3-yl]amino}-6-ethyl-3-methylpyrimidin-4(3H)-one

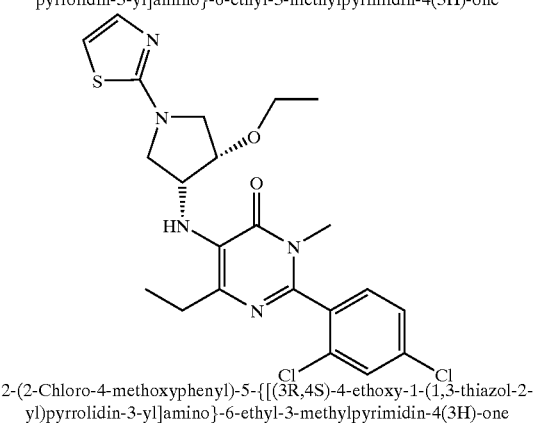

2-(2-Chloro-4-methoxyphenyl)-5-{[(3R,4S)-4-ethoxy-1-(1,3-thiazol-2-yl)pyrrolidin-3-yl]amino}-6-ethyl-3-methylpyrimidin-4(3H)-one

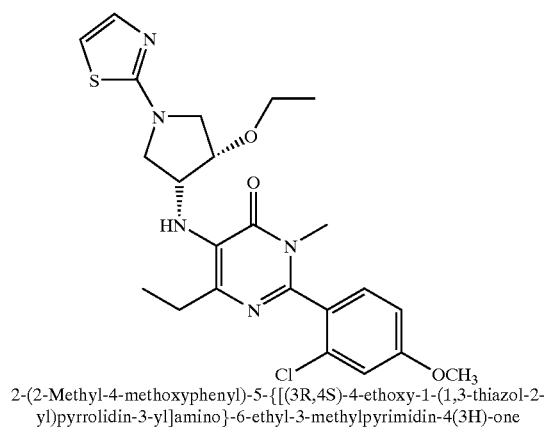

2-(2-Methyl-4-methoxyphenyl)-5-{[(3R,4S)-4-ethoxy-1-(1,3-thiazol-2-yl)pyrrolidin-3-yl]amino}-6-ethyl-3-methylpyrimidin-4(3H)-one

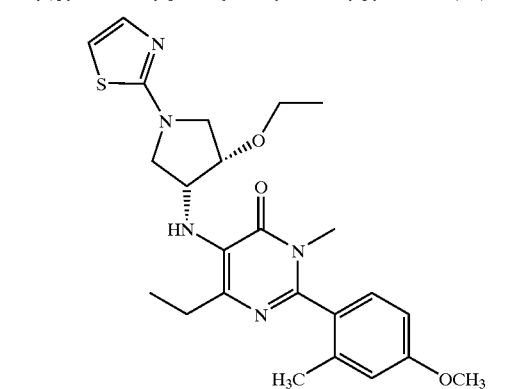

-continued 2-(2-Chloro-4-dimethylaminophenyl)-5-{[(3R,4S)-4-ethoxy-1-(1,3-thiazol-2-yl)pyrrolidin-3-yl]amino}-6-ethyl-3-methylpyrimidin-4(3H)-one

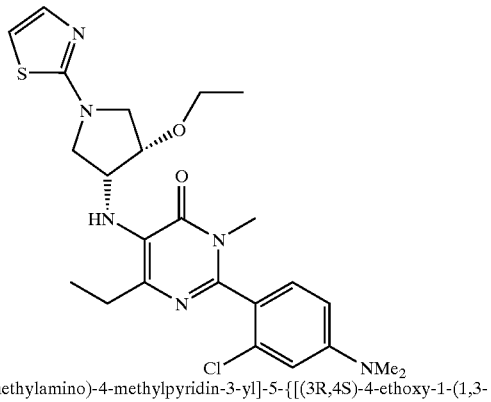

2-[6-(Dimethylamino)-4-methylpyridin-3-yl]-5-{[(3R,4S)-4-ethoxy-1-(1,3-thiazol-2-yl)pyrrolidin-3-yl]amino}-6-ethyl-3-methylpyrimidin-4(3H)-one

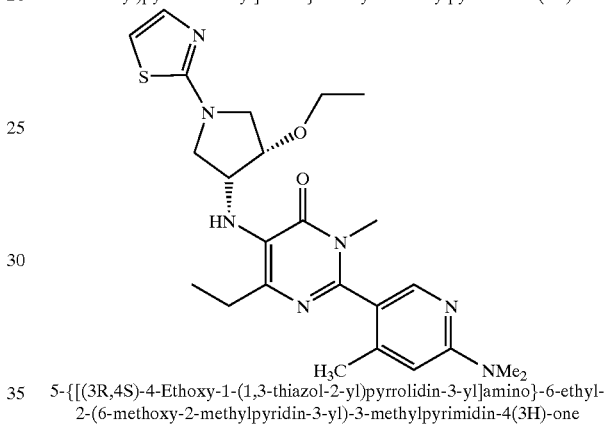

5-{[(3R,4S)-4-Ethoxy-1-(1,3-thiazol-2-yl)pyrrolidin-3-yl]amino}-6-ethyl-2-(6-methoxy-2-methylpyridin-3-yl)-3-methylpyrimidin-4(3H)-one

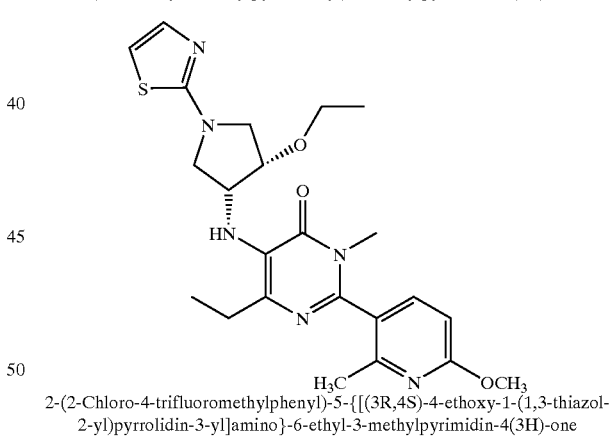

2-(2-Chloro-4-trifluoromethylphenyl)-5-{[(3R,4S)-4-ethoxy-1-(1,3-thiazol-2-yl)pyrrolidin-3-yl]amino}-6-ethyl-3-methylpyrimidin-4(3H)-one

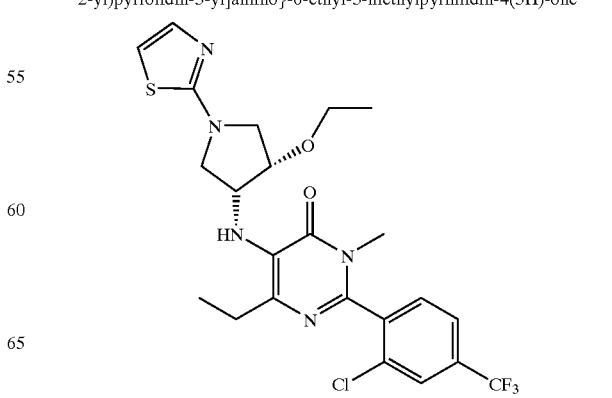

-continued 2-(2-Trifluoromethyl-4-dimethylaminophenyl)-5-{[(3R,4S)-4-ethoxy-1-(1,3-thiazol-2-yl)pyrrolidin-3-yl]amino}-6-ethyl-3-methylpyrimidin-4(3H)-one

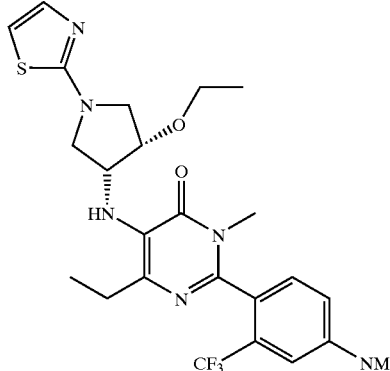

2-(2,4-Dichlorophenyl)-5-{[(3R,4S)-4-ethoxy-1-(1,3-thiazol-2-yl)-pyrrolidin-3-yl]amino}-3-ethyl-6-methylpyrimidin-4(3H)-one

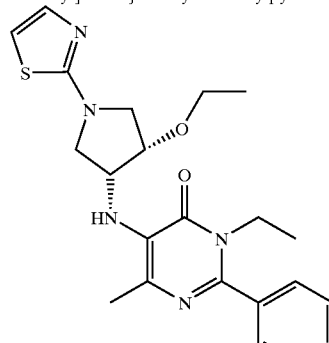

2-(2-Chloro-4-methoxyphenyl)-5-{[(3R,4S)-4-ethoxy-1-(1,3-thiazol-2-yl)pyrrolidin-3-yl]amino}-3-ethyl-6-methylpyrimidin-4(3H)-one

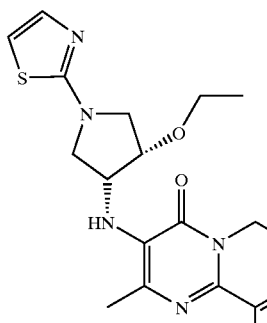

2-(2-Methyl-4-methoxyphenyl)-5-{[(3R,4S)-4-ethoxy-1-(1,3-thiazol-2-yl)pyrrolidin-3-yl]amino}-3-ethyl-6-methylpyrimidin-4(3H)-one

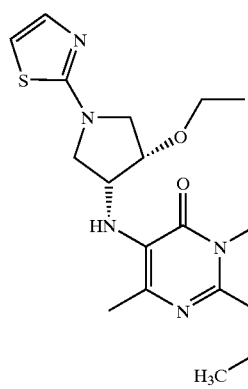

-continued 2-(2-Chloro-4-dimethylaminophenyl)-5-{[(3R,4S)-4-ethoxy-1-(1,3-thiazol-2-yl)pyrrolidin-3-yl]amino}-3-ethyl-6-methylpyrimidin-4(3H)-one

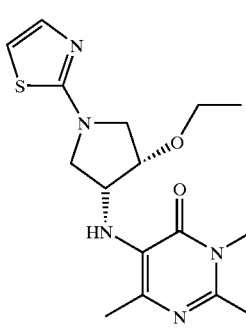

2-[6-(Dimethylamino)-4-methylpyridin-3-yl]-5-{[(3R,4S)-4-ethoxy-1-(1,3-thiazol-2-yl)pyrrolidin-3-yl]amino}-3-ethyl-6-methylpyrimidin-4(3H)-one

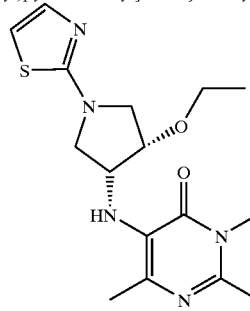

5-{[(3R,4S)-4-Ethoxy-1-(1,3-thiazol-2-yl)pyrrolidin-3-yl]amino}-3-ethyl-2-(6-methoxy-2-methylpyridin-3-yl)-6-methylpyrimidin-4(3H)-one

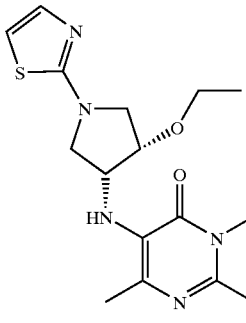

2-(2-Chloro-4-trifluoromethylphenyl)-5-{[(3R,4S)-4-ethoxy-1-(1,3-thiazol-2-yl)pyrrolidin-3-yl]amino}-3-ethyl-6-methylpyrimidin-4(3H)-one

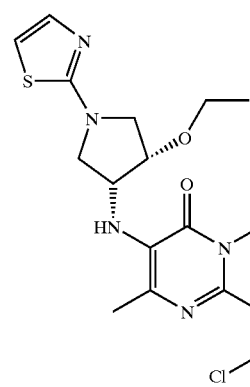

-continued 2-(2-Trifluoromethyl-4-dimethylaminophenyl)-5-{[(3R,4S)-4-ethoxy-1-(1,3-thiazol-2-yl)pyrrolidin-3-yl]amino}-3-ethyl-6-methylpyrimidin-4(3H)-one

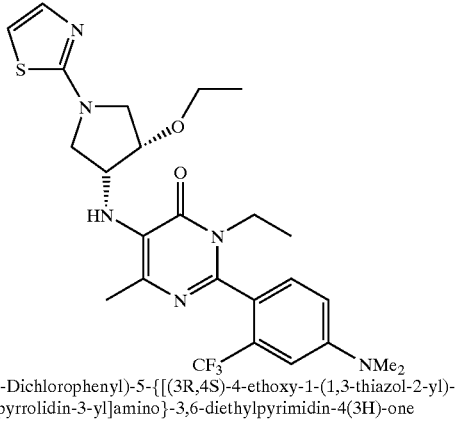

2-(2,4-Dichlorophenyl)-5-{[(3R,4S)-4-ethoxy-1-(1,3-thiazol-2-yl)-pyrrolidin-3-yl]amino}-3,6-diethylpyrimidin-4(3H)-one

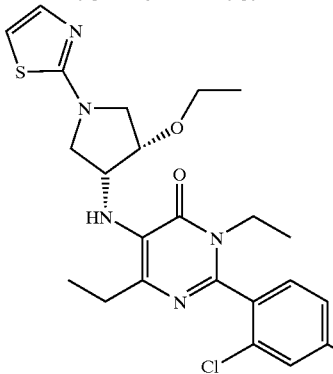

2-(2-Chloro-4-methoxyphenyl)-5-{[(3R,4S)-4-ethoxy-1-(1,3-thiazol-2-yl)pyrrolidin-3-yl]amino}-3,6-diethylpyrimidin-4(3H)-one

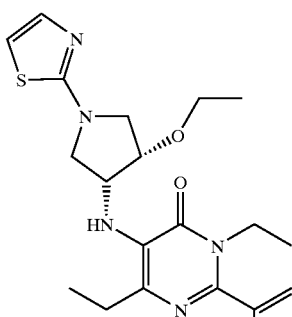

2-(2-Methyl-4-methoxyphenyl)-5-{[(3R,4S)-4-ethoxy-1-(1,3-thiazol-2-yl)pyrrolidin-3-yl]amino}-3,6-diethylpyrimidin-4(3H)-one

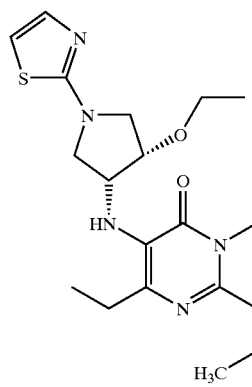

-continued 2-(2-Chloro-4-dimethylaminophenyl)-5-{[(3R,4S)-4-ethoxy-1-(1,3-thiazol-2-yl)pyrrolidin-3-yl]amino}-3,6-diethylpyrimidin-4(3H)-one

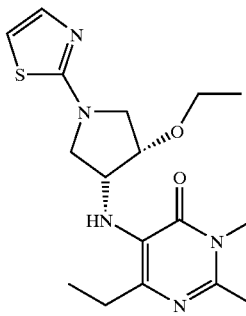

2-[6-(Dimethylamino)-4-methylpyridin-3-yl]-5-{[(3R,4S)-4-ethoxy-1-(1,3-thiazol-2-yl)pyrrolidin-3-yl]amino}-3,6-diethylpyrimidin-4(3H)-one

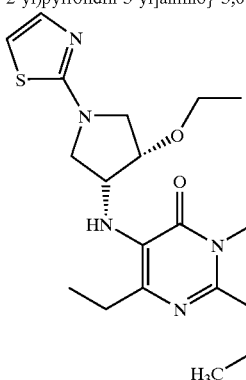

5-{[(3R,4S)-4-Ethoxy-1-(1,3-thiazol-2-yl)pyrrolidin-3-yl]amino}-3-ethyl-2-(6-methoxy-2-methylpyridin-3-yl)-3-6-diethylpyrimidin-4(3H)-one

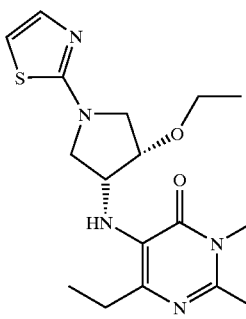

2-(2-Chloro-4-trifluoromethylphenyl)-5-{[(3R,4S)-4-ethoxy-1-(1,3-thiazol-2-yl)pyrrolidin-3-yl]amino}-3,6-diethylpyrimidin-4(3H)-one

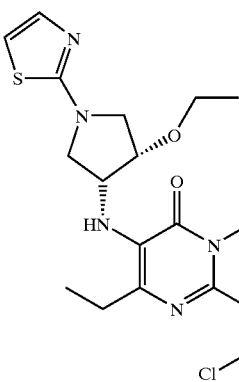

2-(2-Trifluoromethyl-4-dimethylaminophenyl)-5-{[(3R,4S)-4-ethoxy-1-(1,3-thiazol-2-yl)pyrrolidin-3-yl]amino}-3,6-diethylpyrimidin-4(3H)-one

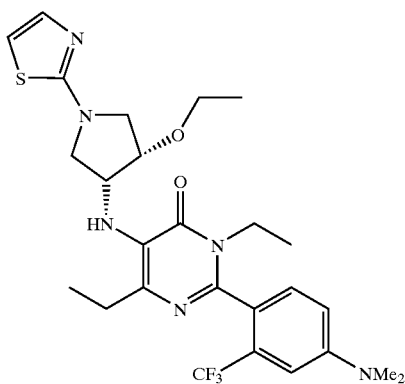

5-[(1-Ethylpropyl)amino]-2-(6-methoxy-2,3-dihydro-1H-inden-5-yl)-3,6-dimethylpyrimidin-4(3H)-one

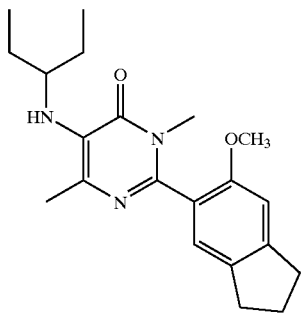

2-(6-Chloro-2,3-dihydro-1H-inden-5-yl)-5-[(1-ethylpropyl)amino]-3,6-dimethylpyrimidin-4(3H)-one

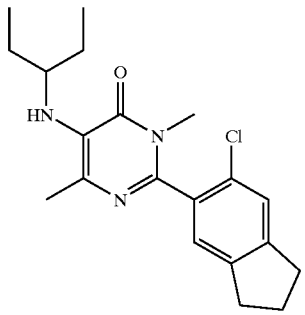

5-[(1-Ethylpropyl)amino]-2-(3-methoxy-5,6,7,8-tetrahydronaphthalen-2-yl)-3,6-dimethylpyrimidin-4(3H)-one

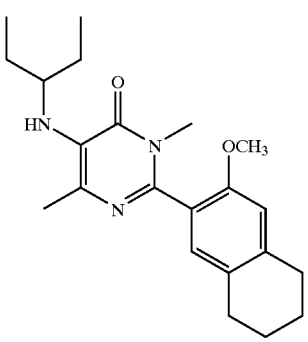

2-(3-Chloro-5,6,7,8-tetrahydronaphthalen-2-yl)-5-[(1-ethylpropyl)amino]-3,6-dimethylpyrimidin-4(3H)-one

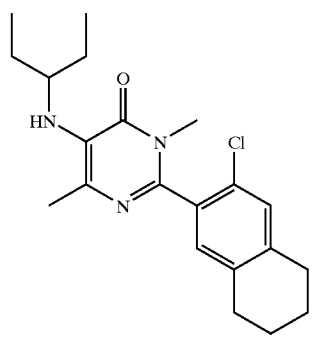

2-(6-Methoxy-2,3-dihydro-1H-inden-5-yl)-5-{[2-methoxy-1-(methoxymethyl)ethyl]amino}-3,6-dimethylpyrimidin-4(3H)-one

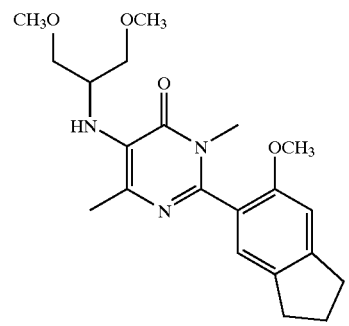

2-(6-Chloro-2,3-dihydro-1H-inden-5-yl)-5-{[2-methoxy-1-methoxymethyl)ethyl]amino}-3,6-dimethylpyrimidin-4(3H)-one

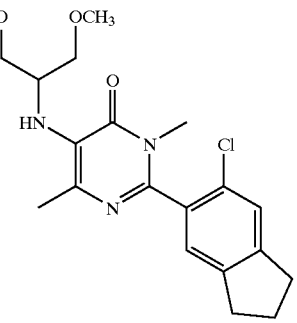

5-{[2-Methoxy-1-(methoxymethyl)ethyl]amino}-2-(3-methoxy-5,6,7,8-tetrahydronaphthalen-2-yl)-3,6-dimethylpyrimidin-4(3H)-one

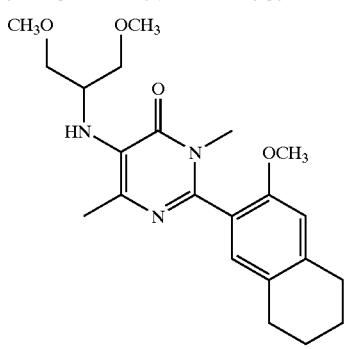

-continued 2-(3-Chloro-5,6,7,8-tetrahydronaphthalen-2-yl)-5-{[2-methoxy-1-(methoxymethyl)ethyl]amino}-3,6-dimethylpyrimidin-4(3H)-one

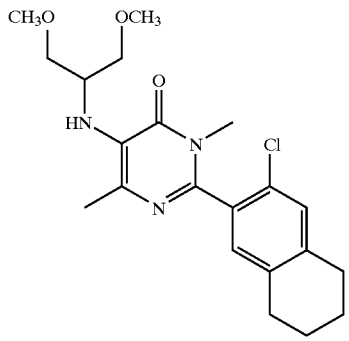

5-[(1-Ethylpropyl)amino]-2-(6-methoxy-1-oxo-2,3-dihydro-1H-inden-5-yl)-3,6-dimethylpyrimidin-4(3H)-one

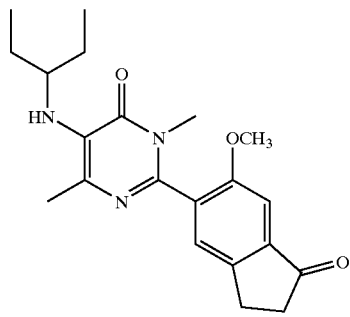

2-(6-Chloro-1-oxo-2,3-dihydro-1H-inden-5-yl)-5-[(1-ethylpropyl)amino]-3,6-dimethylpyrimidin-4(3H)-one

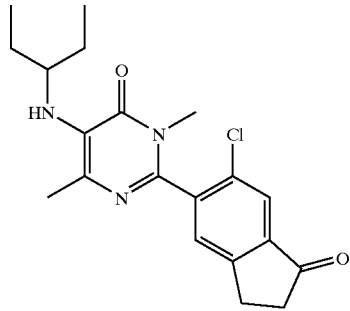

5-[(1-Ethylpropyl)amino]-2-(3-methoxy-5-oxo-5,6,7,8-tetrahydronaphthalen-2-yl)-3,6-dimethylpyrimidin-4(3H)-one

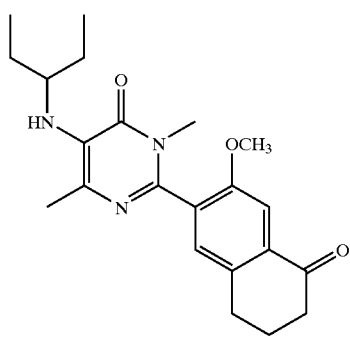

-continued 2-(3-Chloro-5-oxo-5,6,7,8-tetrahydronaphthalen-2-yl)-5-[(1-ethylpropyl)amino]-3,6-dimethylpyrimidin-4(3H)-one

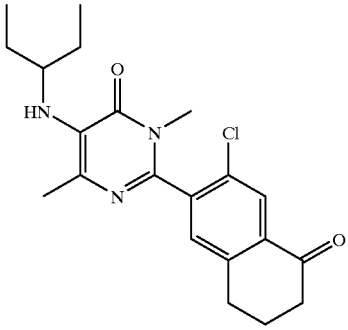

5-{[2-Methoxy-1-(methoxymethyl)ethyl]amino}-2-(6-methoxy-1-oxo-2,3-dihydro-1H-inden-5-yl)-3,6-dimethylpyrimidin-4(3H)-one

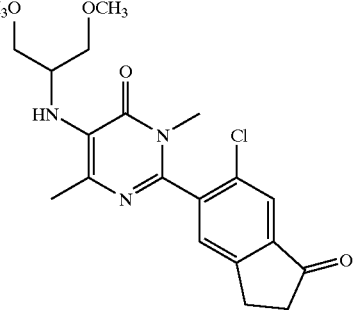

2-(6-Chloro-1-oxo-2,3-dihydro-1H-inden-5-yl)-5-{[2-methoxy-1-methoxymethyl)ethyl]amino}-3,6-dimethylpyrimidin-4(3H)-one

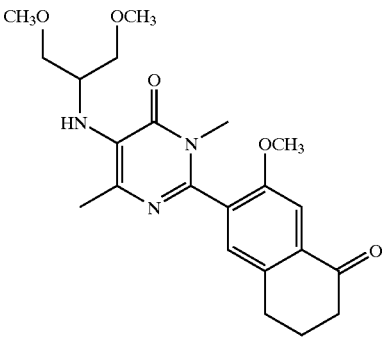

5-{[2-Methoxy-1-(methoxymethyl)ethyl]amino}-2-(3-methoxy-5-oxo-5,6,7,8-tetrahydronaphthalen-2-yl)-3,6-dimethylpyrimidin-4(3H)-one -continued 2-(3-Chloro-5-oxo-5,6,7,8-tetrahydronaphthalen-2-yl)-5-{[2-methoxy-1-(methoxymethyl)ethyl]amino}-3,6-dimethylpyrimidin-4(3H)-one

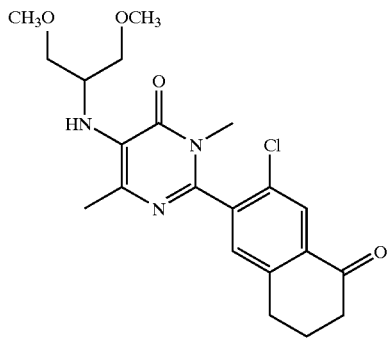

3-Ethyl-5-[(1-ethylpropyl)amino]-2-(6-methoxy-2,3-dihydro-1H-inden-5-yl)-6-methylpyrimidin-4(3H)-one

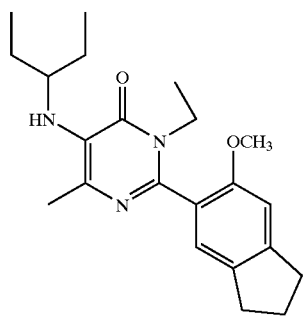

2-(6-Chloro-2,3-dihydro-1H-inden-5-yl)-3-ethyl-5-[(1-ethylpropyl)amino]-6-methylpyrimidin-4(3H)-one

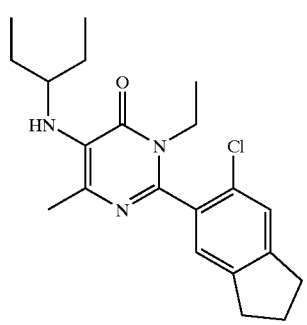

3-Ethyl-5-[(1-ethylpropyl)amino]-2-(3-methoxy-5,6,7,8-tetrahydronaphthalen-2-yl)-6-methylpyrimidin-4(3H)-one

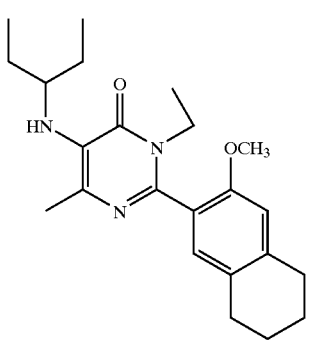

-continued 2-(3-Chloro-5,6,7,8-tetrahydronaphthalen-2-yl)-3-ethyl-5-[(1-ethylpropyl)amino]-6-methylpyrimidin-4(3H)-one

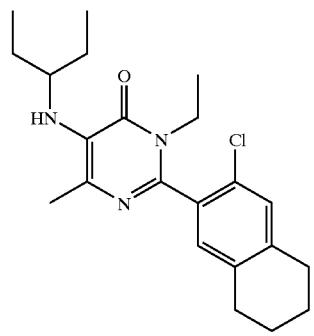

3-Ethyl-2-(6-methoxy-2,3-dihydro-1H-inden-5-yl)-5-{[2-methoxy-1-(methoxymethyl)ethyl]amino}-6-methylpyrimidin-4(3H)-one

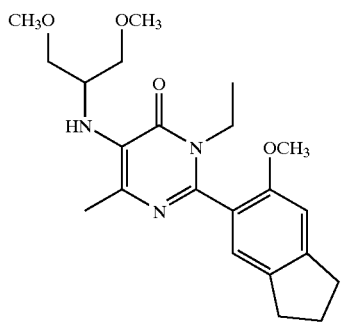

2-(6-Chloro-2,3-dihydro-1H-inden-5-yl)-3-ethyl-5-{[2-methoxy-1-methoxymethyl)ethyl]amino}-6-methylpyrimidin-4(3H)-one

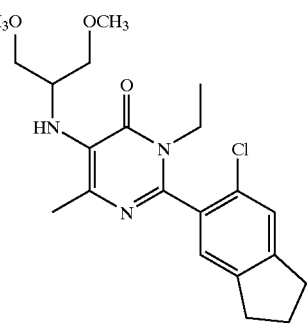

3-Ethyl-5-{[2-methoxy-1-(methoxymethyl)ethyl]amino}-2-(3-methoxy-5,6,7,8-tetrahydronaphthalen-2-yl)-6-methylpyrimidin-4(3H)-one

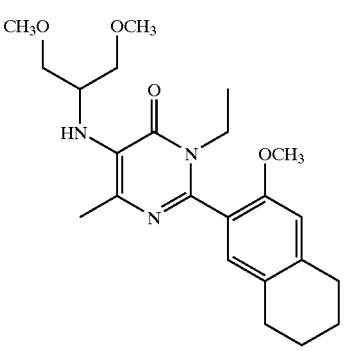

-continued 2-(3-Chloro-5,6,7,8-tetrahydronaphthalen-2-yl)-3-ethyl-5-{[2-methoxy-1-(methoxymethyl)ethyl]amino}-6-methylpyrimidin-4(3H)-one

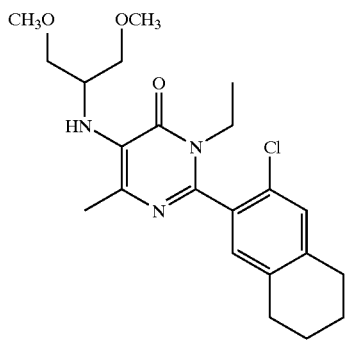

3-Ethyl-5-[(1-ethylpropyl)amino]-2-(6-methoxy-1-oxo-2,3-dihydro-1H-inden-5-yl)-6-methylpyrimidin-4(3H)-one

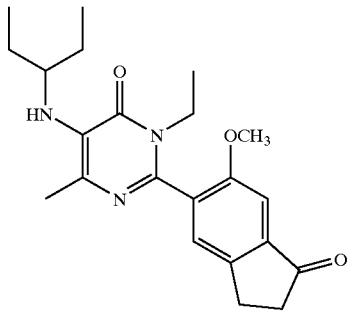

2-(6-Chloro-1-oxo-2,3-dihydro-1H-inden-5-yl)-3-ethyl-5-[(1-ethylpropyl)amino]-6-methylpyrimidin-4(3H)-one

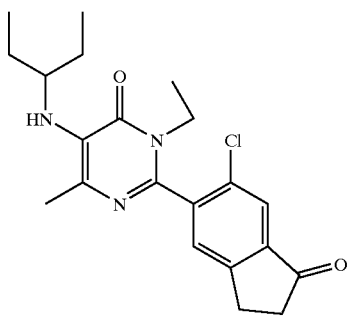

3-Ethyl-5-[(1-ethylpropyl)amino]-2-(3-methoxy-5-oxo-5,6,7,8-tetrahydronaphthalen-2-yl)-6-methylpyrimidin-4(3H)-one

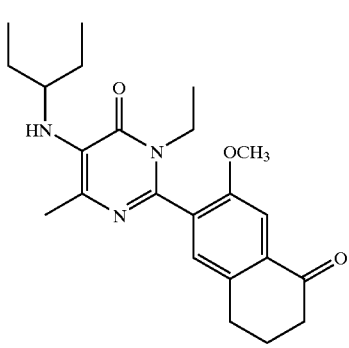

-continued 2-(3-Chloro-5-oxo-5,6,7,8-tetrahydronaphthalen-2-yl)-3-ethyl-5-[(1-ethylpropyl)amino]-6-methylpyrimidin-4(3H)-one

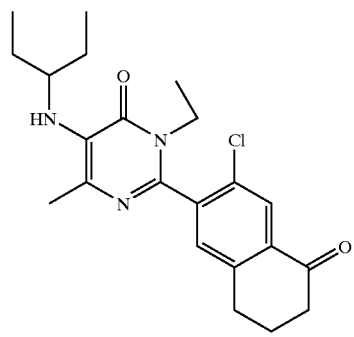

3-Ethyl-5-{[2-methoxy-1-(methoxymethyl)ethyl]amino}-2-(6-methoxy-1-oxo-2,3-dihydro-1H-inden-5-yl)-6-methylpyrimidin-4(3H)-one

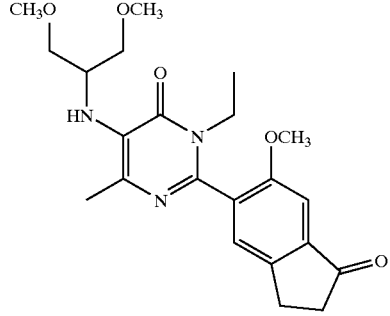

2-(6-Chloro-1-oxo-2,3-dihydro-1H-inden-5-yl)-3-ethyl-5-{[2-methoxy-1-methoxymethyl)ethyl]amino}-6-methylpyrimidin-4(3H)-one

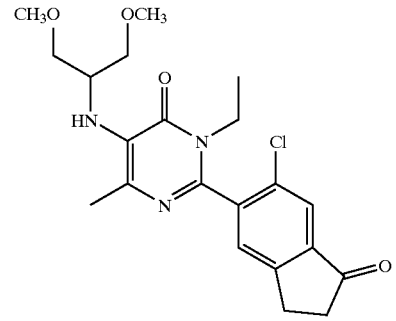

3-Ethyl-5-{[2-methoxy-1-(methoxymethyl)ethyl]amino}-2-(3-methoxy-5-oxo-5,6,7,8-tetrahydronaphthalen-2-yl)-6-methylpyrimidin-4(3H)-one

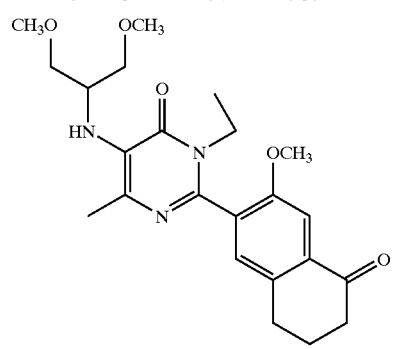

-continued 2-(3-Chloro-5-oxo-5,6,7,8-tetrahydronaphthalen-2-yl)-3-ethyl-5-{[2-methoxy-1-(methoxymethyl)ethyl]amino}-6-methylpyrimidin-4(3H)-one

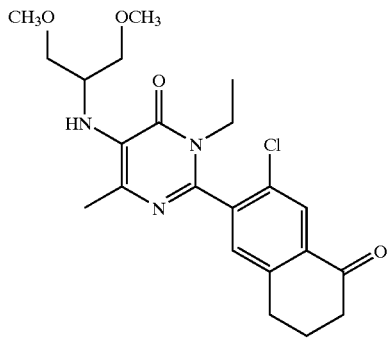

6-Ethyl-5-[(1-ethylpropyl)amino]-2-(6-methoxy-2,3-dihydro-1H-inden-5-yl)-3-methylpyrimidin-4(3H)-one

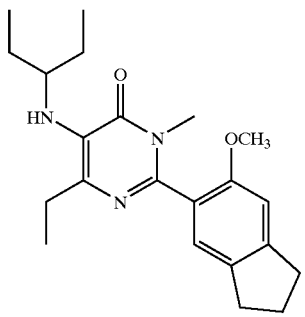

2-(6-Chloro-2,3-dihydro-1H-inden-5-yl)-6-ethyl-5-[(1-ethylpropyl)amino]-3-methylpyrimidin-4(3H)-one

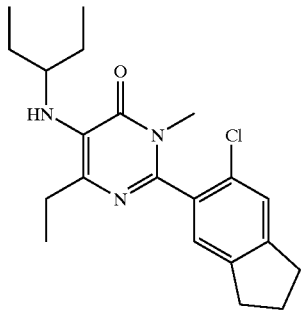

6-Ethyl-5-[(1-ethylpropyl)amino]-2-(3-methoxy-5,6,7,8-tetrahydronaphthalen-2-yl)-3-methylpyrimidin-4(3H)-one

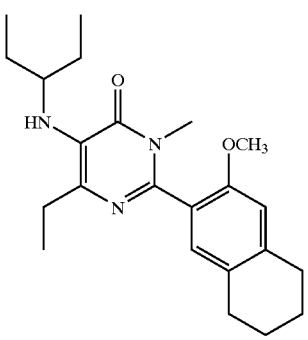

-continued 2-(3-Chloro-5,6,7,8-tetrahydronaphthalen-2-yl)-6-ethyl-5-[(1-ethylpropyl)amino]-3-methylpyrimidin-4(3H)-one

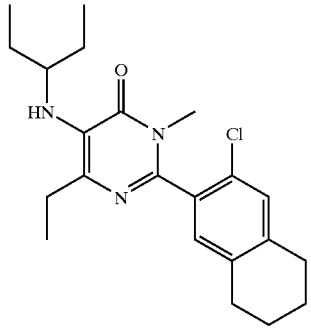

6-Ethyl-2-(6-Methoxy-2,3-dihydro-1H-inden-5-yl)-5-{[2-methoxy-1-(methoxymethyl)ethyl]amino}-3-methylpyrimidin-4(3H)-one

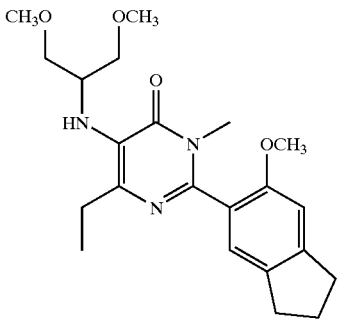

2-(6-Chloro-2,3-dihydro-1H-inden-5-yl)-6-ethyl-5-{[2-methoxy-1-methoxymethyl)ethyl]amino}-3-methylpyrimidin-4(3H)-one

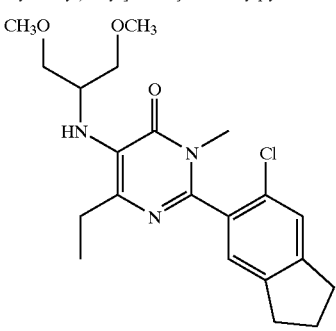

6-Ethyl-5-{[2-methoxy-1-(methoxymethyl)ethyl]amino}-2-(3-methoxy-5,6,7,8-tetrahydronaphthalen-2-yl)-3-methylpyrimidin-4(3H)-one

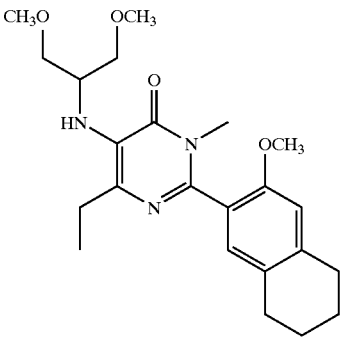

-continued 2-(3-Chloro-5,6,7,8-tetrahydronaphthalen-2-yl)-6-ethyl-5-{[2-methoxy-1-(methoxymethyl)ethyl]amino}-3-methylpyrimidin-4(3H)-one

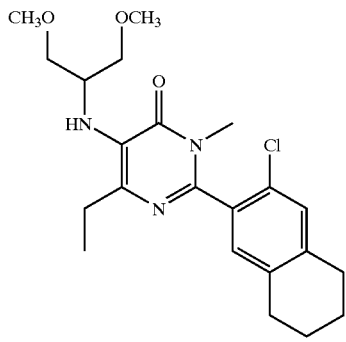

6-Ethyl-5-[(1-ethylpropyl)amino]-2-(6-methoxy-1-oxo-2,3-dihydro-1H-inden-5-yl)-3-methylpyrimidin-4(3H)-one

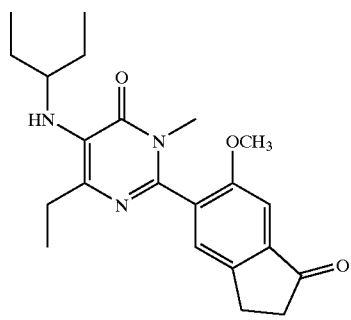

2-(6-Chloro-1-oxo-2,3-dihydro-1H-inden-5-yl)-6-ethyl-5-[(1-ethylpropyl)amino]-3-methylpyrimidin-4(3H)-one

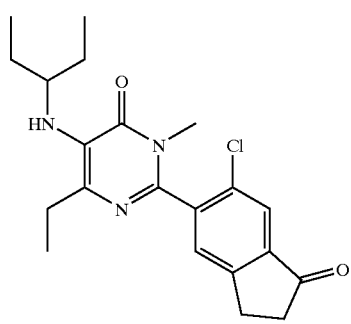

6-Ethyl-5-[(1-ethylpropyl)amino]-2-(3-methoxy-5-oxo-5,6,7,8-tetrahydronaphthalen-2-yl)-3-methylpyrimidin-4(3H)-one

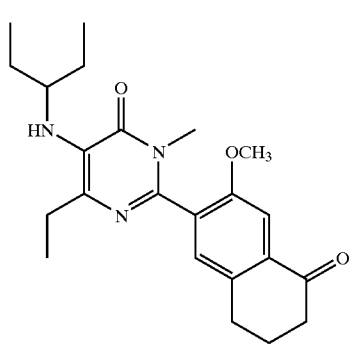

-continued 2-(3-Chloro-5-oxo-5,6,7,8-tetrahydronaphthalen-2-yl)-6-ethyl-5-[(1-ethylpropyl)amino]-3-methylpyrimidin-4(3H)-one

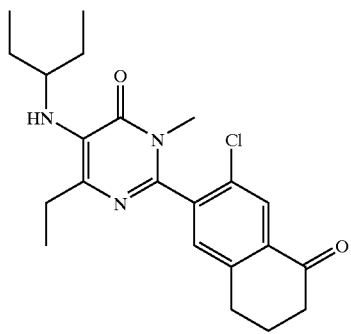

6-Ethyl-5-{[2-methoxy-1-(methoxymethyl)ethyl]amino}-2-(6-methoxy-1-oxo-2,3-dihydro-1H-inden-5-yl)-3-methylpyrimidin-4(3H)-one

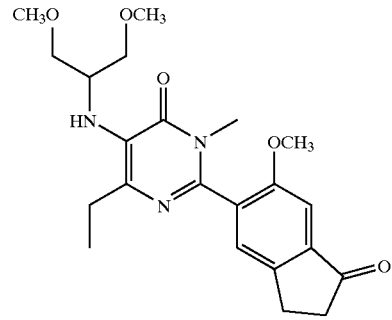

2-(6-Chloro-1-oxo-2,3-dihydro-1H-inden-5-yl)-6-ethyl-5-{[2-methoxy-1-methoxymethyl)ethyl]amino}-3-methylpyrimidin-4(3H)-one

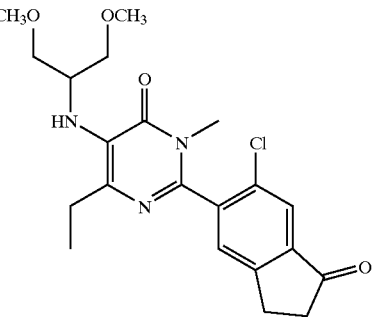

6-Ethyl-5-{[2-methoxy-1-(methoxymethyl)ethyl]amino}-2-(3-methoxy-5-oxo-5,6,7,8-tetrahydronaphthalen-2-yl)-3-methylpyrimidin-4(3H)-one

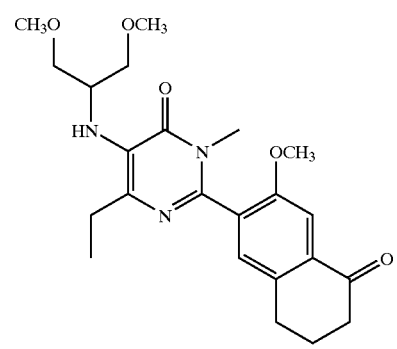

-continued 2-(3-Chloro-5-oxo-5,6,7,8-tetrahydronaphthalen-2-yl)-6-ethyl-5-{[2-methoxy-1-(methoxymethyl)ethyl]amino}-3-methylpyrimidin-4(3H)-one

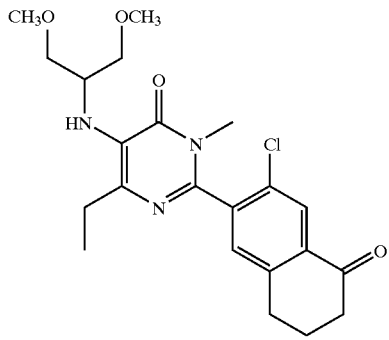

5-[(1-Ethylpropyl)amino]-2-(6-methoxy-2,3-dihydro-1H-inden-5-yl)-3,6-dimethylpyrimidin-4(3H)-one

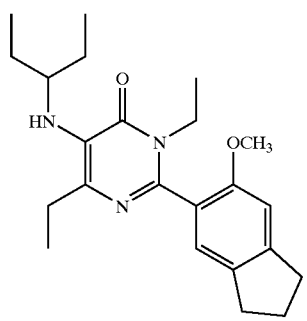

2-(6-Chloro-2,3-dihydro-1H-inden-5-yl)-5-[(1-ethylpropyl)amino]-3,6-dimethylpyrimidin-4(3H)-one

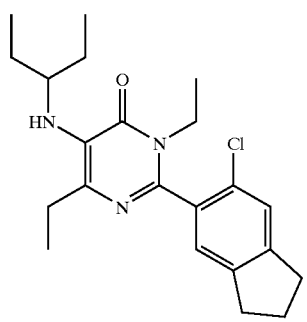

5-[(1-Ethylpropyl)amino]-2-(3-methoxy-5,6,7,8-tetrahydronaphthalen-2-yl)-3,6-dimethylpyrimidin-4(3H)-one

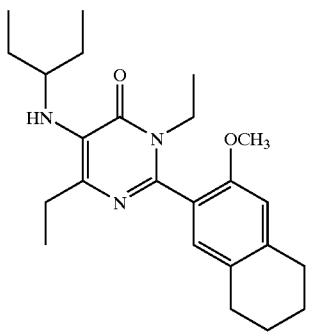

-continued 2-(3-Chloro-5,6,7,8-tetrahydronaphthalen-2-yl)-5-[(1-ethylpropyl)amino]-3,6-dimethylpyrimidin-4(3H)-one

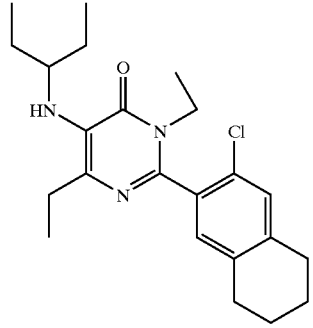

2-(6-Methoxy-2,3-dihydro-1H-inden-5-yl)-5-{[2-methoxy-1-(methoxymethyl)ethyl]amino}-3,6-dimethylpyrimidin-4(3H)-one

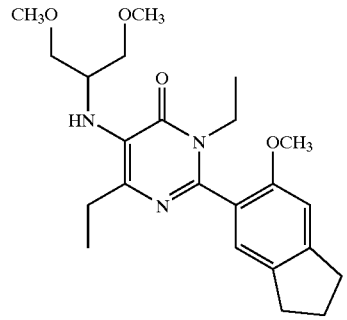

2-(6-Chloro-2,3-dihydro-1H-inden-5-yl)-5-{[2-methoxy-1-methoxymethyl)ethyl]amino}-3,6-dimethylpyrimidin-4(3H)-one

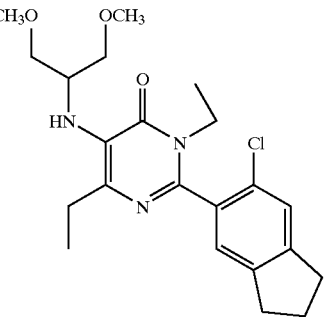

5-{[2-Methoxy-1-(methoxymethyl)ethyl]amino}-2-(3-methoxy-5,6,7,8-tetrahydronaphthalen-2-yl)-3,6-dimethylpyrimidin-4(3H)-one

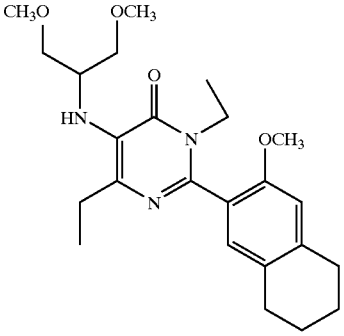

-continued 2-(3-Chloro-5,6,7,8-tetrahydronaphthalen-2-yl)-5-{[2-methoxy-1-(methoxymethyl)ethyl]amino}-3,6-dimethylpyrimidin-4(3H)-one

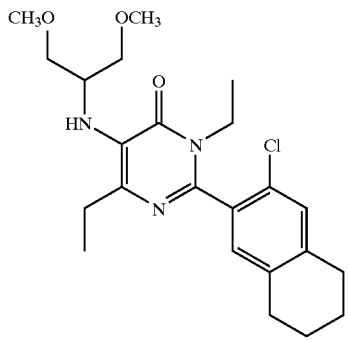

5-[(1-Ethylpropyl)amino]-2-(6-methoxy-1-oxo-2,3-dihydro-1H-inden-5-yl)-3,6-dimethylpyrimidin-4(3H)-one

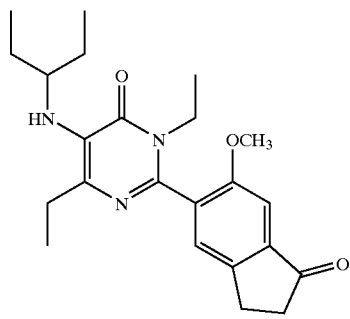

2-(6-Chloro-1-oxo-2,3-dihydro-1H-inden-5-yl)-5-[(1-ethylpropyl)amino]-3,6-dimethylpyrimidin-4(3H)-one

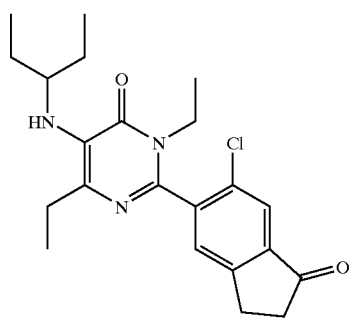

5-[(1-Ethylpropyl)amino]-2-(3-methoxy-5-oxo-5,6,7,8-tetrahydronaphthalen-2-yl)-3,6-dimethylpyrimidin-4(3H)-one

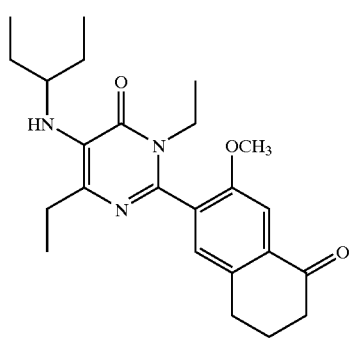

-continued 2-(3-Chloro-5-oxo-5,6,7,8-tetrahydronaphthalen-2-yl)-5-[(1-ethylpropyl)amino]-3,6-dimethylpyrimidin-4(3H)-one

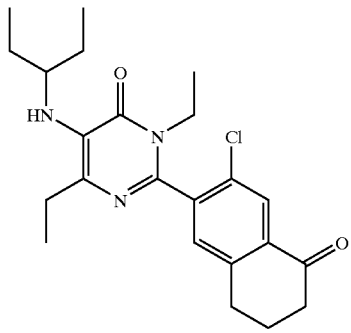

5-{[2-Methoxy-1-(methoxymethyl)ethyl]amino}-2-(6-methoxy-1-oxo-2,3-dihydro-1H-inden-5-yl)-3,6-dimethylpyrimidin-4(3H)-one

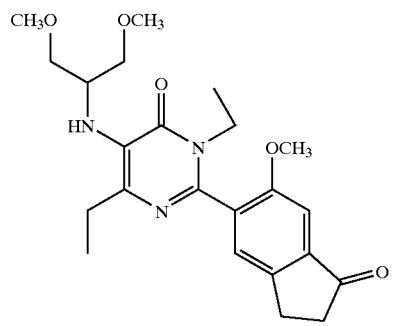

2-(6-Chloro-1-oxo-2,3-dihydro-1H-inden-5-yl)-5-{[2-methoxy-1-methoxymethyl)ethyl]amino}-3,6-dimethylpyrimidin-4(3H)-one

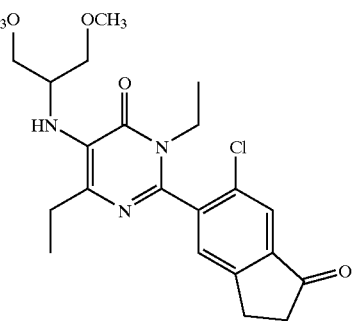

5-{[2-Methoxy-1-(methoxymethyl)ethyl]amino}-2-(3-methoxy-5-oxo-5,6,7,8-tetrahydronaphthalen-2-yl)-3,6-dimethylpyrimidin-4(3H)-one

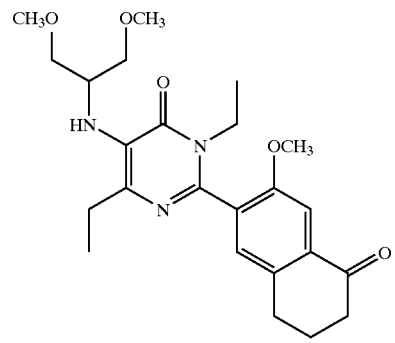

-continued 2-(3-Chloro-5-oxo-5,6,7,8-tetrahydronaphthalen-2-yl)-5-{[2-methoxy-1-(methoxymethyl)ethyl]amino}-3,6-dimethylpyrimidin-4(3H)-one

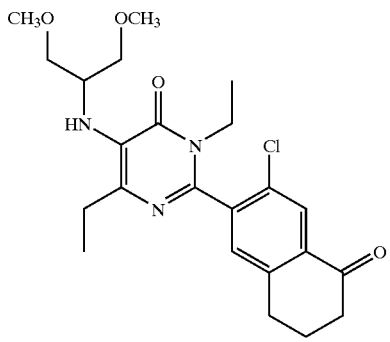

Compounds provided herein can have one or more asymmetric centers or planes, and all chiral (enantiomeric and diastereomeric) and racemic forms of the compound are included in the present invention. Many geometric isomers of olefins, C=N double bonds, and the like can also be present in the compounds, and all such stable isomers are contemplated in the present invention. Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by a asymmetric synthesis route enabling the preparation of enantiomerically enriched material. The present invention encompasses all possible tautomers of the compounds represented by Formula I.

Compounds of the invention can be prepared using the synthetic routes illustrated in Charts A–H provided below. Starting materials are either commercially available or can be prepared by procedures known to one of ordinary skill in organic chemistry.

CHART A

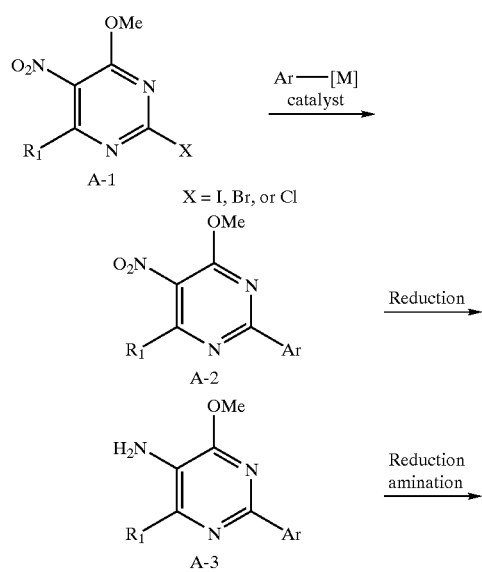

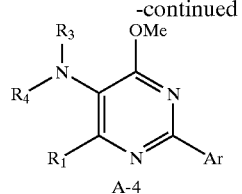

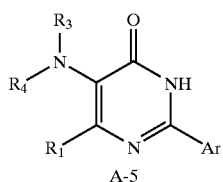

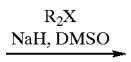

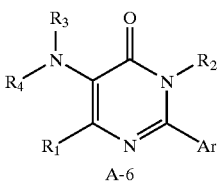

In Chart A, X=bromo, iodo, or chloro and $R_3$ and $R_4$ are as defined for formula I. Compound such as A-1 can be prepared according to literature procedures (T. L. Cupps et al., *J. Org. Chem.* 1983, 48, 1060). Intermediate A-1 can be converted into A-2 by a transition metal-catalyzed coupling with a metalloaryl reagent (Ar-[M]). Commonly used reagent/catalyst pairs include aryl boronic acid/palladium(0) (N. Miyaura and A. Suzuki, *Chem. Rev.* 1995, 95, 2457), aryl trialkylstannane/palladium(0) (T. N. Mitchell, *Synthesis* 1992, 803), arylzinc/palladium(0) and aryl Grignard/nickel (II). Palladium(0) represents a catalytic system made of various combinations of metal/ligand pair which includes, but not limited to, tetrakis(triphenylphosphine)-palladium (0), palladium(II) acetate/tri(o-tolyl)phosphine, tris-(dibenzylideneacetone) dipalladium(0)/tri-tert-butylphosphine, and dichloro [1,1'-bis(diphenylphosphine)-ferrocene]palladium(0). Nickel(II) represents a nickel-containing catalyst such as [1,2-bis(diphenylphosphino)ethane]dichloronickel (II) and [1,3-bis(diphenylphosphino)propane]dichloronickel (II). The nitro group present in A-2 may be reduced by a variety of methods known in the art, including hydrogenation with hydrogen and transition metal catalysts or the use of sodium hydrosulfite in aqueous solutions or the use of Zn/CaCl$_2$ in aqueous ethanol to afford A-3. A-3 may be transformed into A-4 by reductive amination using aldehydes and ketones and reducing agents such as sodium triacetoxyborohydride in inert solvents. The order of the steps in Chart A may be altered depending upon the substitution of the aromatic (Ar) group. For instance, for disubstituted aromatic analogs, A-1 may first be coupled with a boronic acid, the nitro group reduced and the resulting amine alkylated to give compouns of generic structure A-4. Conversion of A-4 into A-5 may be carried out by a number of methods known in the art, including for example the use of hydrochloric acid, boron trichloride, boron tribromide, acetic acid, trimethylsilyl bromide, trimethylsilyl chloride, or aluminum tribromide, in a solvent such as dichloromethane or DMF. N-Alkylation of A-5 to the target compound A-6 may be accomplished using a base such as but not limited to alkali metal hydride or alkali metal alkoxide in inert solvents such as but not limited to THF, DMF, or methyl sulfoxide. Alkylation may be conducted using alkyl halide, suitably bromide, iodide, tosylate or mesylate at temperatures ranging from −78° C. to 100° C.

CHART B

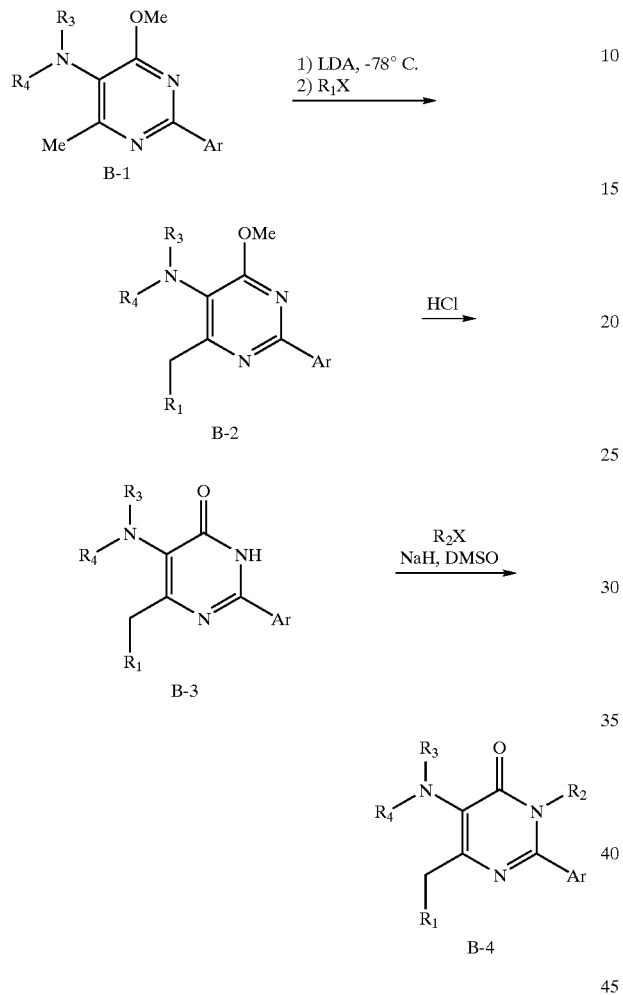

The alkylation of the methyl group (or other alkyl group) on position 6 of the pyrimidine (e.g., B-1) may be accomplished using a strong base such as but not limited to alkali metal hydride, alkali metal amide or alkali metal alkoxide in inert solvents such as but not limited to THF, DMF, or methyl sulfoxide. Alkylation may be conducted using alkyl halide, suitably bromide, iodide, tosylate or mesylate at temperatures ranging from −78° C. to 100° C. Using the same methods described in Chart A, compounds of formula B-4 can also be prepared as outlined in Chart B.

CHART C

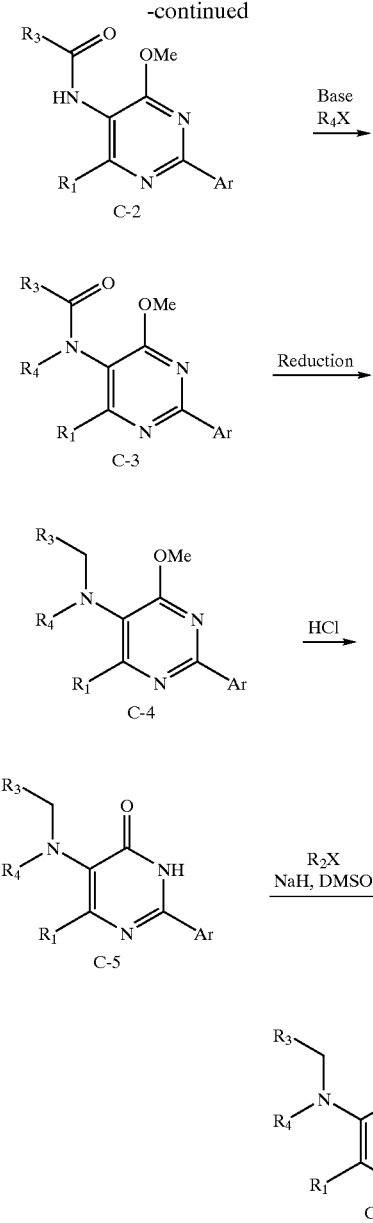

An alternative method for introducing the substituents $R_3$ and $R_4$ to give compounds of formula C-6 is outlined in Chart C and may be accomplished by a variety of methods known in the art. These include reaction of the amine C-1 with acid chlorides or anhydrides in the presence of bases such as but not limited to triethylamine or pyridine in inert solvents such as dichloromethane or toluene. The N—H group is then deprotonated by a strong base such as but not limited to alkali metal hydride, alkali metal amide or alkali metal alkoxide in inert solvents such as but not limited to THF, DMF, or methyl sulfoxide to afford C-3. Alkylation may be conducted using alkyl halide, suitably bromide or iodide, at temperatures ranging from 0° C. to 100° C. Reduction of C-3 with reducing agents such as but not limited to lithium aluminum hydride, borane or diisobutylaluminum hydride in inert solvents such as but not limited to THF, ether, or toluene furnsishes compounds of the formula C-4. Using the same methods outlined in Chart A, compounds of the formula C-6 can also be prepared as outlined in Chart C.

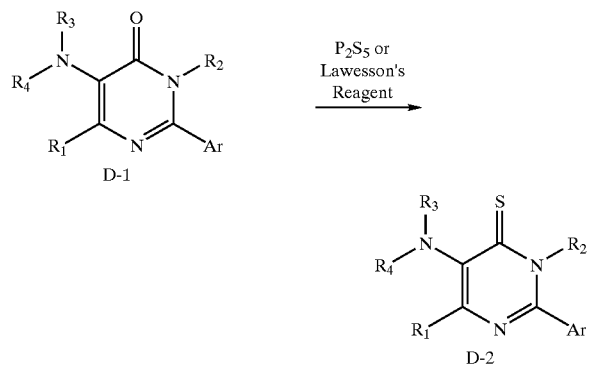

A route for preparing pyrimidinthiones is outlined in Chart D. Compound D-1 can be prepared by the methods outlined in Charts A–C. Using methods well known in the literature, D-1 can be converted into the target compound D-2 using reagents such as but not limited to $P_2S_5$ and Lawesson's reagent (see K. Woerner, et al., *Helv. Chim. Acta* 1999, 82, 2094–2104).

CHART E

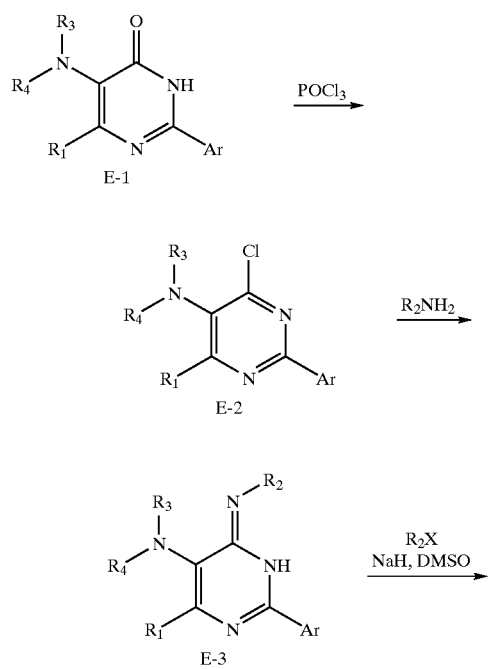

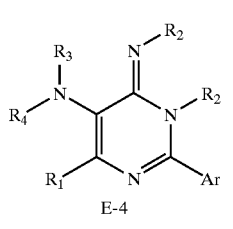

A route for preparing iminopyrimidines is shown in Chart E. Compound E-1 can be prepared by the methods outlined in Charts A–C. Using methods well known in the literature, E-1 can be converted into the target compound E-2 using reagents such as but not limited to $POCl_3$. Treating E-2 with amines in suitable solvents such as but not limited to ethanol or toluene affords E-3 (see D. M. Brown, P. K. T. Lin, *Carbohydr. Res.* 1991, 216, 129–139; H. Paulsen, U. Maass, *Chem. Ber.* 1981, 114, 346–351). Using the same methods outlined in Chart A, compounds of the formula E-4 can also be prepared as outlined in Chart E.

A route for preparing indanyl derivative is outlined in Chart F. Compound F-1 can be prepared by the methods described in Chart A. Using methods well known in the literatue, F-1 can react with indene epoxide F-2 in the presence of a lewis acid such as but not limited to magnesium perchlorate, boron trifluoride to form the epoxide ring opened products F-3 in a trans stereo chemistry. Treating F-3 under Mitsunobu reaction conditions using p-nitrobenzoic acid as the nucleophile and followed by hydrolysis results in the configuration conversion of trans amino alcohol to cis to provides compounds F-5. Alkylation of F-5 at the hydroxyl group can be conducted using a base such as but not limited to alkali metal hydride or alkali metal alkoxide in inert solvents such as but not limited to THF, DMF, or methyl sulfoxide to afford the ether compounds F-6. Acetylation of the hydroxyl group may be accomplished with acid chlorides or anhydrides in the presence of bases such as but not limited triethylamine or pyridine in inert solvents such as dichloromethane or toluene to form the ester compounds F-6. Using the same methods outlined in Chart A, compounds of the formula F-8 can also be prepared as outlined in Chart F.

CHART F

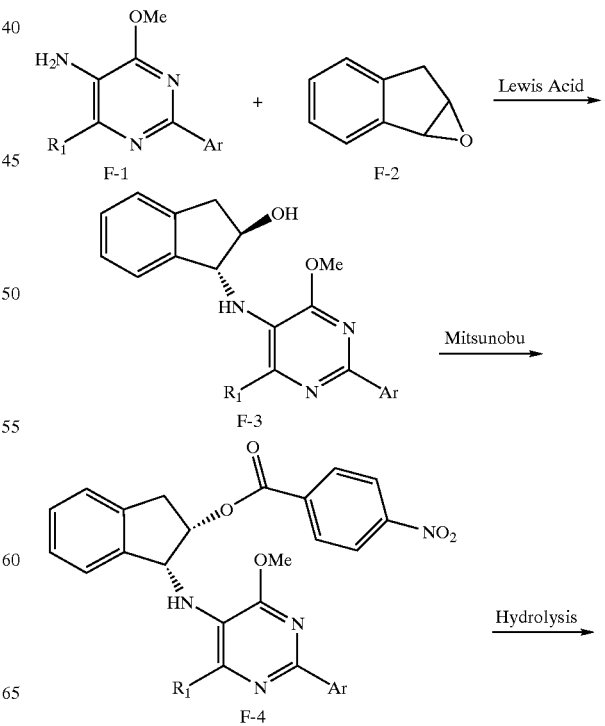

-continued

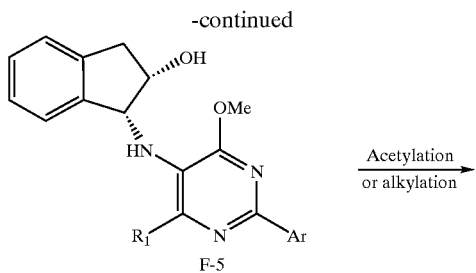
F-5

Acetylation or alkylation →

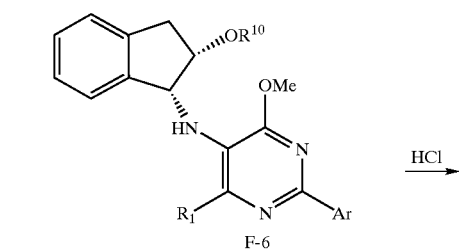
F-6

HCl →

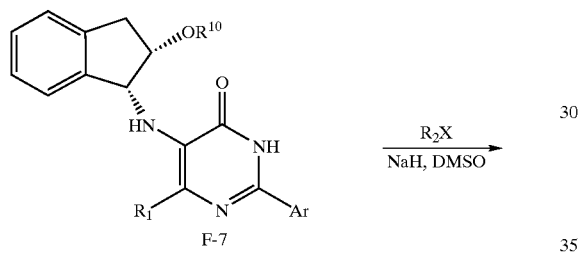
F-7

R$_2$X / NaH, DMSO →

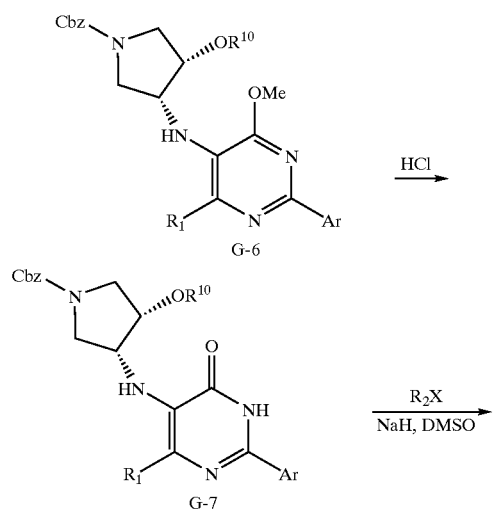
F-8

A route for preparing pyrrolidine derivative is outlined in Chart G. Compound G-1 can be prepared by the methods described in Chart A. The epoxide G-2 is prepared by treatment of the commercially available olefin (benzyl 2,5-dihydro-1H-pyrrole-1-carboxylate) with MCPBA. Using methods well known in the literatue, G-1 can react with pyrrolidine epoxide G-2 in the presence of a lewis acid such as but not limited to magnesium perchlorate, boron trifluoride to form the epoxide ring opened products G-3 in a trans stereo chemistry. Using the same methods outlined in Chart F, compounds G-8 can be prepared as outlined in Chart G. Finally, removal of the CBZ group and treatment of the amine with acetylating reagents such as but not limited to chloroformate or acid chloride results in the formation of carbamate or amides G-9. An aryl or heteroaryl group can also be introduced by using the protocol of Buchwald et al (*J. Org. Chem.* 2000, 1158).

CHART G

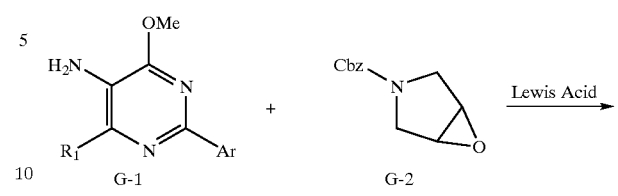
G-1 + G-2

Lewis Acid →

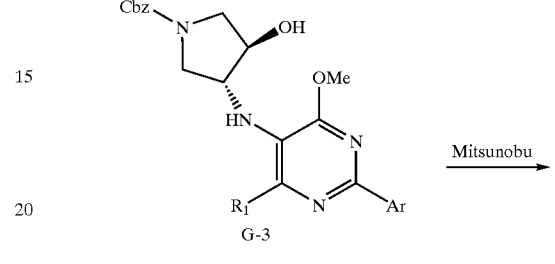
G-3

Mitsunobu →

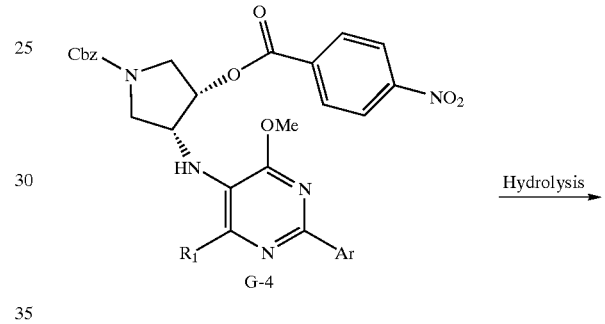
G-4

Hydrolysis →

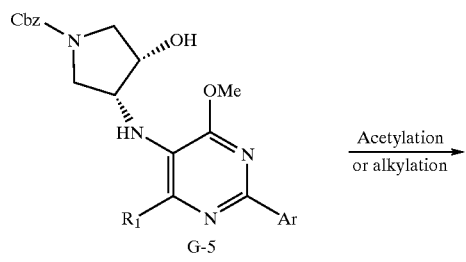
G-5

Acetylation or alkylation →

G-6

HCl →

G-7

R$_2$X / NaH, DMSO →

-continued

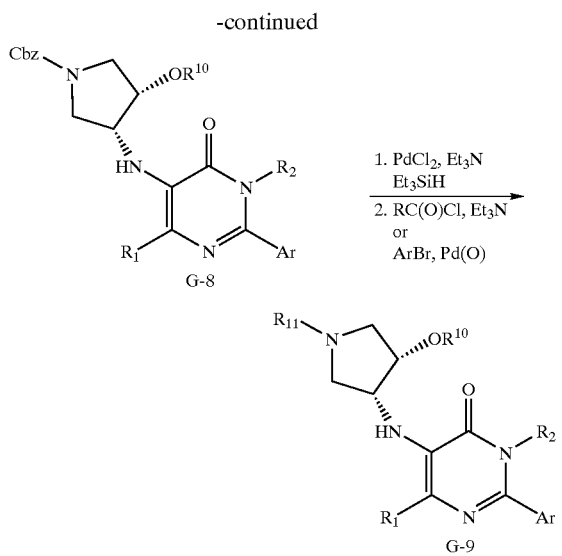

The compounds of formula I can also be prepared as illustrated in Chart H as H-5. Compound H-1 can be prepared by the methods described in Chart A. Treating H-1 with (butyl) nitrite and copper halide (for example CuBr) affords the halogen (I, Br, Cl) compounds H-2. Following the protocol of Buchwald et al (*J. Org. Chem.* 2000, 1158), the desired amines H-3 can be produced. Using the same methods outlined in Chart A, compounds of the formula H-5 can also be prepared as outlined in Chart H.

CHART H

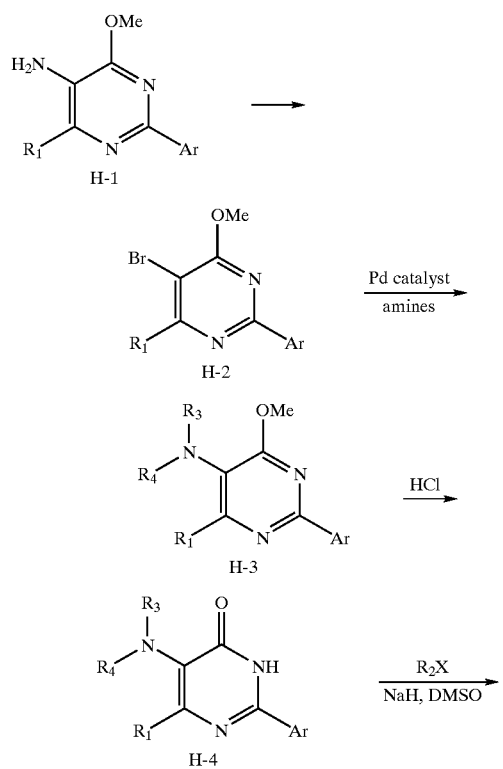

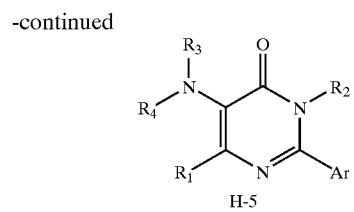

The present invention also encompasses pharmaceutically acceptable salts of compounds of formula I. Examples of pharmaceutically acceptable salts are salts prepared from inorganic acids or organic acids, such as inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine,chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remin ton's Pharmaceutical Sciences, 17th ea., Mack Publishing Company, Easton, Pa., 1985, p. 1418, the disclosure of which is hereby incorporated by reference. In another aspect, the present invention provide a prodrug of a compound of formula I. The prodrug is prepared with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). Prodrugs include, but are not limited to, compounds of formula I wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. The prodrug can be readily prepared from the compounds of formula I using methods known in the art. See, e.g. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172–178, 949–982 (1995). For example, the compounds of formula I can be transformed into prodrugs by converting one or more of the hydroxy or carboxy groups into esters. For example, prodrugs of the compounds of formula (I) can be prepared by modifying functional groups present on the compound in such a way that the modifications are cleaved, either in routine manipulation or in vivo, to the parent compound.

In another aspect, the present invention provides a pharmaceutical composition comprising a compound of claim 1, a stereoisomer thereof, a pharmaceutically acceptable salt thereof, or a prodrug thereof, or a pharmaceutically acceptable salt of the prodrug thereof. In one embodiment, the pharmaceutical composition further comprises a pharmaceutically acceptable carrier, diluent, or excipient therefor. In making the pharmaceutical compositions of the present invention, one or more compounds will usually be mixed with, diluted by or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions can be in the form of tablets, pills, powders, lozenges, sachets, cachets, elixirs, suspensions, emulsions, solutions, syrups, aerosols (as a solid or in a liquid medium), ointments containing, for example, up to 60% by weight of active compound, soft and hard gelatin capsules, suppositories, sterile injectable solutions and sterile packaged powders. Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film-coated to mask any unpleasant taste, or used to protect the active ingredients from the atmosphere, or to allow selective disintegration of the tablet in the gastrointestinal tract. Liquid dose forms for oral administration can contain coloring or flavoring agents to increase patient acceptance. In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol. Suitable pharmaceutical carriers are described in "Remington's Pharmaceutical Sciences", A. Osol, a standard reference in the field.

Dosage forms suitable for administration generally contain from about 1 mg to about 100 mg of active ingredient per unit. In these pharmaceutical compositions, the active ingredient will ordinarily be present in an amount of about 0.5 to 95% by weight based on the total weight of the composition. Examples of dosage forms for administration of the compounds of this invention includes the following: (1) Capsules. A large number of units capsules are prepared by filling standard two-piece hard gelatin capsules each with 100 mg of powdered active ingredient, 150 mg lactose, 50 mg cellulose, and 6 mg magnesium stearate. (2) Soft Gelatin Capsules. A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried. (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

In another aspect, the present invention provides a method of antagonizing $CRF_1$ receptors in a warm-blooded animal, comprising administering to the animal a compound of the invention at amount effective to antagonize $CRF_1$ receptors.

In another aspect, the present invention provides a method of treating a disorder in a warm-blooded animal, which disorder manifests hypersecretion of CRF, or the treatment of which disorder can be effected or facilitated by antagonizing $CRF_1$ receptors, comprising administering to the animal a therapeutically effective amount of a compound of the invention. It is preferred that the warm-blooded animal is a mammal, more preferred that the animal is a human.

In another aspect, the present invention provides a method for screening for ligands for $CRF_1$ receptors, which method comprises: a) carrying out a competitive binding assay with $CRF_1$ receptors, a compound of formula I which is labelled with a detectable label, and a candidate ligand; and b) determining the ability of said candidate ligand to displace said labelled compound. One method for this assay is described in example 1.

In another aspect, the present invention provides a method for detecting CRF receptors in tissue comprising: a) contacting a compound of formula I, which is labelled with a detectable label, with a tissue, under conditions that permit binding of the compound to the tissue; and b) detecting the labelled compound bound to the tissue.

In another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the CRF-1 receptor.

In another aspect, the present invention provides an article of manufacture comprising: a) packaging material; b) a pharmaceutical agent comprising a compound of the invention contained within said packaging material; and c) a label or package insert which indicates that said pharmaceutical agent can be used for treating a disorder described below.

Compounds of the invention are useful for treating various disorders in a mammal including social anxiety disorder; panic disorder; obsessive-compulsive disorder; anxiety with co-morbid depressive illness; affective disorder; anxiety; depression; irritable bowel syndrome; post-traumatic stress disorder; supranuclear palsy; immune suppression; gastrointestinal disease; anorexia nervosa or other feeding disorder; drug or alcohol withdrawal symptoms; substance abuse disorder (e.g., nicotine, cocaine, ethanol, opiates, or other drugs); inflammatory disorder, fertility problems; disorders the treatment of which can be effected or facilitated by antagonizing CRF, including but not limited to disorders induced or facilitated by CRF; a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); osteoporosis; psychosocial dwarfism and hypoglycemia.

Thus, in still another aspect, the present invention provides a method of treating a disorder described herein above, comprising administering to the mammal a therapeutically effective amount of a compound of the invention.

Particular disorders that can be treated by the method of the invention preferably include the following: generalized anxiety disorder; social anxiety disorder; anxiety; obsessive-compulsive disorder; anxiety with co-morbid depressive illness; panic disorder; mood disorders such as depression, including major depression, single episode depression, recurrent depression, child abuse induced depression, and postpartum depression; bipolar disorders; post-traumatic stress disorder; substance abuse disorder (e.g., nicotine, cocaine, ethanol, opiates, or other drugs); inflammatory disorders such as rheumatoid arthritis and osteoarthritis; gastrointestinal diseases such as irritable bowel syndrome, ulcers, Crohn's disease, spastic colon, diarrhea, and post operative ilius and colonic hypersensitivity associated by psychopathological disturbances or stress; inflammatory disorder; and skin disorders such as acne and psoriasis.

Particular disorders that can be treated by the method of the invention more preferably include the following: generalized anxiety disorder; social anxiety disorder; anxiety; obsessive-compulsive disorder; anxiety with co-morbid depressive illness; panic disorder; and mood disorders such as depression, including major depression, single episode depression, recurrent depression, child abuse induced depression, and postpartum depression.

A compound of this invention can be administered to treat the above disorders or abnormalities by means that produce contact of the active agent with the agent's site of action in the body of a mammal, such as by oral or parenteral administration using appropriate dosage forms. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The effective dose may vary, depending upon factors such as the condition of the patient, the severity of the symptoms of the disease, the pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Definitions and Conventions

The term "aryl" means either phenyl or naphthyl;

The term "substituted aryl" means an aryl group optionally substituted with 1–5 substituents independently selected from halogen, $-NO_2$, $-CN$, $-R_a$, $OR_a$, $-S(O)_mR_a$, $-NR_aR_a$, $-C(O)NR_aR_a$, $-C(S)NR_aR_a$, $-S(O)_mNR_aR_a$, $-NR_aS(O)_mR_a$, $-NR_aC(O)OR_a$, $-NR_aC(S)OR_a$, $-OC(O)NR_aR_a$, $-OC(S)NR_aR_a$, $-NR_aC(O)NR_aR_a$, $-NR_aC(S)NR_aR_a$, $-C(O)OR_a$, $-C(S)OR_a$, $-OC(O)R_a$, $-OC(S)R_a$ and $-OC(O)OR_a$;

The term "heteroaryl" means a radical attached via a ring carbon or nitrogen atom of a monocyclic aromatic ring containing five or six ring atoms consisting of carbon and 1, 2, 3, or 4 heteroatoms each selected from the group consisting of non-peroxide O, S, N, with appropriate bonding to satisfy valence requirements as well as a radical (attachment at either carbon or nitrogen) of a fused bicyclic heteroaromatic of about eight to ten ring atoms, and includes radicals such as thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl;

The term "substituted heteroaryl" means a heteroaryl group having 1–5 substituents independently selected from halogen, $-NO_2$, $-CN$, $-R_a$, $-OR_a$, $-S(O)_mR_a$, $-NR_aR_a$, $-C(O)NR_aR_a$, $-C(S)NR_aR_a$, $-S(O)_mNR_aR_a$, $-NR_aS(O)_mR_a$, $-NR_aC(O)OR_a$, $-NR_aC(S)OR_a$, $-OC$ (O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, —OC(S)R$_a$ and —OC(O)OR$_a$ The term "aryl cycloalkyl" means a bicyclic ring system containing 8 to 14 carbon atoms wherein one ring is aryl and the other ring is fused to the aryl ring and may be fully or partially saturated in the portion of the ring fused to the aryl ring, provided that either ring may act as a point of attachment;

The term "substituted aryl cycloalkyl" means an aryl cycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$ —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, —OC(S)R$_a$ and —OC(O)OR$_a$;

The term "heteroaryl cycloalkyl" means a bicyclic ring system containing 8 to 14 atoms, wherein one ring is heteroaryl and the other ring is fused to the heteroaryl ring and may be fully or partially saturated in the portion of the ring fused to the heteroaryl ring, provided that either ring may act as a point of attachment;

The term "substituted heteroaryl cycloalkyl" means a heteroaryl cycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$ —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —C(O)OR$_a$, —C(S)OR$_a$, —OC(O)R$_a$, —OC(S)R$_a$ and —OC(O)OR$_a$;

The term "aryl heterocycloalkyl" means a bicyclic ring system containing 8 to 14 atoms, wherein one ring is aryl and the other ring is heterocycloalkyl, provided that either ring may act as a point of attachment;

The term "substituted aryl heterocycloalkyl" means an aryl heterocycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$ —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, —OC(S)R$_a$ and —OC(O)OR$_a$;

The term "heteroaryl heterocycloalkyl" means a bicyclic ring system containing 8 to 14 atoms, wherein one ring is heteroaryl and the other ring is heterocycloalkyl, provided that either ring may act as a point of attachment;

The term "substituted heteroaryl heterocycloalkyl" means an heteroaryl heterocycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$ —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, —OC(S)R$_a$ and —OC(O)OR$_a$;

The term "heterocycloalkyl", unless otherwise specified, means a 4 to 8 membered monocyclic ring or bicyclic ring, wherein at least one carbon atom is replaced with a heteromember selected from oxygen, nitrogen, —NH—, or —S(O)$_m$— wherein m is zero, 1, or 2, optionally containing from one to three double bonds, provided that the molecule is not aromatic; and provided that ring attachment can occur at either a carbon or nitrogen atom; Heterocycloalkyl includes tetrahydrofuranyl, tetrahydropyranyl, morpholinyl, pyrrolidinyl, piperidinyl, piperazinyl, [2.2.1]-azabicyclic rings, [2.2.2]-azabicyclic rings, [3.3.1]-azabicyclic rings, quinuclidinyl, azetidinyl, azetidinonyl, oxindolyl, dihydroimidazolyl, and pyrrolidinonyl The term "substituted heterocycloalkyl" is a heterocycloalkyl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$ —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, —OC(S)R$_a$ and —OC(O)OR$_a$;

Halogen is a group selected from —F, —Cl, —Br, and —I;

The term "alkyl" means both straight and branched chain moieties having from 1–10 carbon atoms optionally containing one or more double or triple bonds;

The term "substituted alkyl" means an alkyl moiety having 1–3 substituents independently selected from halogen, —S(O)$_m$R$_a$, —NR$_a$R$_a$, —C(O)R$_a$, —CN, —C(O)NR$_a$R$_a$, —C(S)NR$_a$R$_a$, —NR$_a$C(O)R$_a$, —NR$_a$C(S)R$_a$, —S(O)$_2$NR$_a$R$_a$, —NR$_a$S(O)$_2$R$_a$, CN, —NO$_2$, and Ar provided that a halogen or halogens may not be the only substituent(s) on the alkyl group;

The term "cycloalkyl" means a monocyclic or bicyclic alkyl moiety, having from 3–10 carbon atoms optionally containing 1 to 2 double bonds provided that the moiety is not aromatic;

The term "substituted cycloalkyl" means a cycloalkyl group having 1–3 substituents independently selected from halogen, —R$_a$, —OR$_a$, —S(O)$_m$R$_a$, —NR$_a$R$_a$, —C(O)R$_a$, C(S)R$_a$, —CN, —C(O)NR$_a$R$_a$, —C(S)NR$_a$R$_a$, —NR$_a$C(O)R$_a$, —NR$_a$C(S)R$_a$, —S(O)$_2$NR$_a$R$_a$, —NR$_a$S(O)$_2$R$_a$, and —NO$_2$;

The term "haloalkyl" means an alkyl moiety having from 1–10 carbon atoms and having 1 to (2v+1) independently selected halogen substituent(s) where v is the number of carbon atoms in the moiety;

The term "pharmaceutically acceptable salt" refers to a salt which retains the biological effectiveness and properties of the compounds of this invention and which is not biologically or otherwise undesirable. Typical pharmaceutically acceptable salts include those salts prepared by reaction of the compounds of the present invention with a pharmaceutically acceptable mineral or organic acid or an organic or inorganic base. Such salts are known as acid addition and base addition salts.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "prodrug" means compounds that are transformed in vivo to yield a compound of Formula I. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "therapeutically effective amount," "effective amount," "therapeutic amount," or "effective dose" is meant that amount sufficient to elicit the desired pharmacological or therapeutic effects, thus resulting in effective prevention or treatment of the disease.

The term "pharmaceutically acceptable" means that the carrier, diluent, excipients, and/or salt must be compatible with the other ingredients of the formulation, and not deleterious to the patient.

The phrases "a compound of the present invention," "compounds of the present invention," or "a compound in accordance with Formula I" and the like, refers to a stereoisomer, pharmaceutically acceptable salt, or prodrug of a compound of Formula I, or a pharmaceutically acceptable salt of a prodrug of a compound of formula I.

The terms "treating," "treat," or "treatment" means ameliorating, attenuating, or eliminating one or more symptom of a particular disease or condition, or preventing or delaying the onset of one of more symptom of a particular disease or condition. These terms also include preventative (e.g., prophylactic) and palliative treatment. Prevention of the disease is manifested by a prolonging or delaying of the onset of the symptoms of the disease.

EXAMPLES

The following examples are provided to describe the invention in further detail. They are intended to illustrate and not to limit the invention.

Biological Examples

Example 1

In Vitro CRF-R1 Receptor Binding Assay for the Evaluation of Biological Activity The following is a description of a standard in vitro binding assay for the evaluation of biological activity of a test compound on CRF1 receptors. It is based on a modified protocol described by De Souza (De Souza, 1987).

The binding assay utilizes brain membranes, commonly from rats. To prepare brain membranes for binding assays, rat frontal cortex is homogenized in 10 mL of ice cold tissue buffer (50 mM HEPES buffer pH 7.0, containing 10 mM $MgCl_2$, 2 mM EGTA, 1 µg/ml aprotinin, 1 µg/ml leupeptin and 1 µg/ml pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 µg/mL.

Binding assays are performed in 96 well plates at a final volume of 300 µL. The assays are initiated by the addition of 150 µL membrane suspension to 150 µL of assay buffer containing $^{125}$I-ovine-CRF (final concentration 150 pM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvestor. Filters are washed three times with ice cold phosphate buffered saline pH 7.0 containing 0.01% Triton X-100. Filters are assessed for radioactivity in a Packard TopCount.

Alternatively, tissues and cells that naturally express CRF receptors, such as IMR-32 human neuroblastoma cells (ATCC; Hogg et al., 1996), can be employed in binding assays analogous to those described above.

A compound is considered to be active if it has an $IC_{50}$ value of less than about 10 µM for the inhibition of CRF. Nonspecific binding is determined in the presence of excess (10 µM) α-helical CRF.

Example 2

Ex Vivo CRF-R1 Receptor Binding Assay for the Evaluation of Biological Activity

The following is a description of a typical ex vivo CRF-R1 receptor binding assay for assessing the biological activity of a test compound on CRF1 receptors.

Fasted, male, Harlen-bred, Sprague-Dawley rats (170–210 g) were orally dosed with test compound or vehicle, via gastric lavage between 12:30 and 2:00 PM. Compounds were prepared in vehicle (usually 10% soybean oil, 5% polysorbate 80, in dH20). Two hours after drug administration, rats were sacrificed by decapitation, frontal cortices were quickly dissected and placed on dry ice, then frozen at −80° C. until assayed; trunk blood was collected in heparinized tubes, plasma separated by centrifugation (2500 RPM's for 20 minutes), and frozen at −20° C.

On the day of the binding assay, tissue samples were weighed and allowed to thaw in ice cold 50 mM Hepes buffer (containing 10 mM $MgCl_2$, 2 mM EGTA, 1 µg/ml aprotinin, 1 µg/ml leupeptin hemisulfate, and 1 µg/ml pepstatin A, 0.15 mM bacitracin, and 0.1% ovalalbumin, pH=7.0 at 23° C.) and then homogenized for 30 sec at setting 5 (Polytron by Kinematica). Homogenates were incubated (two hours, 23° C., in the dark) with $[^{125}I]$ CRF (0.15 nM, NEN) in the presence of assay buffer (as described above) or DMP-904 (10 µM). The assay was terminated by filtration (Packard FilterMate, GF/C filter plates); plates were counted in Packard TopCount LSC; total and non-specific fmoles calculated from DPM's. Data are expressed as % of vehicle controls (specific fmoles bound). Statistical significance was determined using student's t-test.

Example 3

Inhibition of CRF Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/$[^{32}P]$ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of $[^{3}H]$cAMP (approximately 40,000 dpm) is added to each tube prior to separation. The separation of $[^{32}P]$cAMP from $[^{32}P]$ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Example 4

In Vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). A compound may be tested in any species of rodent or small mammal.

What is claimed is:

1. A compound of Formula I,

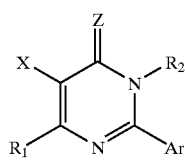

Formula I a stereoisomer thereof, or a pharmaceutically acceptable salt thereof, wherein:

X is $NR_3R_4$;

Z is —O;

Ar is selected from aryl and substituted aryl, $R_1$ is selected from halogen, —$NO_2$, —CN, —$R_a$, —$OR_a$, —$S(O)_mR_a$, —$NR_aR_a$, —$C(O)NR_aR_a$, —$C(S)NR_aR_a$ —$S(O)_mNR_aR_a$, —$NR_aS(O)_mR_a$, —$NR_aC(O)OR_a$, —$NR_aC(S)OR_a$, —$OC(O)NR_aR_a$, —$OC(S)NR_aR_a$, —$NR_aC(O)NR_aR_a$, —$NR_aC(S)NR_aR_a$, —$C(O)OR_a$, —$C(S)OR_a$, or —$OC(O)OR_a$;

$R_2$ is selected from —$R_a$, —$S(O)_mR_a$, —$C(O)NR_aR_a$, —$C(S)NR_aR_a$ —$S(O)_mNR_aR_a$, —$C(O)OR_a$, —$C(S)OR_a$, or —$OC(O)OR_a$;

$R_3$ and $R_4$ are independently selected from $R_a$, heterocycloalkyl, substituted heterocycloalkyl, substituted heteroaryl, substituted aryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl provided that at least one of $R_3$ or $R_4$ are heteroaryl, substituted heteroaryl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, substituted heteroaryl heterocycloalkyl, heterocycloalkyl or substituted heterocycloalkyl;

$R_a$ each is selected from H, alkyl, cycloalkyl, haloalkyl, aryl, heteroaryl, or heterocycloalkyl optionally substituted with 1 to 5 of $R_t$, —$OR_t$, —$S(O)_mR_t$, $NR_tR_t$, oxo (=O), thione (=S), phenyl, heteroaryl, or heterocycloalkyl where phenyl, heteroaryl, and heterocycloalkyl are optionally substituted with 1 to 5 independently taken from $R_t$; and $R_t$ each is selected from H, halogen, —$NO_2$, —$NH_2$, —OH, —SH, —CN, —$C(O)NH_2$, —C(O)—NHalkyl, —C(O)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, alkyl, cycloalkyl, haloalkyl, phenyl, benzyl, heteroaryl, or heterocycloalkyl where phenyl, benzyl heteroaryl and heterocycloalkyl may be optionally substituted with alkyl or halogen.

2. A compound according to claim 1, which is a compound of formula II.

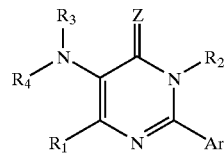

Formula II

3. A compound of formula II according to claim 2, which is a compound of formula III.

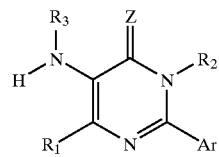

Formula III

4. A compound of formula III according to claim 3, which is a compound of formula IV,

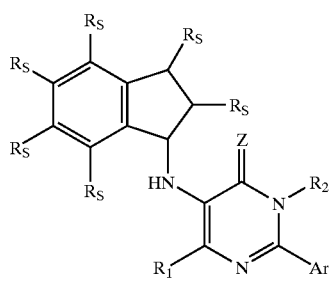

Formula IV wherein in formula IV, $R_s$ each is independently selected from halogen, —$NO_2$, —CN, —$R_a$, —$OR_a$, —$S(O)_mR_a$, —$NR_aR_a$, —C(O)$NR_aR_a$, —$C(S)NR_aR_a$ —$S(O)_mNR_aR_a$, —$NR_aS(O)_mR_a$, —$NR_aC(O)OR_a$, —$NR_aC(S)OR_a$, —OC(O)$NR_aR_a$, —$OC(S)NR_aR_a$, —$NR_aC(O)NR_aR_a$, —$NR_aC(S)NR_aR_a$, —$C(O)OR_a$, —$C(S)OR_a$, —$OC(O)R_a$, —$OC(S)R_a$, or —$OC(O)OR_a$.

5. A compound of formula IV according to claim 4, which is a compound of formula V.

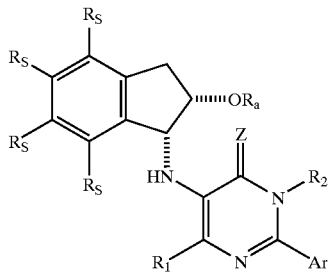

Formula V

6. A compound of formula III according to claim 3, which is a compound of formula VI,

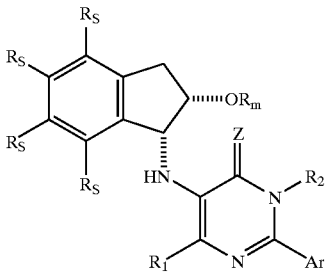

Formula VI wherein in formula VI, $R_s$ each is independently selected from halogen, —$NO_2$, —CN, —$R_a$, —$OR_a$, —$S(O)_mR_a$, —$NR_aR_a$, —C(O)$NR_aR_a$, —C(S)$NR_aR_a$ —$S(O)_mNR_aR_a$, —$NR_aS(O)_mR_a$, —$NR_aC(O)OR_a$, —$NR_aC(S)OR_a$, —OC(O)$NR_aR_a$, —OC(S)$NR_aR_a$, —$NR_aC(O)NR_aR_a$, —$NR_aC(S)NR_aR_a$, —C(O)$OR_a$, —C(S)$OR_a$, —OC(O)$R_a$, —OC(S)$R_a$, or —OC(O)$OR_a$, and $R_m$ is $C_1$–$C_6$ alkyl substituted with from 1–2 of halogen, —$NO_2$, —$NH_2$, —OH, —SH, —CN, —C(O)$NH_2$, —C(S)$NH_2$, —C(O)—NHalkyl, —C(S)—NHalkyl, —C(O)Nalkylalkyl, —C(S)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, oxo (=O), thione (=S), heterocycloalkyl, or substituted heterocycloalkyl.

7. A compound of formula III according to claim 3, which is a compound of formula VII,

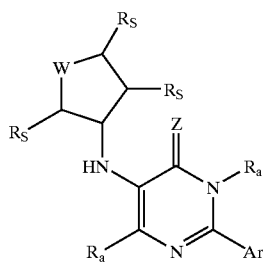

Formula VII wherein in formula VII,

W is O, $NR_p$, or $S(O)_m$; and $R_p$ each is independently selected from —$R_a$, —$S(O)_mR_a$, —C(O)$NR_aR_a$, —C(S)$NR_aR_a$ —$S(O)_mNR_aR_a$, —C(O)$OR_a$, or —C(S)$OR_a$.

8. A compound of formula III according to claim 3, which is a compound of formula VIII,

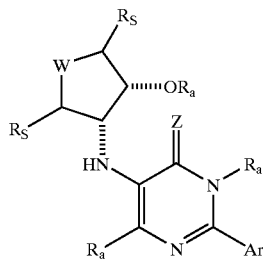

Formula VIII wherein in formula VIII,

W is O, $NR_p$, or $S(O)_m$; and $R_p$ each is independently selected from —$R_a$, —$S(O)_mR_a$, —C(O)$NR_aR_a$, —C(S)$NR_aR_a$ —$S(O)_mNR_aR_a$, —C(O)$OR_a$, or —C(S)$OR_a$.

9. A compound of formula III according to claim 3, which is a compound of formula IX,

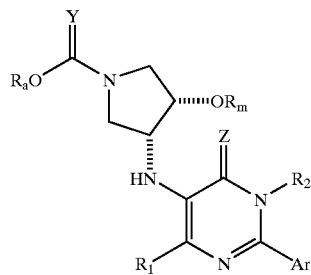

Formula IX wherein in formula IX,

Y is O or S, and $R_m$ is $C_1$–$C_6$ alkyl substituted with from 1–2 of halogen, —$NO_2$, —$NH_2$, —OH, —SH, —CN, —C(O)$NH_2$, —C(S)$NH_2$, —C(O)—NHalkyl, —C(S)—NHalkyl, —C(O)Nalkylalkyl, —C(S)Nalkylalkyl, —Oalkyl, NHalkyl, Nalkylalkyl, —$S(O)_m$alkyl, $SO_2NH_2$, $SO_2$NHalkyl and $SO_2$Nalkylalkyl, oxo (=O), thione (=S), heterocycloalkyl, or substituted heterocycloalkyl.

10. A compound selected from the group consisting of:
(1R,2S)-1-{[2-(2,4-Dichlorophenyl)-1,4-dimethyl-6-oxo-1,6-dihydropyrimidin-5-yl]amino}-2,3-dihydro-1H-inden-2-yl acetate (1R,2S)-1-{[2-(2-Chloro-4-methoxyphenyl)-1,4-dimethyl-6-oxo-1,6-dihydropyrimidin-5-yl]amino}-2,3-dihydro-1H-inden-2-yl acetate (1R,2S)-1-{[2-(2-Methyl-4-methoxyphenyl)-1,4-dimethyl-6-oxo-1,6-dihydropyrimidin-5-yl]amino}-2,3-dihydro-1H-inden-2-yl acetate (1R,2S)-1-{[2-(2-Chloro-4-dimethylaminophenyl)-1,4-dimethyl-6-oxo-1,6-dihydropyrimidin-5-yl]amino}-2,3-dihydro-1H-inden-2-yl acetate (1R,2S)-1-{[2-(2-Chloro-4-trifluoromethylphenyl)-1,4-dimethyl-6-oxo-1,6-dihydropyrimidin-5-yl]amino}-2,3-dihydro-1H-inden-2-yl acetate (1R,2S)-1-{[2-(2-Trifluoromethyl-4-dimethylaminophenyl)-1,4-dimethyl-6-oxo-1,6-dihydropyrimidin-5-yl]amino}-2,3-dihydro-1H-inden-2-yl acetate (1R,2S)-1-{[4-Ethyl-2-(2,4-dichlorophenyl)-1-methyl-6-oxo-1,6-dihydropyrimidin-5-yl]amino}-2,3-dihydro-1H-inden-2-yl acetate (1R,2S)-1-{[4-Ethyl-2-(2-chloro-4-methoxyphenyl)-1-methyl-6-oxo-1,6-dihydropyrimidin-5-yl]amino}-2,3-dihydro-1H-inden-2-yl acetate (1R,2S)-1-{[4-Ethyl-2-(2-methyl-4-methoxyphenyl)-1-methyl-6-oxo-1,6-dihydropyrimidin-5-yl]amino}-2,3-dihydro-1H-inden-2-yl acetate (1R,2S)-1-{[4-Ethyl-2-(2-chloro-4-dimethylaminophenyl)-1-methyl-6-oxo-1,6-dihydropyrimidin-5-yl]amino}-2,3-dihydro-1H-inden-2-yl acetate (1R,2S)-1-{[4-Ethyl-2-(2-chloro-4-trifluoromethylphenyl)-1-methyl-6-oxo-1,6-dihydropyrimidin-5-yl]amino}-2,3-dihydro-1H-inden-2-yl acetate (1R,2S)-1-{[4-Ethyl-2-(2-trifluoromethyl-4-dimethylaminophenyl)-1-methyl-6-oxo-1,6-dihydropyrimidin-5-yl]amino}-2,3-dihydro-1H-inden-2-yl acetate (1R,2S)-1-{[4-Methyl-2-(2-dichlorophenyl-1-ethyl-6-oxo-1,6-dihydropyrimidin-5-yl]amino}-2,3-dihydro-1H-inden-2-yl acetate (1R,2S)-1-{[4-Methyl-2-(2-chloro-4-methoxyphenyl)-1-ethyl-6-oxo-1,6-dihydropyrimidin-5-yl]amino}-2,3-dihydro-1H-inden-2-yl acetate (1R,2S)-1-{[4-Methyl-2-(2-methyl-4-methoxyphenyl)-1-ethyl-6-oxo-1,6-dihydropyrimidin-5-yl]amino}-2,3-dihydro-1H-inden-2-yl acetate (1R,2S)-1-{[4-Methyl-2-(2-chloro-4-dimethylaminophenyl)-1-ethyl-6-oxo-1,6-dihydropyrimidin-5-yl]amino}-2,3-dihydro-1H-inden-2-yl acetate (1R,2S)-1-{[4-Methyl-2-(2-chloro-4-trifluoromethylphenyl)-1-ethyl-6-oxo-1,6-dihydropyrimidin-5-yl]amino}-2,3-dihydro-1H-inden-2-yl acetate (1R,2S)-1-{[4-Methyl-2-(2-trifluoromethyl-4-dimethylaminophenyl)-1-ethyl-6-oxo-1,6-dihydropyrimidin-5-yl]amino}-2,3-dihydro-1H-inden-2-yl acetate (1R,2S)-1-{[2-(2,4-Dichlorophenyl)-1,4-diethyl-6-oxo-1,6-dihydropyrimidin-5-yl]amino}-2,3-dihydro-1H-inden-2-yl acetate (1R,2S)-1-{[2-(2-Chloro-4-methoxyphenyl)-1,4-diethyl-6-oxo-1,6-dihydropyrimidin-5-yl]amino}-2,3-dihydro-1H-inden-2-yl acetate (1R,2S)-1-{[2-(2-Methyl-4-methoxyphenyl)-1,4-diethyl-6-oxo-1,6-dihydropyrimidin-5-yl]amino}-2,3-dihydro-1H-inden-2-yl acetate (1R,2S)-1-{[2-(2-Chloro-4-dimethylaminophenyl)-1,4-diethyl-6-oxo-1,6-dihydropyrimidin-5-yl]amino}-2,3-dihydro-1H-inden-2-yl acetate (1R,2S)-1-{[2-(2-Chloro-4-trifluoromethylphenyl)-1,4-diethyl-6-oxo-1,6-dihydropyrimidin-5-yl]amino}-2,3-dihydro-1H-inden-2-yl acetate (1R,2S)-1-{[2-(2-Trifluoromethyl-4-dimethylaminophenyl)-1,4-diethyl-6-oxo-1,6-dihydropyrimidin-5-yl]amino}-2,3-dihydro-1H-inden-2-yl acetate 2-(2,4-Dichlorophenyl)-5-{[(1R,2S)-2-ethoxy-2,3-dihydro-1H-inden-1-yl]amino}-3,6-dimethylpyrimidin-4(3H)-one 2-(2-Chloro-4-methoxyphenyl)-5-{[(1R,2S)-2-ethoxy-2,3-dihydro-1H-inden-1-yl]amino}-3,6-dimethylpyrimidin-4(3H)-one 2-(2-Methyl-4-methoxyphenyl)-5-{[(1R,2S)-2-ethoxy-2,3-dihydro-1H-inden-1-yl]amino}-3,6-dimethylpyrimidin-4(3H)-one 2-(2-Chloro-4-dimethylaminophenyl)-5-{[(1R,2S)-2-ethoxy-2,3-dihydro-1H-inden-1-yl]amino}-3,6-dimethylpyrimidin-4(3H)-one 2-(2-Chloro-4-trifluoromethylphenyl)-5-{[(1R,2S)-2-ethoxy-2,3-dihydro-1H-inden-1-yl]amino}-3,6-dimethylpyrimidin-4(3H)-one 2-(2-Trifluoromethyl-4-dimethylaminophenyl)-5-{[(1R,2S)-2-ethoxy-2,3-dihydro-1H-inden-1-yl]amino}-3,6-dimethylpyrimidin-4(3H)-one 2-(2,4-Dichlorophenyl)-5-{[(1R,2S)-2-ethoxy-2,3-dihydro-1H-inden-1-yl]amino}-6-ethyl-3-methylpyrimidin-4(3H)-one 2-(2-Chloro-4-methoxyphenyl)-5-{[(1R,2S)-2-ethoxy-2,3-dihydro-1H-inden-1-yl]amino}-6-ethyl-3-methylpyrimidin-4(3H)-one 2-(2-Methyl-4-methoxyphenyl)-5-{[(1R,2S)-2-ethoxy-2,3-dihydro-1H-inden-1-yl]amino}-6-ethyl-3-methylpyrimidin-4(3H)-one 2-(2-Chloro-4-dimethylaminophenyl)-5-{[(1R,2S)-2-ethoxy-2,3-dihydro-1H-inden-1-yl]amino}-6-ethyl-3-methylpyrimidin-4(3H)-one 2-(2-Chloro-4-trifluoromethylphenyl)-5-{[(1R,2S)-2-ethoxy-2,3-dihydro-1H-inden-1-yl]amino}-6-ethyl-3-methylpyrimidin-4(3H)-one 2-(2-Trifluoromethyl-4-dimethylaminophenyl)-5-{[(1R,2S)-2-ethoxy-2,3-dihydro-1H-inden-1-yl]amino}-6-ethyl-3-methylpyrimidin-4(3H)-one 2-(2,4-Dichlorophenyl)-5-{[(1R,2S)-2-ethoxy-2,3-dihydro-1H-inden-1-yl]amino}-6-methyl-3-ethylpyrimidin-4(3H)-one 2-(2-Chloro-4-methoxyphenyl)-5-{[(1R,2S)-2-ethoxy-2,3-dihydro-1H-inden-1-yl]amino}-6-methyl-3-ethylpyrimidin-4(3H)-one 2-(2-Methyl-4-methoxyphenyl)-5-{[(1R,2S)-2-ethoxy-2,3-dihydro-1H-inden-1-yl]amino}-6-methyl-3-ethylpyrimidin-4(3H)-one 2-(2-Chloro-4-dimethylaminophenyl)-5-{[(1R,2S)-2-ethoxy-2,3-dihydro-1H-inden-1-yl]amino}-6-methyl-3-ethylpyrimidin-4(3H)-one 5-{[(1R,2S)-2-Ethoxy-2,3-dihydro-1H-inden-1-yl]amino}-6-methyl-2-(6-methoxy-2-methylpyridin-3-yl)-3-ethylpyrimidin-4(3H)-one 2-(2-Chloro-4-trifluoromethylphenyl)-5-{[(1R,2S)-2-ethoxy-2,3-dihydro-1H-inden-1-yl]amino}-6-methyl-3-ethylpyrimidin-4(3H)-one 2-(2-Trifluoromethyl-4-dimethylaminophenyl)-5-{[(1R,2S)-2-ethoxy-2,3-dihydro-1H-inden-1-yl]amino}-6-methyl-3-ethylpyrimidin-4(3H)-one 2-(2,4-Dichlorophenyl)-5-{[(1R,2S)-2-ethoxy-2,3-dihydro-1H-inden-1-yl]amino}-3,6-diethylpyrimidin-4(3H)-one 2-(2-Chloro-4-methoxyphenyl)-5-{[(1R,2S)-2-ethoxy-2,3-dihydro-1H-inden-1-yl]amino}-3,6-diethylpyrimidin-4(3H)-one 2-(2-Methyl-4-methoxyphenyl)-5-{[(1R,2S)-2-ethoxy-2,3-dihydro-1H-inden-1-yl]amino}-3,6-diethylpyrimidin-4(3H)-one 2-(2-Chloro-4-dimethylaminophenyl)-5-{[(1R,2S)-2-ethoxy-2,3-dihydro-1H-inden-1-yl]amino}-3,6-diethylpyrimidin-4(3H)-one 2-(2-Chloro-4-trifluoromethylphenyl)-5-{[(1R,2S)-2-ethoxy-2,3-dihydro-1H-inden-1-yl]amino}-3,6-diethylpyrimidin-4(3H)-one 2-(2-Trifluoromethyl-4-dimethylaminophenyl)-5-{[(1R,2S)-2-ethoxy-2,3-dihydro-1H-inden-1-yl]amino}-3,6-diethylpyrimidin-4(3H)-one 5-[(1-Ethylpropyl)amino]-2-(6-methoxy-2,3-dihydro-1H-inden-5-yl)-3,6-dimethylpyrimidin-4(3H)-one 2-(6-Chloro-2,3-dihydro-1H-inden-5-yl)-5-[(1-ethylpropyl)amino]-3,6-dimethylpyrimidin-4(3H)-one 2-(6-Chloro-1-oxo-2,3-dihydro-1H-inden-5-yl)-5-[(1-ethylpropyl)amino]-3,6-dimethylpyrimidin-4(3H)-one 3-Ethyl-5-[(1-ethylpropyl)amino]-2-(6-methoxy-2,3-dihydro-1H-inden-5-yl)-6-methylpyrimidin-4(3H)-one 2-(6-Chloro-2,3-dihydro-1H-inden-5-yl)-3-ethyl-5-[(1-ethylpropyl)amino]-6-methylpyrimidin-4(3H)-one 3-Ethyl-2-(6-methoxy-2,3-dihydro-1H-inden-5-yl)-5-{[2-methoxy-1-(methoxymethyl)ethyl]amino}-6-methylpyrimidin-4(3H)-one 2-(6-Chloro-2,3-dihydro-1H-inden-5-yl)-3-ethyl-5-{[2-methoxy-1-(methoxymethyl)ethyl]amino}-6-methylpyrimidin-4(3H)-one 2-(6-Chloro-1-oxo-2,3-dihydro-1H-inden-5-yl)-3-ethyl-5-[(1-ethylpropyl)amino]-6-methylpyrimidin-4(3H)-one 2-(6-Chloro-1-oxo-2,3-dihydro-1H-inden-5-yl)-3-ethyl-5-{[2-methoxy-1-(methoxymethyl)ethyl]amino}-6-methylpyrimidin-4(3H)-one 2-(6-Chloro-2,3-dihydro-1H-inden-5-yl)-6-ethyl-5-[(1-ethylpropyl)amino]-3-methylpyrimidin-4(3H)-one 6-Ethyl-2-(6-methoxy-2,3-dihydro-1H-inden-5-yl)-5-{[2-methoxy-1-(methoxymethyl)ethyl]amino}-3-methylpyrimidin-4(3H)-one 2-(6-Chloro-2,3-dihydro-1H-inden-5-yl)-6-ethyl-5-{[2-methoxy-1-(methoxymethyl)ethyl]amino}-3-methylpyrimidin-4(3H)-one 2-(6-Chloro-1-oxo-2,3-dihydro-1H-inden-5-yl)-6-ethyl-5-[(1-ethylpropyl)amino]-3-methylpyrimidin-4(3H)-one 2-(6-Chloro-1-oxo-2,3-dihydro-1H-inden-5-yl)-6-ethyl-5-{[2-methoxy-1-(methoxymethyl)ethyl]amino}-3-methylpyrimidin-4(3H)-one 5-[(1-Ethylpropyl)amino]-2-(6-methoxy-2,3-dihydro-1H-inden-5-yl)-3,6-diethylpyrimidin-4(3H)-one 2-(6-Chloro-2,3-dihydro-1H-inden-5-yl)-5-[(1-ethylpropyl)amino]-3,6-diethylpyrimidin-4(3H)-one 2-(6-Methoxy-2,3-dihydro-1H-inden-5-yl)-5-{[2-methoxy-1-(methoxymethyl)ethyl]amino}-3,6-diethylpyrimidin-4(3H)-one 2-(6-Chloro-2,3-dihydro-1H-inden-5-yl)-5-{[2-methoxy-1-(methoxymethyl)ethyl]amino}-3,6-diethylpyrimidin-4(3H)-one 5-[(1-Ethylpropyl)amino]-2-(6-methoxy-1-oxo-2,3-dihydro-1H-inden-5-yl)-3,6-diethylpyrimidin-4(3H)-one 2-(6-Chloro-1-oxo-2,3-dihydro-1H-inden-5-yl)-5-[(1-ethylpropyl)amino]-3,6-diethylpyrimidin-4(3H)-one 2-(6-Chloro-1-oxo-2,3-dihydro-1H-inden-5-yl)-5-{[2-methoxy-1-(methoxymethyl)ethyl]amino}-3,6-diethylpyrimidin-4(3H)-one.

11. A pharmaceutical composition comprising a compound of claim 1.

12. An article of manufacture comprising: a) a packaging material; b) a pharmaceutical agent comprising a compound of claim 1, which pharmaceutical agent is contained within the packaging material, and c) a label or package insert contained within said packaging material indicating that said pharmaceutical agent is for treating anxiety, or depression.

13. A method of treating a disorder in a mammal, comprising administering to the mammal in need thereof an effective amount of a compound of claim 1, wherein the disorder is selected from social anxiety disorder; anxiety with co-morbid depressive illness; anxiety; depression; post-traumatic stress disorder; drug or alcohol withdrawal symptoms; generalized anxiety disorder; and bipolar disorders.

14. The method according to claim 13 wherein the disorder is selected from anxiety; depression; generalized anxiety disorder; social anxiety disorder; anxiety with co-morbid depressive illness; bipolar disorders; and post-traumatic stress disorder.

15. The method according to claim 14 wherein the disorder is selected from anxiety, and depression.

16. The method according to claim 13 wherein the mammal is a human.

17. A compound of claim 1 wherein, in a standard in vitro CRF receptor binding assay, the compound exhibits an $IC_{50}$ value of 1 micromolar or less.

18. A compound of claim 17 wherein the compound exhibits an $IC_{50}$ value of 100 nanomolar or less.

19. A compound of claim 18 wherein the compound exhibits an $IC_{50}$ value of 10 nanomolar or less.

20. The method according to claim 13 wherein, in a standard in vitro CRF receptor binding assay, the compound exhibits an $IC_{50}$ value of 1 micromolar or less.

21. The method according to claim 13 wherein, in a standard in vitro CRF receptor binding assay, the compound exhibits an $IC_{50}$ value of 100 nanomolar or less.

* * * * *